(12) United States Patent
Tu et al.

(10) Patent No.: US 7,708,711 B2
(45) Date of Patent: May 4, 2010

(54) OCULAR IMPLANT WITH THERAPEUTIC AGENTS AND METHODS THEREOF

(75) Inventors: Hosheng Tu, Newport Coast, CA (US); Barbara Niksch, Laguna Niguel, CA (US); David Haffner, Mission Viejo, CA (US); Gregory Smedley, Aliso Viejo, CA (US); Olav B. Bergheim, Laguna Hills, CA (US); Morteza (Mory) Gharib, San Marino, CA (US)

(73) Assignee: Glaukos Corporation, Laguna Hills, CA (US)

( * ) Notice: Subject to any disclaimer, the term of this patent is extended or adjusted under 35 U.S.C. 154(b) by 318 days.

(21) Appl. No.: 10/706,300

(22) Filed: Nov. 12, 2003

(65) Prior Publication Data

US 2004/0127843 A1 Jul. 1, 2004

Related U.S. Application Data

(63) Continuation-in-part of application No. 10/395,633, filed on Mar. 21, 2003, now abandoned, which is a continuation of application No. 09/549,350, filed on Apr. 14, 2000, now Pat. No. 6,638,239, application No. 10/706,300, which is a continuation-in-part of application No. 10/634,213, filed on Aug. 5, 2003, which is a continuation-in-part of application No. 10/118,578, filed on Apr. 8, 2002, now Pat. No. 7,135,009, application No. 10/706,300, which is a continuation-in-part of application No. 10/046,137, filed on Nov. 8, 2001, now abandoned.

(60) Provisional application No. 60/401,166, filed on Aug. 5, 2002, provisional application No. 60/451,226, filed on Feb. 28, 2003, provisional application No. 60/281,973, filed on Apr. 7, 2001, provisional application No. 60/281,247, filed on Apr. 3, 2001, provisional application No. 60/425,911, filed on Nov. 12, 2002, provisional application No. 60/431,918, filed on Dec. 9, 2002.

(51) Int. Cl.
*A61M 19/00* (2006.01)

(52) U.S. Cl. .............................. 604/8; 604/9; 604/264

(58) Field of Classification Search ............... 604/7–10, 604/6.16, 264–266, 27, 43, 521, 522, 93.01; 210/645; 606/106–109; 623/1.42, 4.1, 23.7, 623/23.64
See application file for complete search history.

(56) References Cited

U.S. PATENT DOCUMENTS 3,416,530 A    12/1968   Ness (Continued)

FOREIGN PATENT DOCUMENTS

AU           200072059         12/2000

(Continued)

OTHER PUBLICATIONS

Office Action (Restriction Requirement) in U.S. Appl. No. 10/889,254, filed Jul. 12, 2004, entitled Glaucoma Implant With Bi-Directional Flow, Sep. 1, 2006.

(Continued)

*Primary Examiner*—Leslie R Deak
(74) *Attorney, Agent, or Firm*—Knobbe Martens Olson & Bear LLP

(57) ABSTRACT

Devices and methods are provided for the treatment of ocular disorders. An ocular implant has a body comprising material that includes a therapeutic drug. The body has an inlet portion and an outlet portion. The inlet portion is configured to reside in an anterior chamber of an eye when the outlet portion is disposed in a physiological outflow pathway of the eye. The outlet portion has an outflow opening such that the body drains fluid from the anterior chamber to the physiological outflow pathway. One method of treating an ocular disorder involves introducing an implant comprising a therapeutic drug into the eye such that the implant drains aqueous humor into a physiological outflow pathway and the therapeutic drug reaches eye tissue.

22 Claims, 56 Drawing Sheets

U.S. PATENT DOCUMENTS

| | | |
|---|---|---|
| 3,788,327 A | 1/1974 | Donowitz et al. |
| 4,037,604 A | 7/1977 | Newkirk |
| 4,113,088 A | 9/1978 | Binkhorst |
| 4,168,697 A | 9/1979 | Cantekin |
| 4,175,563 A | 11/1979 | Arenberg et al. |
| 4,402,681 A | 9/1983 | Haas et al. |
| 4,428,746 A | 1/1984 | Mendez |
| 4,501,274 A | 2/1985 | Skjaerpe |
| 4,521,210 A * | 6/1985 | Wong ............................. 604/8 |
| 4,554,918 A * | 11/1985 | White ........................ 604/10 |
| 4,583,224 A | 4/1986 | Ishii et al. |
| 4,604,087 A | 8/1986 | Joseph |
| 4,632,842 A | 12/1986 | Karwoski et al. |
| 4,634,418 A | 1/1987 | Binder |
| 4,718,907 A | 1/1988 | Karwoski et al. |
| 4,722,724 A | 2/1988 | Schocket |
| 4,733,665 A | 3/1988 | Palmaz |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,846,172 A | 7/1989 | Berlin |
| 4,846,793 A | 7/1989 | Leonard et al. |
| 4,853,224 A | 8/1989 | Wong |
| 4,863,457 A | 9/1989 | Lee |
| 4,883,864 A | 11/1989 | Scholz |
| 4,886,488 A | 12/1989 | White |
| 4,900,300 A | 2/1990 | Lee |
| 4,936,825 A | 6/1990 | Ungerleider |
| 4,946,436 A | 8/1990 | Smith |
| 4,968,296 A | 11/1990 | Ritch et al. |
| 4,997,652 A | 3/1991 | Wong |
| 5,041,081 A | 8/1991 | Odrich |
| 5,073,163 A | 12/1991 | Lippman |
| 5,092,837 A | 3/1992 | Ritch et al. |
| 5,095,887 A | 3/1992 | Leon et al. |
| 5,098,443 A | 3/1992 | Parel et al. |
| 5,127,901 A | 7/1992 | Odrich |
| 5,129,895 A | 7/1992 | Vassiliadis et al. |
| 5,164,188 A | 11/1992 | Wong |
| 5,171,213 A | 12/1992 | Price, Jr. |
| 5,178,604 A | 1/1993 | Baerveldt et al. |
| 5,180,362 A | 1/1993 | Worst |
| 5,207,685 A | 5/1993 | Cinberg et al. |
| 5,246,451 A | 9/1993 | Trescony et al. |
| 5,290,295 A | 3/1994 | Querals et al. |
| 5,300,020 A | 4/1994 | L'Esperance, Jr. |
| 5,318,513 A | 6/1994 | Leib et al. |
| 5,334,137 A | 8/1994 | Freeman |
| 5,338,291 A | 8/1994 | Speckman et al. |
| 5,346,464 A | 9/1994 | Camras |
| 5,360,399 A | 11/1994 | Stegmann |
| 5,370,607 A | 12/1994 | Memmen |
| 5,370,641 A | 12/1994 | O'Donnell, Jr. |
| 5,372,577 A | 12/1994 | Ungerleider |
| 5,397,300 A | 3/1995 | Baerveldt et al. |
| 5,433,701 A | 7/1995 | Rubinstein |
| 5,443,505 A | 8/1995 | Wong et al. |
| 5,454,796 A | 10/1995 | Krupin |
| 5,472,440 A | 12/1995 | Beckman |
| 5,476,445 A | 12/1995 | Baerveldt et al. |
| 5,486,165 A | 1/1996 | Stegmann |
| 5,516,522 A | 5/1996 | Peyman et al. |
| 5,520,631 A | 5/1996 | Nordquist et al. |
| 5,557,453 A | 9/1996 | Schalz et al. |
| 5,558,629 A | 9/1996 | Baerveldt et al. |
| 5,558,630 A | 9/1996 | Fisher |
| 5,558,637 A | 9/1996 | Allonen et al. |
| 5,562,641 A | 10/1996 | Flomenblit et al. |
| RE35,390 E | 12/1996 | Smith |
| 5,599,534 A | 2/1997 | Himmelstein et al. |
| 5,601,094 A | 2/1997 | Reiss |
| 5,601,549 A | 2/1997 | Miyagi |
| 5,626,558 A | 5/1997 | Suson |
| 5,626,559 A | 5/1997 | Solomon |
| 5,629,008 A | 5/1997 | Lee |
| 5,639,278 A | 6/1997 | Dereume et al. |
| 5,651,783 A | 7/1997 | Reynard |
| 5,652,014 A | 7/1997 | Galin et al. |
| 5,665,114 A | 9/1997 | Weadock et al. |
| 5,670,161 A | 9/1997 | Healy et al. |
| 5,676,679 A | 10/1997 | Simon et al. |
| 5,681,275 A | 10/1997 | Ahmed |
| 5,681,323 A | 10/1997 | Arick |
| 5,702,414 A | 12/1997 | Richter et al. |
| 5,702,419 A | 12/1997 | Berry et al. |
| 5,704,907 A | 1/1998 | Nordquist et al. |
| 5,713,844 A | 2/1998 | Peyman |
| 5,723,005 A | 3/1998 | Herrick |
| 5,741,333 A | 4/1998 | Frid |
| 5,743,868 A | 4/1998 | Brown et al. |
| 5,752,928 A | 5/1998 | De Roulhac et al. |
| 5,760,161 A * | 6/1998 | Goins et al. .................. 528/299 |
| 5,766,242 A | 6/1998 | Wong et al. |
| 5,766,243 A | 6/1998 | Christensen et al. |
| 5,785,674 A | 7/1998 | Mateen |
| 5,807,302 A | 9/1998 | Wandel |
| 5,810,870 A | 9/1998 | Myers et al. |
| 5,824,072 A | 10/1998 | Wong |
| 5,830,139 A | 11/1998 | Abreu |
| 5,830,171 A | 11/1998 | Wallace |
| 5,833,694 A | 11/1998 | Poncet |
| 5,836,939 A | 11/1998 | Negus et al. |
| 5,865,831 A | 2/1999 | Cozean et al. |
| 5,868,697 A | 2/1999 | Richter et al. |
| 5,869,079 A | 2/1999 | Wong et al. |
| 5,879,319 A | 3/1999 | Pynson et al. |
| 5,882,327 A | 3/1999 | Jacob |
| 5,886,822 A | 3/1999 | Spitzer |
| 5,893,837 A | 4/1999 | Eagles et al. |
| 5,908,449 A | 6/1999 | Bruchman et al. |
| 5,932,299 A | 8/1999 | Katoot |
| 5,968,058 A | 10/1999 | Richter et al. |
| 5,980,928 A * | 11/1999 | Terry .......................... 424/427 |
| 5,981,598 A | 11/1999 | Tatton |
| 6,004,302 A | 12/1999 | Brierley |
| 6,007,510 A | 12/1999 | Nigam |
| 6,007,511 A | 12/1999 | Prywes |
| 6,033,418 A | 3/2000 | Gordon et al. |
| 6,033,434 A | 3/2000 | Borghi |
| 6,045,557 A | 4/2000 | White et al. |
| 6,050,970 A | 4/2000 | Baerveldt |
| 6,050,999 A | 4/2000 | Paraschac et al. |
| 6,059,772 A | 5/2000 | Hsia et al. |
| 6,059,812 A | 5/2000 | Clerc et al. |
| 6,063,116 A | 5/2000 | Kelleher |
| 6,063,396 A | 5/2000 | Kelleher |
| 6,071,286 A | 6/2000 | Mawad |
| 6,077,299 A | 6/2000 | Adelberg et al. |
| 6,102,045 A | 8/2000 | Nordquist et al. |
| 6,142,990 A | 11/2000 | Burk |
| 6,165,210 A | 12/2000 | Lau et al. |
| 6,168,575 B1 | 1/2001 | Soltanpour |
| 6,174,305 B1 | 1/2001 | Mikus et al. |
| 6,186,974 B1 | 2/2001 | Allan et al. |
| 6,187,016 B1 | 2/2001 | Hedges et al. |
| 6,193,656 B1 | 2/2001 | Jeffries et al. |
| 6,197,056 B1 | 3/2001 | Schachar |
| 6,203,513 B1 | 3/2001 | Yaron et al. |
| 6,217,895 B1 | 4/2001 | Guo et al. |
| 6,228,873 B1 | 5/2001 | Brandt et al. |
| 6,231,597 B1 | 5/2001 | Deem et al. |
| 6,241,721 B1 | 6/2001 | Cozean et al. |
| 6,251,090 B1 | 6/2001 | Avery et al. |

| | | |
|---|---|---|
| 6,254,612 B1 | 7/2001 | Hieshima |
| 6,261,256 B1 | 7/2001 | Ahmed |
| 6,266,182 B1 | 7/2001 | Morita |
| 6,268,398 B1 | 7/2001 | Ghosh et al. |
| 6,287,313 B1 | 9/2001 | Sasso |
| 6,299,895 B1 | 10/2001 | Hammang et al. |
| 6,306,120 B1 | 10/2001 | Tan |
| 6,331,313 B1 | 12/2001 | Wong et al. |
| 6,342,058 B1 | 1/2002 | Portney |
| 6,348,042 B1 * | 2/2002 | Warren, Jr. ............. 604/8 |
| 6,375,642 B1 | 4/2002 | Grieshaber et al. |
| 6,413,540 B1 | 7/2002 | Yaacobi |
| 6,416,777 B1 | 7/2002 | Yaacobi |
| 6,428,501 B1 | 8/2002 | Reynard |
| 6,436,127 B1 | 8/2002 | Anderson et al. |
| 6,436,427 B1 | 8/2002 | Hammang et al. |
| 6,450,937 B1 | 9/2002 | Mercereau et al. |
| 6,450,984 B1 | 9/2002 | Lynch et al. |
| 6,464,724 B1 | 10/2002 | Lynch et al. |
| 6,524,275 B1 | 2/2003 | Lynch et al. |
| 6,530,896 B1 | 3/2003 | Elliott |
| 6,533,768 B1 | 3/2003 | Hill |
| 6,544,249 B1 | 4/2003 | Yu et al. |
| 6,548,078 B2 | 4/2003 | Guo et al. |
| 6,579,235 B1 | 6/2003 | Abita et al. |
| 6,585,680 B2 | 7/2003 | Bugge |
| 6,595,945 B2 | 7/2003 | Brown |
| 6,623,283 B1 | 9/2003 | Torigian et al. |
| 6,626,858 B2 | 9/2003 | Lynch et al. |
| 6,629,981 B2 | 10/2003 | Bui et al. |
| 6,638,239 B1 | 10/2003 | Bergheim et al. |
| 6,666,841 B2 | 12/2003 | Gharib et al. |
| 6,699,211 B2 | 3/2004 | Savage |
| D490,152 S | 5/2004 | Myall et al. |
| 6,736,791 B1 | 5/2004 | Tu et al. |
| 6,780,165 B2 | 8/2004 | Kadziauskas et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,955,656 B2 | 10/2005 | Bergheim et al. |
| 7,008,396 B1 * | 3/2006 | Straub ............. 604/8 |
| 7,033,603 B2 * | 4/2006 | Nelson et al. ........ 424/426 |
| 7,094,225 B2 | 8/2006 | Tu et al. |
| 7,135,009 B2 | 11/2006 | Tu et al. |
| 2002/0013546 A1 | 1/2002 | Grieshaber et al. |
| 2002/0013572 A1 | 1/2002 | Berlin |
| 2002/0026200 A1 | 2/2002 | Savage |
| 2002/0072673 A1 | 6/2002 | Yamamoto et al. |
| 2002/0099434 A1 | 7/2002 | Buscemi et al. |
| 2002/0133168 A1 | 9/2002 | Smedley et al. |
| 2002/0143284 A1 | 10/2002 | Tu et al. |
| 2002/0169130 A1 | 11/2002 | Tu et al. |
| 2002/0188308 A1 | 12/2002 | Tu et al. |
| 2003/0009124 A1 | 1/2003 | Lynch et al. |
| 2003/0055372 A1 | 3/2003 | Lynch et al. |
| 2003/0060752 A1 | 3/2003 | Bergheim et al. |
| 2003/0069637 A1 | 4/2003 | Lynch et al. |
| 2003/0088260 A1 | 5/2003 | Smedley et al. |
| 2003/0097151 A1 | 5/2003 | Smedley et al. |
| 2003/0120200 A1 | 6/2003 | Bergheim et al. |
| 2003/0181848 A1 | 9/2003 | Bergheim et al. |
| 2003/0187384 A1 | 10/2003 | Bergheim et al. |
| 2003/0187385 A1 | 10/2003 | Bergheim et al. |
| 2003/0220602 A1 | 11/2003 | Lynch et al. |
| 2003/0220603 A1 | 11/2003 | Lynch et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0050392 A1 | 3/2004 | Tu et al. |
| 2004/0092548 A1 | 5/2004 | Embleton et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0254520 A1 | 12/2004 | Porteous et al. |
| 2005/0038334 A1 | 2/2005 | Lynch et al. |
| 2005/0049578 A1 | 3/2005 | Tu et al. |
| 2005/0119737 A1 * | 6/2005 | Bene et al. ........... 623/4.1 |
| 2005/0192527 A1 | 9/2005 | Gharib et al. |

FOREIGN PATENT DOCUMENTS

| | | |
|---|---|---|
| CA | 2244646 | 8/1998 |
| DE | 198 40 047 | 2/1998 |
| DE | 198 40 047 | 3/2000 |
| EP | 0 858 788 | 8/1998 |
| EP | 0 898 947 | 3/1999 |
| EP | 1 114 627 | 11/2001 |
| FR | 2 710 269 | 9/1993 |
| FR | 93 11476 | 3/1995 |
| FR | 2 721 499 | 12/1995 |
| GB | 2 296 663 | 3/1995 |
| GB | 2 296 663 | 7/1996 |
| JP | 11-123205 | 5/1999 |
| WO | WO 89/00869 | 2/1989 |
| WO | WO 91/18568 | 12/1991 |
| WO | WO 92/19294 | 11/1992 |
| WO | WO 94/13234 | 6/1994 |
| WO | WO 94/21205 | 9/1994 |
| WO | WO 95/08310 | 3/1995 |
| WO | WO 98/30181 | 1/1998 |
| WO | WO 98/30181 | 7/1998 |
| WO | WO 98/35639 | 8/1998 |
| WO | WO 99/26567 | 6/1999 |
| WO | WO 99/30641 | 6/1999 |
| WO | WO 99/38470 | 8/1999 |
| WO | WO 00/13627 | 3/2000 |
| WO | WO 00/64389 | 4/2000 |
| WO | WO 00/64390 | 4/2000 |
| WO | WO 00/64391 | 4/2000 |
| WO | WO 00/64389 | 11/2000 |
| WO | WO 00/64390 | 11/2000 |
| WO | WO 00/64391 | 11/2000 |
| WO | WO 00/64393 | 11/2000 |
| WO | WO 00/72788 | 12/2000 |
| WO | WO 01/50943 | 7/2001 |
| WO | WO/01/50943 | 7/2001 |
| WO | WO 01/78631 | 10/2001 |
| WO | WO 01/78656 | 10/2001 |
| WO | WO 01/97727 | 12/2001 |
| WO | WO 03/015659 | 2/2003 |
| WO | WO 03/073968 | 9/2003 |

OTHER PUBLICATIONS

Office Action in U.S. Appl. No. 10/889,254, filed Jul. 12, 2004, entitled Glaucoma Implant With Bi-Directional Flow, Jan. 17, 2007.

Office Action (Final) in U.S. Appl. No. 10/889,254, filed Jul. 12, 2004, entitled Glaucoma Implant With Bi-Directional Flow, Aug. 6, 2007.

Office Action in U.S. Appl. No. 10/889,254, filed Jul. 12, 2004, entitled Glaucoma Implant With Bi-Directional Flow, Nov. 23, 2007.

Office Action in U.S. Appl. No. 11/126,868, filed May 11, 2005, entitled Injectable Gel Implant for Glaucoma Treatment, Jul. 16, 2007.

Office Action in U.S. Appl. No. 11/294,794, filed Dec. 6, 2005, entitled Shunt Device and Method for Treating Glaucoma, Aug. 14, 2007.

Office Action in U.S. Appl. No. 11/295,066, filed Dec. 6, 2005, entitled Shunt Device and Method for Treating Glaucoma, Jul. 30, 2007.

Office Action in U.S. Appl. No. 09/847,523, filed May 2, 2001, now U.S. Patent No. 6,666,841, entitled Bifurcatable Trabecular Shunt for Glaucoma Treatment, Oct. 22, 2002.

Office Action (Notices of Allowability and Allowance) in U.S. Appl. No. 09/847,523, filed May 2, 2001, now U.S. Patent No. 6,666,841, entitled Bifurcatable Trabecular Shunt for Glaucoma Treatment, May 30, 2003.

Office Action (Notice of Drawing Inconsistency with Specification) in U.S. Appl. No. 09/847,523, filed May 2, 2001, now U.S. Patent No. 6,666,841, entitled Bifurcatable Trabecular Shunt for Glaucoma Treatment, Sep. 30, 2003.

Office Action (Response to Rule 312 Communication) in U.S. Appl. No. 09/847,523, filed May 2, 2001, now U.S. Patent No. 6,666,841, entitled Bifurcatable Trabecular Shunt for Glaucoma Treatment, Nov. 7, 2003.

Office Action (Restriction Requirement) in U.S. Appl. No. 10/046,137, filed Nov. 18, 2001, entitled Drug Releasing Trabecular Implant for Glaucoma Treatment, Apr. 28, 2004.

Office Action in U.S. Appl. No. 10/046,137, filed Nov. 18, 2001, entitled Drug Releasing Trabecular Implant for Glaucoma Treatment, Aug. 25, 2004.

Office Action (Restriction Requirement) in U.S. Appl. No. 11/598,542, filed Nov. 13, 2006, entitled Implants and Methods Thereof for Treatment of Ocular Disorders, Feb. 1, 2008.

Office Action in U.S. Appl. No. 11/083,713, filed Mar. 18, 2005, entitled Glaucoma Implants With Anchors, May 15, 2007.

Office Action (Final) in U.S. Appl. No. 11/083,713, filed Mar. 18, 2005, entitled Glaucoma Implants With Anchors, Sep. 7, 2007.

Office Action in U.S. Appl. No. 11/083,713, filed Mar. 18, 2005, entitled Glaucoma Implants With Anchors, Dec. 28, 2007.

Office Action (Restriction Requirement) in U.S. Appl. No. 10/139,800, filed May 3, 2002, now U.S. Patent No. 7,094,225, entitled Medical Device and Methods of Use for Glaucoma Treatment, Jun. 21, 2004.

Office Action in U.S. Appl. No. 10/139,800, filed May 3, 2002 now U.S. Patent No. 7,094,225, entitled Medical Device and Methods of Use for Glaucoma Treatment, Oct. 4, 2004.

Office Action (Notices of Allowability and Allowance) in U.S. Appl. No. 10/139,800, filed May 3, 2002, now U.S. Patent No. 7,094,225, entitled Medical Device and Methods of Use for Glaucoma Treatment, May 23, 2005.

Office Action (Miscellaneous Communication) in U.S. Appl. No. 10/139,800, filed May 3, 2002, now U.S. Patent No. 7,094,225, entitled Medical Device and Methods of Use for Glaucoma Treatment, May 12, 2006.

Office Action in U.S. Appl. No. 11/255,625, filed Oct. 21, 2005, now U.S. Patent No. 7,273,475, entitled Medical Device and Methods of Use for Glaucoma Treatment, Feb. 14, 2007.

Office Action (Notices of Allowability and Allowance) in U.S. Appl. No. 11/255,625, filed Oct. 21, 2005, now U.S. Patent No. 7,273,475, entitled Medical Device and Methods of Use for Glaucoma Treatment, May 21, 2007.

Office Action in U.S. Appl. No. 10/395,646, filed Mar. 21, 2003, entitled Expandable Glaucoma Implant and Methods of Use, Aug. 30, 2004.

Office Action (Response to Amendment) in U.S. Appl. No. 10/395,646, filed Mar. 21, 2003, entitled Expandable Glaucoma Implant and Methods of Use, Apr. 18, 2005.

Office Action (Final) in U.S. Appl. No. 10/395,646, filed Mar. 21, 2003, entitled Expandable Glaucoma Implant and Methods of Use, Aug. 4, 2005.

Office Action in U.S. Appl. No. 10/395,646, filed Mar. 21, 2003, entitled Expandable Glaucoma Implant and Methods of Use, Mar. 6, 2006.

Office Action in U.S. Appl. No. 10/384,912, filed Mar. 7, 2003, now U.S. Patent No. 7,186,232, entitled Fluid Infusion Methods for Glaucoma Treatment, Aug. 25, 2004.

Office Action (Final) in U.S. Appl. No. 10/384,912, filed Mar. 7, 2003, now U.S. Patent No. 7,186,232, entitled Fluid Infusion Methods for Glaucoma Treatment, May 4, 2005.

Office Action in U.S. Appl. No. 10/384,912, filed Mar. 7, 2003, now U.S. Patent No. 7,186,232, entitled Fluid Infusion Methods for Glaucoma Treatment, Sep. 7, 2005.

Office Action (Notices of Allowability and Allowance) in U.S. Appl. No. 10/384,912, filed Mar. 7, 2003, now U.S. Patent No. 7,186,232, entitled Fluid Infusion Methods for Glaucoma Treatment, Dec. 21, 2005.

Office Action (Notices of Allowability and Allowance) in U.S. Appl. No. 10/384,912, filed Mar. 7, 2003, now U.S. Patent No. 7,186,232, entitled Fluid Infusion Methods for Glaucoma Treatment, Sep. 27, 2006.

Office Action in U.S. Appl. No. 11/332,746, filed Jan. 12, 2006, entitled Fluid Infusion Methods for Glaucoma Treatment, Dec. 14, 2007.

Office Action in U.S. Appl. No. 11/353,854, filed Feb. 13, 2006, entitled Liquid Jet for Glaucoma Treatment, Oct. 10, 2006.

Office Action (Final) in U.S. Appl. No. 11/353,854, filed Feb. 13, 2006, entitled Liquid Jet for Glaucoma Treatment, Jul. 9, 2007.

Office Action in U.S. Appl. No. 10/409,028, filed Apr. 7, 2003, entitled Drug-Releasing Implant for Optic Nerve Protection, Mar. 23, 2006.

Office Action in U.S. Appl. No. 10/420,354, filed Apr. 18, 2003, entitled Glaucoma Implant With Valveless Flow Bias, Jun. 15, 2005.

Office Action (Final) in U.S. Appl. No. 10/420,354, filed Apr. 18, 2003, entitled Glaucoma Implant With Valveless Flow Bias, Nov. 8, 2005.

Office Action (Advisory Action) in U.S. Appl. No. 10/420,354, filed Apr. 18, 2003, entitled Glaucoma Implant With Valveless Flow Bias, Jan. 20, 2006.

Office Action in U.S. Appl. No. 10/420,354, filed Apr. 18, 2003, entitled Glaucoma Implant With Valveless Flow Bias, Apr. 19, 2006.

Office Action (Interview Summary) in U.S. Appl. No. 10/420,354, filed Apr. 18, 2003, entitled Glaucoma Implant With Valveless Flow Bias, Aug. 3, 2006.

Office Action in U.S. Appl. No. 10/420,354, filed Apr. 18, 2003, entitled Glaucoma Implant With Valveless Flow Bias, Aug. 6, 2007.

Office Action (Final) in U.S. Appl. No. 10/420,354, filed Apr. 18, 2003, entitled Glaucoma Implant With Valveless Flow Bias, Oct. 16, 2006.

Office Action in U.S. Appl. No. 10/683,767, filed Oct. 10, 2003, entitled Liquid Jet Trabeculotomy, Nov. 17, 2006.

Office Action (Final) in U.S. Appl. No. 10/683,767, filed Oct. 10, 2003, entitled Liquid Jet Trabeculotomy, Aug. 13, 2007.

Office Action (Advisory Action) in U.S. Appl. No. 10/683,767, filed Oct. 10, 2003, entitled Liquid Jet Trabeculotomy, Nov. 9, 2007.

Office Action (Restriction Requirement) in U.S. Appl. No. 10/763,569, filed Jan. 23, 2004, entitled Vasomodulation During Glaucoma Surgery, Oct. 11, 2006.

Office Action in U.S. Appl. No. 10/763,569, filed Jan. 23, 2004, entitled Vasomodulation During Glaucoma Surgery, Feb. 22, 2007.

Office Action (Restriction Requirement) in U.S. Appl. No. 11/286,779, filed Nov. 22, 2005, entitled Ophthalmology Implant and Methods of Manufacture, Sep. 27, 2007.

Troncoso, Manuel U., Tantalum implants for inducing hypotony, American Journal of Ophthalmology, vol. 32, No. 4, Apr. 1949, pp. 499-508 (11 pages).

Wagner, Justin A., Edwards, Aurélie, and Schuman, Joel S., Characterization of Uveoscleral Outflow in Enucleated Porcine Eyes Perfused Under Constant Pressure, *Invest Ophthalmol Vis Sci.* Sep. 2004; 45(9): 3203-3206 (9 pages).

Office Action (Restriction Requirement) in U.S. Appl. No. 10/889,254, filed Jul. 12, 2004, entitled Ocular Implant With Anchor and Therapeutic Agent, Sep. 1, 2006.

Office Action in U.S. Appl. No. 10/889,254, filed Jul. 12, 2004, entitled Ocular Implant With Anchor and Therapeutic Agent, Jan. 17, 2007.

Office Action (Final) in U.S. Appl. No. 10/889,254, filed Jul. 12, 2004, entitled Ocular Implant With Anchor and Therapeutic Agent, Aug. 6, 2007.

Office Action in U.S. Appl. No. 10/889,254, filed Jul. 12, 2004, entitled Ocular Implant With Anchor and Therapeutic Agent, Nov. 23, 2007.

Office Action (Interview Summary) in U.S. Appl. No. 10/889,254, filed Jul. 12, 2004, entitled Ocular Implant With Anchor and Therapeutic Agent, Jun. 2, 2008.

Office Action (Final) in U.S. Appl. No. 10/889,254, filed Jul. 12, 2004, entitled Ocular Implant With Anchor and Therapeutic Agent, Aug. 18, 2008.

Office Action in U.S. Appl. No. 10/889,254, filed Jul. 12, 2004, entitled Ocular Implant With Anchor and Therapeutic Agent, Apr. 13, 2009.

Office Action in U.S. Appl. No. 11/332,746, filed Jan. 12, 2006, entitled Fluid Infusion Methods for Ocular Disorder Treatment, Dec. 14, 2007.

Office Action (Final) in U.S. Appl. No. 11/332,746, filed Jan. 12, 2006, entitled Fluid Infusion Methods for Ocular Disorder Treatment, Aug. 1, 2008.

Office Action (Interview Summary) in U.S. Appl. No. 11/332,746, filed Jan. 12, 2006, entitled Fluid Infusion Methods for Ocular Disorder Treatment, Dec. 11, 2008.

Office Action in U.S. Appl. No. 11/332,746, filed Jan. 12, 2006, entitled Fluid Infusion Methods for Ocular Disorder Treatment, Mar. 27, 2009.

Hyuncheol Kim et al., "Controlled Drug Release from an Ocular Implant: an Evaluation Using Dynamic Three-Dimensional Magnetic Resonance Imaging," *Investigative Ophthalmology & Visual Science*, Aug. 2004, vol. 45, No. 8, pp. 2722-2731.

Detlev Spiegel, *7 Chirurgische Glaukomtherapie*, pp. 79-88, 2008.

Anselm Kampik and Franz Grehn, *Nutzen und Risiken augenärztlicher Therapie, Hauptreferate der XXXIII. Essener Fortbildung für Augenärzte*, Dec. 1998. (English translated version enclosed Benefits and Risks of Ophthalmological Therapy.).

Phillip C. Jacobi, MD, Thomas S. Dietlein, MD, and Gunter K. Krieglstein, MD., *Goniocurettage for Removing Trabecular Meshwork: Clinical Results of a New Surgical Technique in Advanced Cronic Open-Angle Glaucoma*, American Journal of Ophthalmology, May 1999, pp. 505-510.

Philip C. Jacobi, MD, Thomas S. Dietlein, MD, and Gunter K. Krieglstein, MD., Bimanual Trabecular Aspiration in Pseudoexfoliation Glaucoma, *Ophthalmology*, 1998, vol. 105, No. 5, May 1998, pp. 886-894.

Phillip C. Jacobi, MD, Thomas S. Dietlein, MD, and Gunter K. Krieglstein, MD., Microendoscopic Trabecular Surgery in Glaucoma Management, *Ophthalmology*, 1999, vol. 106, No. 3, pp. 538-544.

Arthur L. Schwartz, MD, and Douglas R. Anderson, MD, *Trabecular Surgery*, Arch Ophthalmol, vol. 92, Aug. 1974, pp. 134-138.

R.A. Hill, Q. Ren, D.D. Nguyen, L-H Liaw, and M.W. Berns, *Free-Electron Laser (FEL) Ablation of Ocular Tissues*, Lasesr Med Sci 1998, pp. 13:219-226.

Maurice H. Luntz, MD, and D.G. Livingston, B.SC., *Trabeculotomy AB Externo and Trabeculectomy in Congenital and Adult-Onset Glaucoma*, American Journal of Ophthalmology, Feb. 1977, vol. 83, No. 2, pp. 174-179.

W.M. Grant, MD, *Further Studies on Facility of Flow Through the Trabecular Meshwork*, A.M.A. Archives of Ophthalmololgy, Oct. 1958, vol. 60, pp. 523-533.

Richard A. Hill, MD, George Baerveldt, MD, Serdar A. Ozler, MD, Michael Pickford, BA, Glen A. Profeta, BS, and Michael W. Berns,PhD, *Laser Trabecular Ablation (LTA)*, Laser in Surgery and Medicine, 1991, vol. 11, pp. 341-346.

Detlev Spiegel, MD, Karin Kobuch, MD, Richard A. Hill, MD, Ronald L. Gross, MD, *Schlemm's Canal Implant: A New Method to Lower Intraocular Pressure in Patients With POAG*, Ophthalmic Surgery and Lasers, Jun. 1999, vol. 30, No. 6, pp. 492-494.

Hans Hoerauf, Christopher Wirbelauer, Christian Scholz, Ralf Engelhardt, Peter Koch, Horst Laqua, and Reginald Birngruber, *Slit-Lamp-Adapted Optical Coherence Tomography of the Anteriuor Segment*, Graefe's Arch Clin. Exp. Ophthalmol, May 1999, vol. 238, pp. 8-18.

Sumita Radhakrishnan, Andrew M. Rollins, Jonathan E. Roth, S. Yazddanfar, Volker Westphal, David Bardenstein, and Joseph Izatt, *Real-Time Optical Coherence Tomography of the Anterior Segment at 1310 nm*, Arch Ophthalmology, Aug. 2001, vol. 119, pp. 1179-1185.

I. Grierson, R.C. Howes, and Q. Wang, *Age-related Changes in the Canal of Schlemm*, Exp. Eye Res., 1984, vol. 39, pp. 505-512.

Luanna K. Putney, Cecile Rose T. Vibat, and Martha E. O'Donnell, *Intracellular Cl Regulates Na-K-Cl Cotransport Activity in Human Trabecular Meshwork Cells*, 1999 American Physiological Society, Sep. 1999, pp. C373 through C383.

Edited by Kevin Strange, *Cellular and Molecular Physiology of Cell Volume Regulation*, Library of Congress Cataloging in-Publication Data, CRC Press, Inc., pp. 312-321, 1994.

William Tatton, Ruth M.E. Chalmers-Redman, Ajay Sud, Steven M. Podos, and Thomas Mittag, *Maintaining Mitochondrial Membrane Impermeability: An Opportunity for New Therapy in Glaucoma*, Survey of Ophthalmology, vol. 45, Supplement 3, May 2001, pp. S277 through S283.

Robert W. Nickells, *Apoptosis of Retinal Ganglion Cells in Glaucoma: An Update of the Molecular Pathways Involved in Cell Death*, Survey of Ophthalmology, vol. 43, Supplement 1, Jun. 1999, pp. S-151 through S-161.

Grune & Stratton, Harcourt Brace Jovanovich Publishers, edited by J.E. Cairns, *Glaucoma*, vol. 1, Chapter 14, Anatomy of the Aqueous Outflow Channels, by Johannes W. Rohen, pp. 277-296, 1986.

Yasuhiro Matsumoto and Douglas H. Johnson, *Trabecular Meshwork Phagocytosis in Graucomatous Eyes*, Ophthalmologica 1977, vol. 211, pp. 147-152.

M. Bruce Shields, MD, *A Study Guide for Glaucoma: Aqueous Humor Dynamics*, Copyright 1982, pp. 6-43.

M.A. Johnstone, R. Stegmann, and B.A. Smit, American Glaucoma Society, 12th Annual Meeting, *Cylindrical Tubular Structures Spanning from Trabecular Meshwork Across SC*, Laboratory Studies with SEM, TEM and Tracers Correlated with Clinical Findings, p. 39, Feb. 2002.

W.G. Tatton, *Apoptotic Mechanisms in Neurodegeneration: Possible Relevance to Glaucoma*, European Journal of Ophthalmology, Jan.-Mar. 1999, vol. 9, Supplement 1, pp. S22 through S29.

L. Jay Katz, M.D., *A Call for Innovative Operations for Glaucoma*, Arch Ophthalmology, Mar. 2000, vol. 118, pp. 412-413.

Cindy K. Bahler, BS, Gegrory T. Smedley, PhD, Jianbo Zhou, PhD, Douglas H. Johnson, MD., *American Journal of Ophthalmology*, Dec. 2004, vol. 138.

Jianbo Zhou, PhD, Gregory T. Smedley, PhD., *A Trabecular Bypass Flow Hypothesis*, Feb. 2005, vol. 14 No. 1.

U.S. Appl. No. 09/452,963, filed Dec. 2, 1999. Title: *Expandable/Retractable Stent for Venous and Valvular Annulus Use*.

Vincente, L. Jocson, M.D.; *Air Trabeculotomy*; American Journal of Ophthalmolgy: vol. 79, No. 1, Jan.-Jun. 1975; pp. 107-111.

Daniel A. Fletcher, Ph.D., Daniel V. Palanker, Ph.D., Philip Hule, M.D., Jason Miller, MS, Michael F. Marmor, M.D. and Mark S. Blumenkranz, M.D.; *Intravascular Drug Delivery With a Pulsed Liquid Microjet*; (Reprinted) Arch Ophthalmology; vol. 120, Sep. 2002, pp. 1206-1208.

Jacobi et al., *Goniocurettage for Removing Trabecular Meshwork: Clinical Results of a New Surgical Technique in Advanced Chronic Open-Angle Glaucoma*, American Journal of Ophtoalmology, May 1999, vol. 127, No. 5, pp. 505-510.

Jacobi et al., *Bimanual Trabecular Aspiration in Pseudoexfoliation Glaucoma: An Alternative in Nonfiltering Glaucoma Surgery*, American Journal of Ophthalmology, May 1998, vol. 105, No. 5, pp. 886-894.

Jacobi et al., *Microendoscopic Travecular Surgery in Glaucoma Management*, American Journal of Ophtoalmology, Mar. 1999, vol. 106, No. 3, pp. 538-544.

Schwartz et al., *Trabecular Surgery*, Arch. Ophthalmol, Aug. 1974, vol. 92, pp. 134-138.

Hill et al., *Free-Electron Laser (FEL) Ablation of Ocular Tissues*, Lasers Med Sci, 1998, vol. 13, pp. 219-226.

Luntz et al., *Traveculotomy AB Externo and Trabeculectomy in Congenital and Adult-Onset Glaucoma*, American Journal of Ophthalmology, Feb. 1977, vol. 83, No. 2, pp. 174-179.

W. M. Grant, *Further Studies on Facility of Flow Through the Trabecular.Meshwork*, AMA Archives of Ophthalmology, Oct. 1958, vol. 60, pp. 523-533.

Hill et al., *Laser Trabecular Ablation (LTA)*, Lasers in Surgery and Medicine, 1991, vol. 11, pp. 341-346.

Spiegel et al., *Schlemm's Canal Implant: A New Method to Lower Intraocular Pressure in Patients With POAG?*, Ophthalmic Surgery and Lasers, Jun. 1999, vol. 30, No. 6, pp. 492-494.

L.J. Katz, *A Call for Innovative Operations for Glaucoma*, Arch. Ophthalmol, Mar. 2000, vol. 118, pp. 412-413.

Detlev Spiegel, *Benefits and Risks of Ophthalmological Therapy: 7 Surgical Glaucoma Therapy*, Main Presentataions at the XXXIII Continuing Education for Ophthalmologists in Essen (Germany), published Dec. 1998.

Hoerauf et al., *Slit-lamp-adapted optical coherence tomography of the anterior segment*, Graefe's Arch Clin Exp Ophthalmol (2000), vol. 237, pp. 8-18.

Radhakrishnan et al., *Real-Time Optical Coherence Tomography of the Anterior Segment at 1310 nm*, Arch Ophthalmol, Aug. 2002, vol. 119, pp. 1179-1185.

Grierson et al., *Age-related Changes in the Canal of Schlemm*, Eye Res. (1984) vol. 39, pp. 505-512.

Putney et al., *Intracellular Cl regulates Na-K-Cl cotransport activity in human trabecular meshwork cells*, American Journal of Physiology, Sep. 1999, vol. 277, pp. C373-383.

K. Strange, *Cellular and Molecular Physiology of Cell Volume Regulation*, CTC Press, Inc: 1994, pp. 311-321.

Tatton et al., *Maintaining Mitochondrial Membrane Impermeability: An opportunity for New Therapy in Glaucoma?*, Survey of Ophthalmology May 2001, vol. 45, Supplement 3, pp. S277-283.

R.W. Nickells, *Apoptosis of Retinal Ganglion Cells in Glaucoma: An Update of the Molecular Pathways Involved in Cell Death*, Survey of Ophthalmology Jun. 1999, vol. 43, Supplement 1, pp. S151-161.

J.W. Rohen, *Anatomy of the aqueous outflow channels*, Glaucoma: vol. 1, Grune & Stratton: 1986. pp. 277-296.

Matsumoto et al., *Trabecular Meshwork Phagocytosis in Glaucomatous Eyes*, Ophthalmologica 1997, vol. 211, pp. 147-152.

M. B. Shields, *A Study Guide for Glaucoma*, Williams & Wilkins: 1982, pp. 6-43.

Johnstone et al., *Cylindrical Tubular Structures Spanning from Trabecular Meshwork Across SC: Laboratory Studies With SEM, TEM & Tracers Correlated with Clinical Findings*, Abstract Paper No. 18. p. 39 from American Glaucoma Society 12th Annual Meeting Feb. 2002.

W.G. Tatton, *Apoptotic mechanisms in neurodegeneration: Possible relevance to glaucoma*, European Journal of Ophthalmology 1999, vol. 9, Supplement 1, pp. S22-29.

U.S. Appl. No. 09/452,963, filed Dec. 2, 1999. Title: Expandable/Retractable Stent for Venous and Valvular Annulus Use.

\* cited by examiner

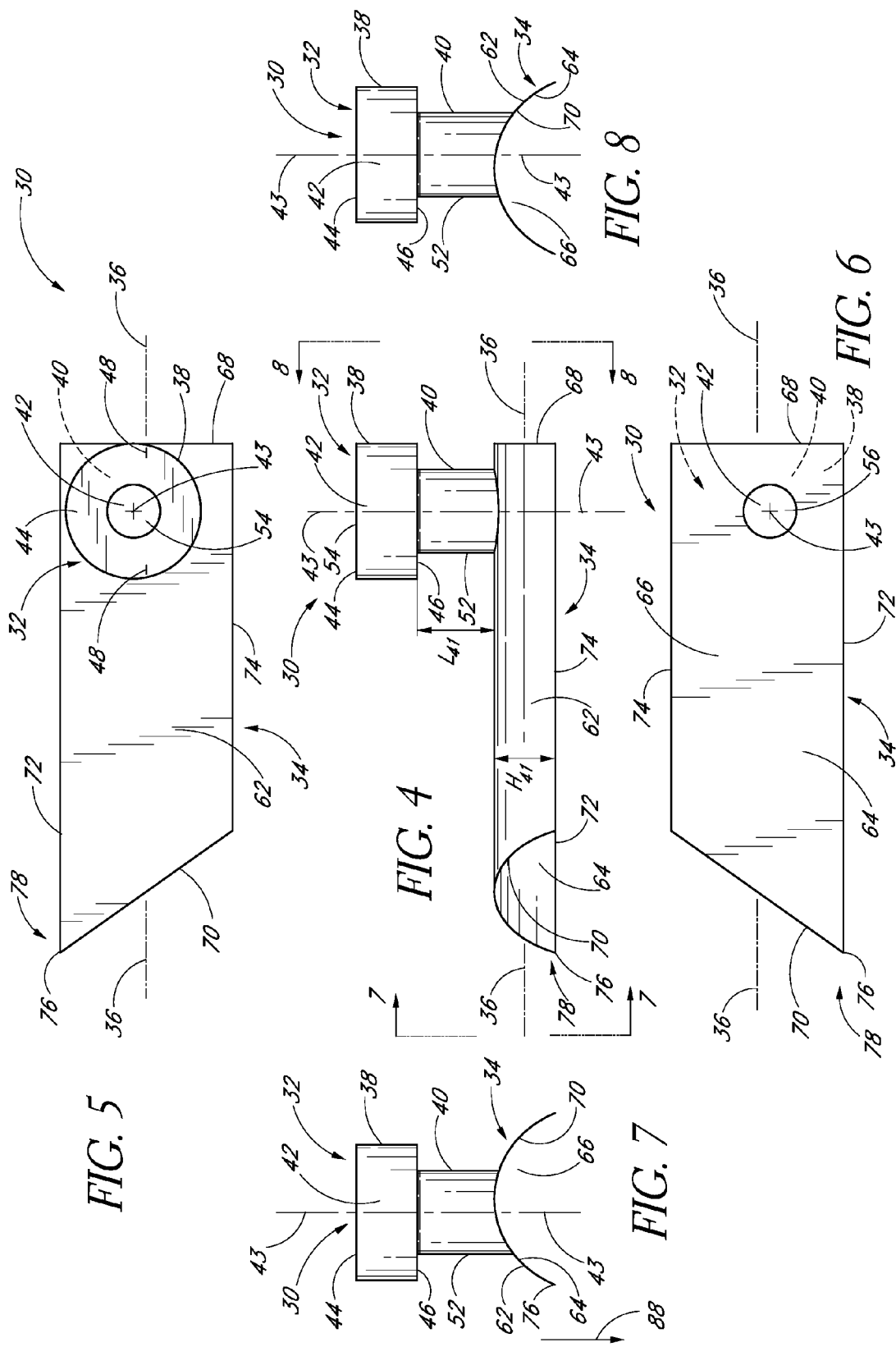

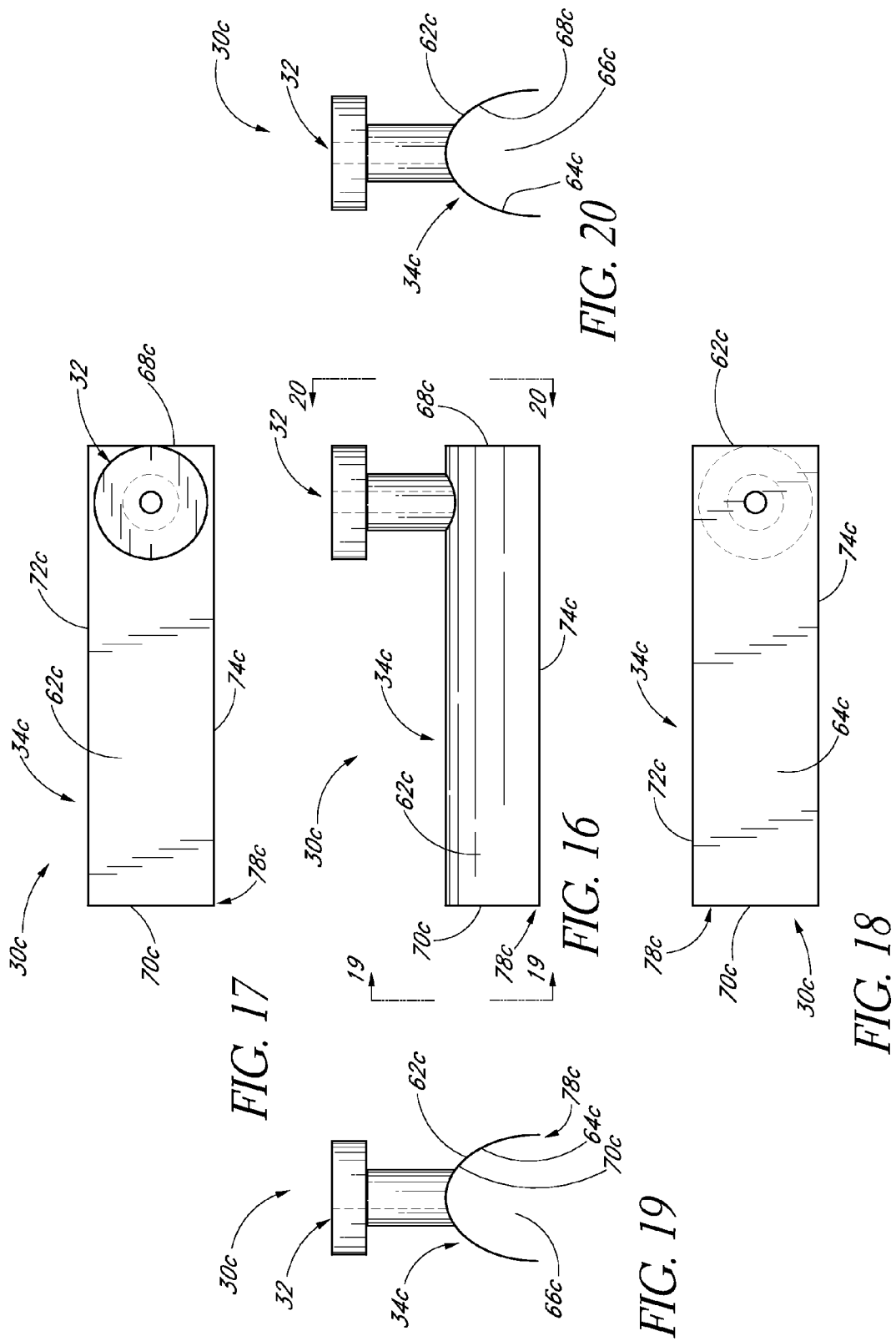

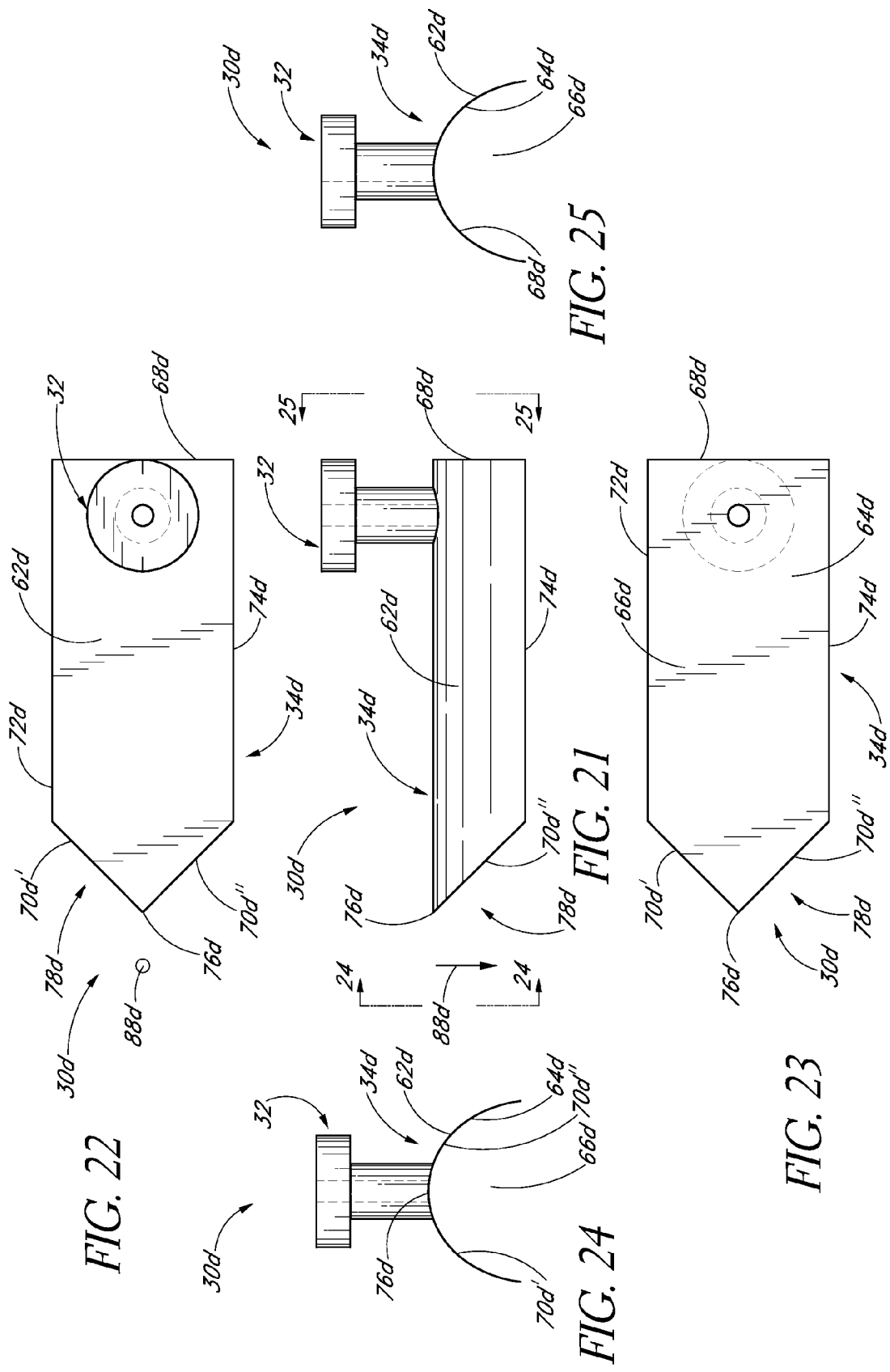

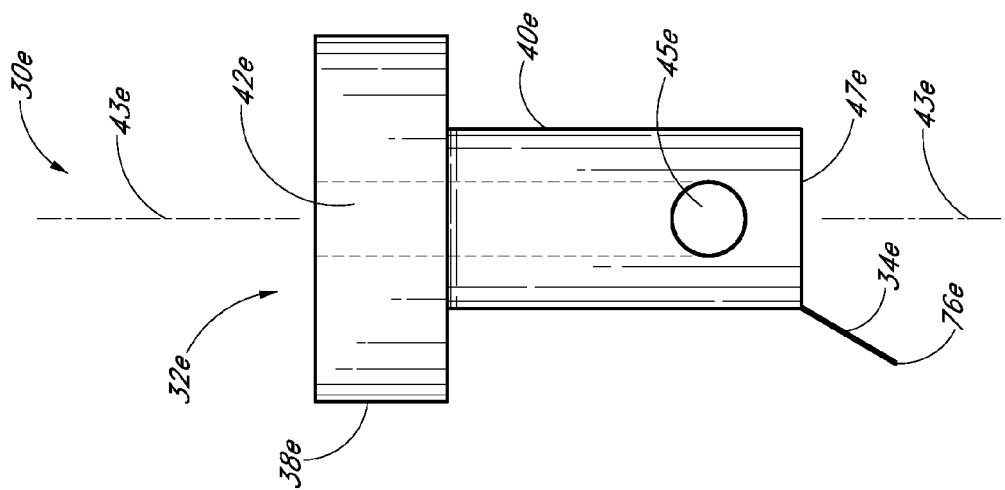
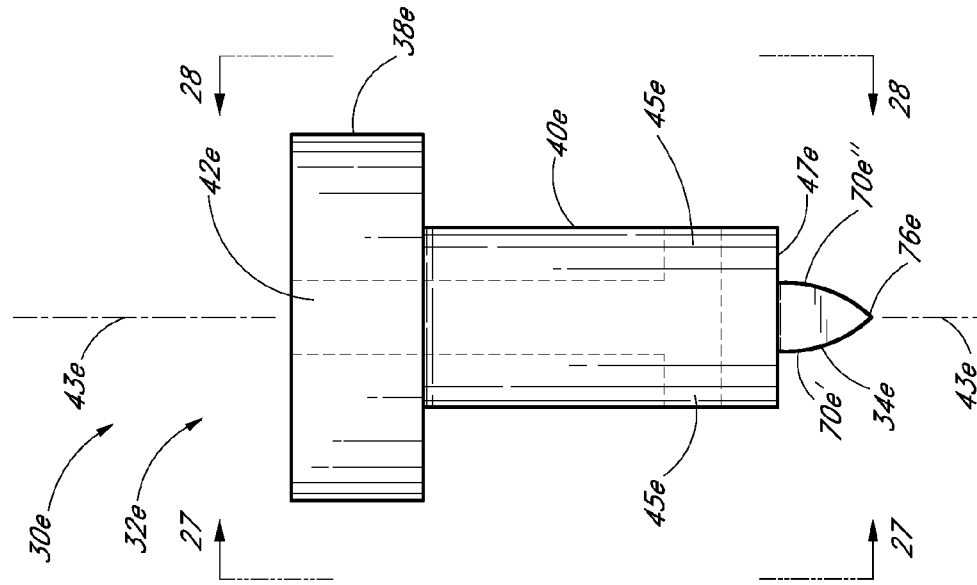
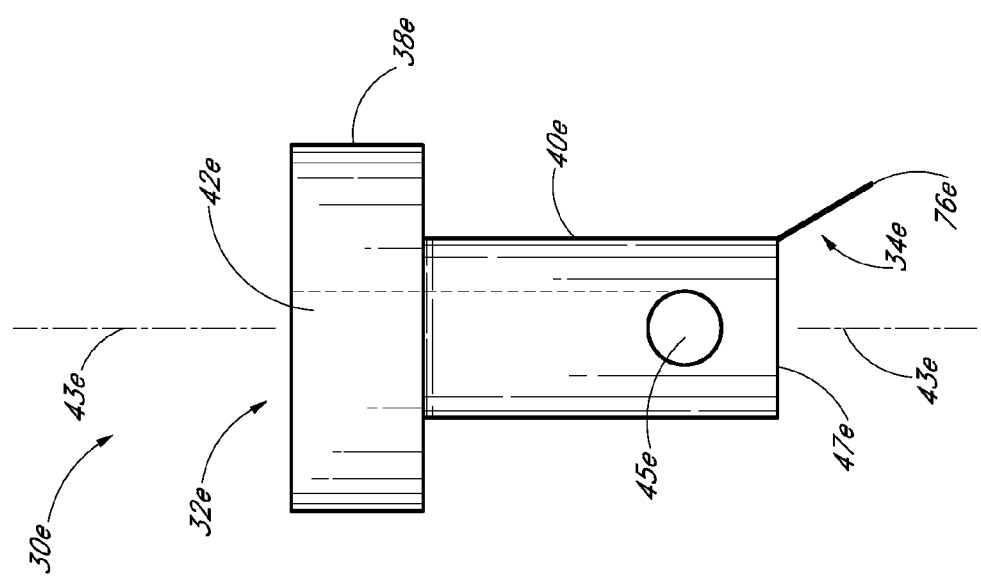

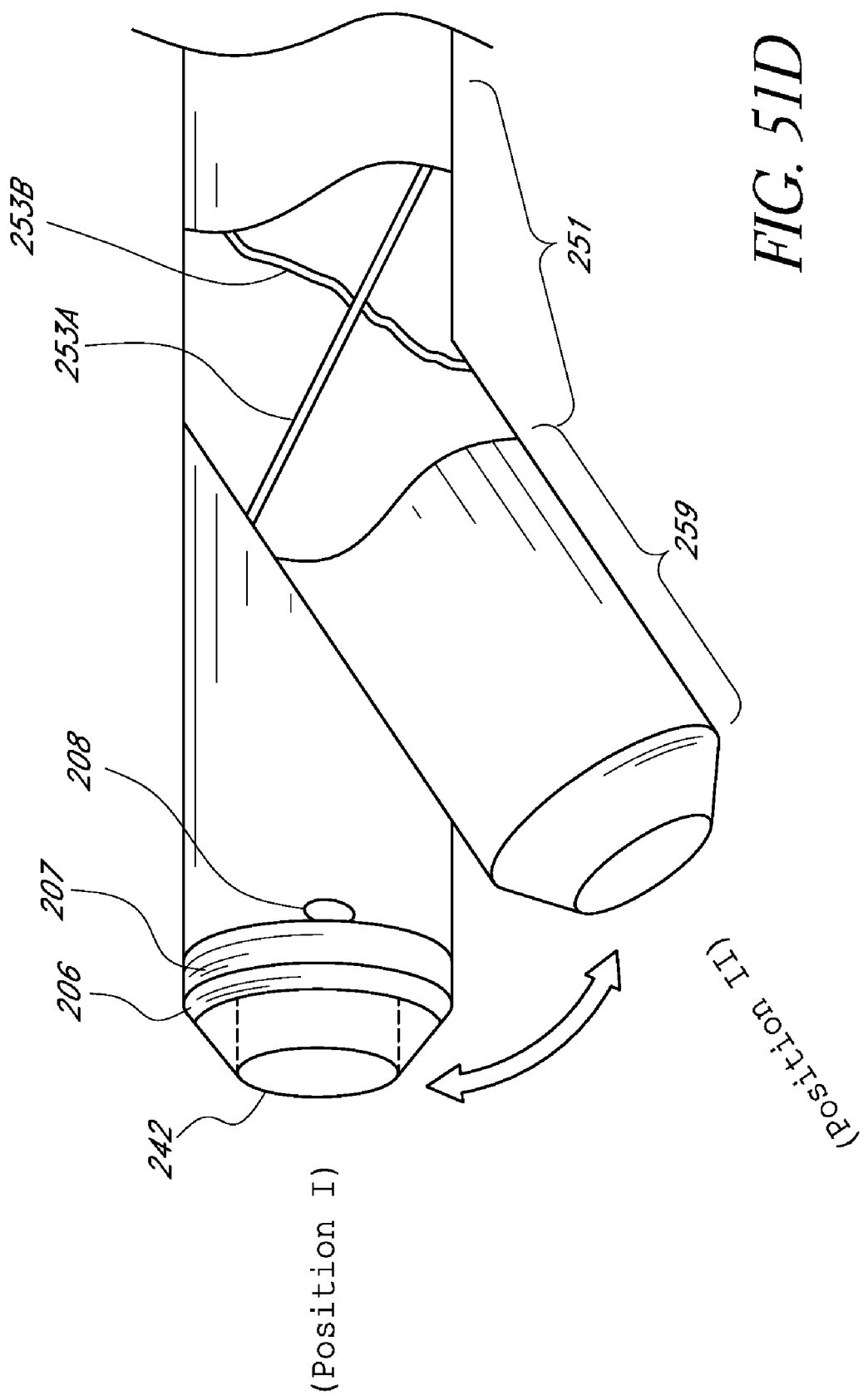

OCULAR IMPLANT WITH THERAPEUTIC AGENTS AND METHODS THEREOF

CROSS REFERENCE TO RELATED APPLICATIONS

This application is a continuation-in-part of U.S. patent application Ser. No. 10/395,633, filed Mar. 21, 2003, now abandoned entitled "Stent With Drug Coating," which is a continuation application of U.S. patent application Ser. No. 09/549,350, filed Apr. 14, 2000, now U.S. Pat. No. 6,638,239 B1, issued Oct. 28, 2003, entitled "Apparatus And Method For Treating Glaucoma".

This application is also a continuation-in-part of U.S. patent application Ser. No. 10/634,213, filed Aug. 5, 2003, entitled "Devices And Methods For Glaucoma Treatment," which is a continuation-in-part of U.S. patent application Ser. No. 10/118,578, filed Apr. 8, 2002, now U.S. Pat. No. 7,135,009 B2, issued Nov. 14, 2006, entitled "Glaucoma Stent And Methods Thereof For Glaucoma Treatment," which claims the priority benefit of U.S. Provisional Application No. 60/281,973, filed Apr. 7, 2001. The aforementioned U.S. patent application Ser. No. 10/634,213 also claims the priority benefits of U.S. Provisional Application No. 60/401,166, filed Aug. 5, 2002, and U.S. Provisional Application No. 60/451,226, filed Feb. 28, 2003.

This application is also a continuation-in-part of U.S. patent application Ser. No. 10/046,137, filed Nov. 8, 2001, now abandoned, entitled "Drug-Releasing Trabecular Implant for Glaucoma Treatment," which claims the priority benefit of U.S. Provisional Application No. 60/281,247, filed Apr. 3, 2001.

This application also claims the priority benefits of U.S. Provisional Patent Application No. 60/425,911, filed Nov. 12, 2002, and U.S. Provisional Patent Application No. 60/431,918, filed Dec. 9, 2002.

The entireties of all of the aforementioned priority documents are hereby incorporated by reference.

BACKGROUND OF THE INVENTION

1. Field of the Invention

The present application relates generally to medical devices and methods for reducing the intraocular pressure in an animal eye and, more particularly, to shunt-type stenting devices for permitting and/or enhancing aqueous outflow from the eye's anterior chamber toward existing outflow pathways and associated methods thereof for the treatment of glaucoma in general. Furthermore, the invention relates to the delivery of bioactive agents to ocular tissue from an implant.

2. Description of the Related Art

The human eye is a specialized sensory organ capable of light reception and able to receive visual images. The trabecular meshwork serves as a drainage channel and is located in the anterior chamber angle formed between the iris and the cornea. The trabecular meshwork maintains a balanced pressure in the anterior chamber of the eye by allowing aqueous humor to flow from the anterior chamber.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is a major treatment goal in all glaucomas.

In glaucomas associated with an elevation in eye pressure (intraocular hypertension), the source of resistance to outflow of aqueous humor is mainly in the trabecular meshwork. The tissue of the trabecular meshwork allows the aqueous humor ("aqueous") to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is an essentially constant flow of aqueous humor from the ciliary body to the eye's anterior chamber. The anterior chamber pressure is determined by a balance between the production of aqueous and its exit through the trabecular meshwork (major route) or uveal scleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Glaucoma is grossly classified into two categories: closed-angle glaucoma, also known as "angle closure" glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye.

Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas that may include edema or swelling of the trabecular spaces (e.g., from corticosteroid use), abnormal pigment dispersion, or diseases such as hyperthyroidism that produce vascular congestion.

Current therapies for glaucoma are directed at decreasing intraocular pressure. Medical therapy includes topical ophthalmic drops or oral medications that reduce the production or increase the outflow of aqueous. However, these drug therapies for glaucoma are sometimes associated with significant side effects, such as headache, blurred vision, allergic reactions, death from cardiopulmonary complications, and potential interactions with other drugs. When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if the morbidity associated with trabeculectomy could be decreased. The current morbidity associated with trabeculectomy consists of failure (10-15%); infection (a life long risk of 2-5%); choroidal hemorrhage, a severe internal hemorrhage from low intraocular pressure, resulting in visual loss (1%); cataract formation; and hypotony maculopathy (potentially reversible visual loss from low intraocular pressure).

For these reasons, surgeons have tried for decades to develop a workable surgery for the trabecular meshwork.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the opening created in the trabecular meshwork. Once the openings close, the pressure builds back up and the surgery fails.

Trabeculopuncture: Q-switched Neodymium (Nd) YAG lasers also have been investigated as an optically invasive technique for creating full-thickness holes in trabecular meshwork. However, the relatively small hole created by this trabeculopuncture technique exhibits a filling-in effect and fails.

Goniophotoablation/Laser Trabecular Ablation: Goniophotoablation is disclosed by Berlin in U.S. Pat. No. 4,846,172 and involves the use of an excimer laser to treat glaucoma by ablating the trabecular meshwork. This was demonstrated not to succeed by clinical trial. Hill et al. disclosed the use of an Erbium:YAG laser to create full-thickness holes through trabecular meshwork (Hill et al., Lasers in Surgery and Medicine 11:341-346, 1991). This technique was investigated in a primate model and a limited human clinical trial at the University of California, Irvine. Although morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage: This is an ab interno (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanalostomy (VC) and non-penetrating trabeculectomy (NPT) are two new variations of filtering surgery. These are ab externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous humor is drained onto the surface of the eye or into the tissues located within the lateral wall of the eye. These surgical operations are major procedures with significant ocular morbidity. Where trabeculectomy, VC, and NPT were thought to have a low chance for success in particular cases, a number of implantable drainage devices have been used to ensure that the desired filtration and outflow of aqueous humor through the surgical opening will continue. The risk of placing a glaucoma drainage device also includes hemorrhage, infection, and diplopia (double vision).

All of the above surgeries and variations thereof have numerous disadvantages and moderate success rates. They involve substantial trauma to the eye and require great surgical skill in creating a hole through the full thickness of the sclera into the subconjunctival space. The procedures are generally performed in an operating room and have a prolonged recovery time for vision.

The complications of existing filtration surgery have prompted ophthalmic surgeons to find other approaches to lowering intraocular pressure or treating tissue of trabecular meshwork.

The trabecular meshwork and juxtacanilicular tissue together provide the majority of resistance to the outflow of aqueous and, as such, are logical targets for tissue stimulation/rejuvenating or shunting in the treatment of open-angle glaucoma. In addition, minimal amounts of tissue are displaced and functions of the existing physiologic outflow pathways are restored.

As reported in Arch. Ophthalm. (2000) 118:412, glaucoma remains a leading cause of blindness, and filtration surgery remains an effective, important option in controlling the disease. However, modifying existing filtering surgery techniques in any profound way to increase their effectiveness appears to have reached a dead end. The article further states that the time has come to search for new surgical approaches that may provide better and safer care for patients with glaucoma.

Examples of implantable shunts and surgical methods for maintaining an opening for the release of aqueous from the anterior chamber of the eye to the sclera or space beneath the conjunctiva have been disclosed in, for example, Hsia et al., U.S. Pat. No. 6,059,772 and Baerveldt, U.S. Pat. No. 6,050,970.

Examples of implantable shunts or devices for maintaining an opening for the release of aqueous humor from the anterior chamber of the eye to the sclera or space underneath conjunctiva have been disclosed in U.S. Pat. Nos. 6,007,511 (Prywes), 6,007,510 (Nigam), 5,893,837 (Eagles et al.), 5,882,327 (Jacob), 5,879,319 (Pynson et al.), 5,807,302 (Wandel), 5,752,928 (de Roulhac et al.), 5,743,868 (Brown et al.), 5,704,907 (Nordquist et al.), 5,626,559 (Solomon), 5,626,558 (Suson), 5,601,094 (Reiss), RE. 35,390 (Smith), 5,558,630 (Fisher), 5,558,629 (Baerveldt et al.), 5,520,631 (Nordquist et al.), 5,476,445 (Baerveldt et al.), 5,454,796 (Krupin), 5,433,701 (Rubinstein), 5,397,300 (Baerveldt et al.), 5,372,577 (Ungerleider), 5,370,607 (Memmen), 5,338,291 (Speckman et al.), 5,300,020 (L'Esperance, Jr.), 5,178,604 (Baerveldt et al.), 5,171,213 (Price, Jr.), 5,041,081 (Odrich), 4,968,296 (Ritch et al.), 4,936,825 (Ungerleider), 4,886,488 (White), 4,750,901 (Molteno), 4,634,418 (Binder), 4,604,087 (Joseph), 4,554,918 (White), 4,521,210 (Wong), 4,428,746 (Mendez), 4,402,681 (Haas et al.), 4,175,563 (Arenberg et al.), and 4,037,604 (Newkirk).

All of the above embodiments and variations thereof have numerous disadvantages and moderate success rates. They involve substantial trauma to the eye and require great surgical skill in creating a hole through the full thickness of the sclera into the subconjunctival space. The procedures are generally performed in an operating room and involve a prolonged recovery time for vision. The complications of existing filtration surgery have prompted ophthalmic surgeons to find other approaches to lowering intraocular pressure.

Because the trabecular meshwork and juxtacanilicular tissue together provide the majority of resistance to the outflow of aqueous, they are logical targets for surgical removal in the treatment of open-angle glaucoma. In addition, minimal amounts of tissue need be altered and existing physiologic outflow pathways can be utilized.

SUMMARY OF THE INVENTION

What is needed, therefore, is an extended, site-specific treatment method for glaucoma that is faster, safer, and less expensive than currently available modalities. There is a great clinical need for an improved method of treating glaucoma that is faster, safer, and less expensive than currently available drug or surgical modalities. The methods disclosed herein include ab interno and ab externo procedures that involve non-flap operations. The method herein may further comprise using an innovative stenting device.

In some preferred embodiments, the seton has an inlet portion configured to extend through a portion of the trabecular meshwork of an eye, and an outlet portion configured to extend into Schlemm's canal of the eye, wherein the inlet portion is disposed at an angle relative to the outlet portion. In some embodiments, the outlet portion has a lumen with an oval cross-section having a long axis.

The outlet portion in certain embodiments has a longitudinal axis, such that the long axis of the oval cross-section and the longitudinal axis of the outlet portion define a plane, the inlet portion having a longitudinal axis that lies outside the plane at an angle θ (theta) thereto.

In some preferred arrangements, the seton comprises an inlet portion, configured to extend through a portion of the trabecular meshwork; an outlet portion, configured to extend into Schlemm's canal; and at least one protrusion on the outlet portion, configured to exert traction against an inner surface of Schlemm's canal. This protrusion can comprise at least one barb or ridge.

Some preferred embodiments comprise an inlet portion configured to extend through a portion of the trabecular meshwork, an outlet portion configured to extend into Schlemm's canal, and a one-way valve within the inlet and/or outlet portions.

A method for delivering a seton within an eye is disclosed, comprising providing an elongate guide member, advancing a distal end of the guide member through at least a portion of the trabecular meshwork of the eye, advancing the seton along the guide member toward the distal end, and positioning the seton to conduct aqueous humor between the anterior chamber of the eye and Schlemm's canal.

In certain embodiments, the advancing of the guide member comprises advancing it from the anterior chamber into the trabecular meshwork. In further embodiments, the positioning comprises positioning an end of the seton within Schlemm's canal adjacent to an aqueous collection channel.

Certain preferred embodiments include an apparatus for delivering a seton to the anterior chamber of an eye comprising an elongate tube having a lumen, an outer surface, and a distal end; a removable, elongate guide member within the lumen, configured to permit the seton to be advanced to and be positioned in the trabecular meshwork of the eye. This apparatus can further comprise a cutting member positioned at the distal end of the tube. The cutting member can be selected from the group consisting of a knife, a laser probe, a pointed guide member, a sharpened distal end of said tube, and an ultrasonic cutter. The apparatus can also further comprise an opening in the outer surface of the tube, configured to allow fluid infusion into the eye.

In further preferred embodiments, an apparatus for delivering a seton in an eye, comprises an elongate member adapted for insertion into an anterior chamber of the eye, the elongate member having a distal end portion configured to retain the seton therein, the distal end portion comprising a cutting member configured to form an opening in the trabecular meshwork of the eye for receipt of the seton, such that one end of the seton is in Schlemm's canal. The elongate member can further comprise a lumen that conducts fluid toward said distal end portion.

The preferred embodiment provides further surgical treatment of glaucoma (trabecular bypass surgery) at the level of trabecular meshwork and restores existing physiological outflow pathways. An implant bypasses diseased trabecular meshwork at the level of trabecular meshwork and which restores existing physiological outflow pathways. The implant has an inlet end, an outlet end and a lumen therebetween. The inlet is positioned in the anterior chamber at the level of the internal trabecular meshwork and the outlet end is positioned at about the exterior surface of the diseased trabecular meshwork and/or into fluid collection channels of the existing outflow pathways.

In accordance with a preferred method, trabecular bypass surgery creates an opening or a hole through the diseased trabecular meshwork through minor microsurgery. To prevent "filling in" of the hole, a biocompatible elongated implant is placed within the hole as a seton, which may include, for example, a solid rod or hollow tube. In one exemplary embodiment, the seton implant may be positioned across the diseased trabecular meshwork alone and it does not extend into the eye wall or sclera. In another embodiment, the inlet end of the implant is exposed to the anterior chamber of the eye while the outlet end is positioned at the exterior surface of the trabecular meshwork. In another exemplary embodiment, the outlet end is positioned at and over the exterior surface of the trabecular meshwork and into the fluid collection channels of the existing outflow pathways. In still another embodiment, the outlet end is positioned in the Schlemm's canal. In an alternative embodiment, the outlet end enters into fluid collection channels up to the level of the aqueous veins with the seton inserted in a retrograde or antegrade fashion.

According to the preferred embodiment, the seton implant is made of biocompatible material, which is either hollow to allow the flow of aqueous humor or solid biocompatible material that imbibes aqueous. The material for the seton may be selected from the group consisting of porous material, semi-rigid material, soft material, hydrophilic material, hydrophobic material, hydrogel, elastic material, and the like.

In further accordance with the preferred embodiment, the seton implant may be rigid or it may be made of relatively soft material and is somewhat curved at its distal section to fit into the existing physiological outflow pathways, such as Schlemm's canal. The distal section inside the outflow pathways may have an oval shape to stabilize the seton in place without undue suturing. Stabilization or retention of the seton may be further strengthened by a taper end and/or by at least one ridge or rib on the exterior surface of the distal section of the seton, or other surface alterations designed to retain the seton.

In one embodiment, the seton may include a micropump, one-way valve, or semi-permeable membrane if reflux of red blood cells or serum protein becomes a clinical problem. It may also be useful to use a biocompatible material that hydrates and expands after implantation so that the seton is locked into position around the trabecular meshwork opening or around the distal section of the seton.

One of the advantages of trabecular bypass surgery, as disclosed herein, and the use of a seton implant to bypass diseased trabecular meshwork at the level of trabecular meshwork and thereby use existing outflow pathways is that the treatment of glaucoma is substantially simpler than in existing therapies. A further advantage of the invention is the utilization of simple microsurgery that may be performed on an outpatient basis with rapid visual recovery and greatly decreased morbidity. Finally, a distinctly different approach is used than is found in existing implants. Physiological outflow mechanisms are used or re-established by the implant of the present invention, in contradistinction with previously disclosed methodologies.

A device and method are provided for improved treatment of intraocular pressure due to glaucoma. A trabecular shunting and stenting device is adapted for implantation within a trabecular meshwork of an eye such that aqueous humor flows controllably from an anterior chamber of the eye to Schlemm's canal, bypassing the trabecular meshwork. The trabecular stenting device comprises a quantity of bioactive agents effective in treating glaucoma, which are controllably released from the device into cells of the trabecular meshwork and/or Schlemm's canal. Depending upon the specific treatment contemplated, bioactive agents may be utilized in conjunction with the trabecular stenting device such that aqueous flow either increases or decreases as desired. Placement of the trabecular stenting device within the eye and incorporation, and eventual release, of a proven bioactive agents glaucoma therapy will reduce, inhibit or slow the effects of glaucoma.

One aspect of the invention provides a trabecular stenting device that is implantable within an eye. The device comprises an inlet section containing at least one lumen, an outlet section having at least one outlet end. In one embodiment, there provides a flow-restricting member within the lumen that is configured to prevent at least one component of blood from passing through the flow-restricting member. In another embodiment, the device further comprises a middle section having at least one lumen. The middle section is fixedly attached between the inlet section and the outlet section and the lumen is in fluid communication with the lumens of the inlet and outlet sections. The device is configured to permit fluid entering the lumens of the inlet section, the middle section, and the outlet section, and then exit the outlet section through the at least one outlet end.

Another aspect of the invention provides a method of treating glaucoma. The method comprises providing at least one bioactive agent or substance incorporated into a trabecular stenting device, implanting the trabecular stenting device within a trabecular meshwork of an eye such that a first end of the trabecular stent is positioned in an anterior chamber of the eye while a second end is positioned in a Schlemm's canal, and allowing the stenting device to release a quantity of the bioactive agent into the eye. The first and second ends of the trabecular stenting device establish a fluid communication between the anterior chamber and the Schlemm's canal.

In another aspect of the invention, the bioactive agent comprises genes, growth factors, TGF-beta, scar inhibitors, and the like.

Still another aspect of the invention provides a method of regulating intraocular pressure within an eye. The method comprises: providing at least one bioactive agent incorporated into a trabecular stenting device; implanting the trabecular stenting device within a trabecular meshwork of an eye such that a first end of the trabecular stent is positioned in an anterior chamber of the eye while a second end is positioned in a Schlemm's canal, wherein the first and second ends of the trabecular stenting device establish a fluid communication between the anterior chamber and the Schlemm's canal; and allowing the stenting device to release a quantity of said bioactive agent into the eye.

Another aspect of the invention provides an apparatus for implanting a trabecular shunting/stenting device within an eye. The apparatus comprises a syringe portion and a cannula portion that has proximal and distal ends. The proximal end of the cannula portion is attached to the syringe portion. The cannula portion further comprises a first lumen and at least one irrigating hole disposed between the proximal and distal ends of the cannula portion. The irrigating hole is in fluid communication with the lumen. The apparatus further includes a holder comprising a second lumen for holding the trabecular stenting device. A distal end of the second lumen opens to the distal end of the cannula portion, and a proximal end of the second lumen is separated from the first lumen of the cannula portion. The holder holds the trabecular stenting device during implantation of the device within the eye, and the holder releases the trabecular stenting device when a practitioner activates deployment of the device.

Another aspect of the invention provides a method of implanting a trabecular stenting device within an eye. The method comprises creating a first incision in a cornea on a first side of the eye, wherein the first incision passes through the cornea into an anterior chamber of the eye. The method further comprises passing an incising device through the first incision and moving a distal end of the incising device across the anterior chamber to a trabecular meshwork residing on a second side of the eye, and using the incising device to create a second incision. The second incision is in the trabecular meshwork, passing from the anterior chamber through the trabecular meshwork into a Schlemm's canal. The method further comprises inserting the trabecular shunting/stenting device into a distal space of a delivery applicator. The method further comprises advancing the cannula portion having the trabecular stenting device through the first incision, across the anterior chamber and into the second incision, wherein an outlet section of the trabecular stenting device is implanted into Schlemm's canal while an inlet section of the trabecular stenting device remains in fluid communication with the anterior chamber. The method still further comprises releasing the trabecular stenting device from the holder of the delivery applicator.

The trabecular meshwork and juxtacanilicular tissue together provide the majority of resistance to the outflow of aqueous and, as such, are logical targets for the treatment of glaucoma. Various embodiments of glaucoma devices and methods are disclosed herein for treating glaucoma by an ab interno procedure or an ab externo procedure, with respect to trabecular meshwork. The "ab interno" procedure is herein intended to mean any procedure that creates an opening from the anterior chamber through trabecular meshwork outwardly toward Schlemm's canal or toward scleral/cornea wall. This ab interno procedure may be initiated through the scleral wall or cornea wall into the anterior chamber as a first step. The "ab externo" procedure is herein intended to mean any procedure that creates an opening on the scleral wall through trabecular meshwork inwardly toward the anterior chamber. In most "ab externo" procedures disclosed herein, an instrument is passed through or contacts Schlemm's canal before entering trabecular meshwork and approaching the anterior chamber. The trabecular meshwork can generally be said to be bordered on one side by the anterior chamber and on the other side by Schlemm's canal.

Glaucoma surgical morbidity would greatly decrease if one were to bypass the focal resistance to outflow of aqueous only at the point of resistance, and to utilize remaining, healthy aqueous outflow mechanisms. This is in part because episcleral aqueous humor exerts a backpressure that prevents intraocular pressure from falling too low, and one could thereby avoid hypotony. Thus, such a surgery would virtually eliminate the risk of hypotony-related maculopathy and choroidal hemorrhage. Furthermore, visual recovery would be very rapid, and the risk of infection would be very small, reflecting a reduction in incidence from 2-5% to about 0.05%.

Copending U.S. application Ser. No. 09/549,350, filed Apr. 14, 2000, entitled APPARATUS AND METHOD FOR TREATING GLAUCOMA, and copending U.S. application Ser. No. 09/704,276, filed Nov. 1, 2000, entitled GLAUCOMA TREATMENT DEVICE, disclose devices and methods of placing a trabecular shunt ab interno, i.e., from inside the anterior chamber through the trabecular meshwork, into Schlemm's canal. The entire contents of each one of these copending patent applications are hereby incorporated by reference herein. This application encompasses both ab interno and ab externo glaucoma shunts or stents and methods thereof.

One technique performed in accordance with certain aspects herein can be referred to generally as "trabecular bypass surgery." Advantages of this type of surgery include lowering intraocular pressure in a manner that is simple, effective, disease site-specific, and can potentially be performed on an outpatient basis.

Generally, trabecular bypass surgery (TBS) creates an opening, a slit, or a hole through trabecular meshwork with minor microsurgery. TBS has the advantage of a much lower risk of choroidal hemorrhage and infection than prior techniques, and it uses existing physiologic outflow mechanisms. In some aspects, this surgery can potentially be performed under topical or local anesthesia on an outpatient basis with rapid visual recovery. To prevent "filling in" of the hole, a biocompatible elongated hollow device is placed within the hole and serves as a stent. U.S. patent application Ser. No. 09/549,350, filed Apr. 14, 2000 and the corresponding WO PCT US 01/07398 filed Mar. 8, 2001, the entire contents of which are hereby incorporated by reference herein, disclose trabecular bypass surgery in details.

As described in U.S. patent application Ser. No. 09/549,350, filed Apr. 14, 2000, and U.S. application Ser. No. 09/704,276, filed Nov. 1, 2000, a trabecular shunt or stent for transporting aqueous humor is provided. The trabecular stent includes a hollow, elongate tubular element, having an inlet section and an outlet section. The outlet section may optionally include two segments or elements, adapted to be positioned and stabilized inside Schlemm's canal. In one embodiment, the device appears as a "T" or an "L" shaped device.

In accordance with one aspect of at least one of the inventions disclosed herein, a delivery apparatus (or "applicator") is used for placing a trabecular stent through a trabecular meshwork of an eye. Certain embodiments of such a delivery apparatus are disclosed in copending U.S. application Ser. No. 10/101,548, filed Mar. 18, 2002, entitled APPLICATOR AND METHODS FOR PLACING A TRABECULAR SHUNT FOR GLAUCOMA TREATMENT, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein.

The stent has an inlet section and an outlet section. The delivery apparatus includes a handpiece, an elongate tip, a holder and an actuator. The handpiece has a distal end and a proximal end. The elongate tip is connected to the distal end of the handpiece. The elongate tip has a distal portion and is configured to be placed through a corneal incision and into an anterior chamber of the eye. The holder is attached to the distal portion of the elongate tip. The holder is configured to hold and release the inlet section of the trabecular stent. The actuator is on the handpiece and actuates the holder to release the inlet section of the trabecular stent from the holder. When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger.

Some aspects of at least one of the inventions disclosed herein relate to devices for reducing intraocular pressure by providing outflow of aqueous from an anterior chamber of an eye. The device generally comprises an elongated tubular member and cutting means. The tubular member is adapted for extending through a trabecular meshwork of the eye. The tubular member generally comprises a lumen having an inlet port and at least one outlet port for providing a flow pathway. The cutting means is mechanically connected to or is an integral part of the tubular member for creating an incision in the trabecular meshwork for receiving at least a portion of the tubular member.

In one embodiment, a self-trephining glaucoma stent is provided for reducing and/or balancing intraocular pressure in an eye. The stent generally comprises a snorkel and a curved blade. The snorkel generally comprises an upper seat for stabilizing said stent within the eye, a shank and a lumen. The shank is mechanically connected to the seat and is adapted for extending through a trabecular meshwork of the eye. The lumen extends through the snorkel and has at least one inlet flow port and at least one outlet flow port. The blade is mechanically connected to the snorkel. The blade generally comprises a cutting tip proximate a distal-most point of the blade for making an incision in the trabecular meshwork for receiving the shank.

Some aspects of at least one of the inventions disclosed herein relate to methods of implanting a trabecular stent device in an eye. In one embodiment, the device has a snorkel mechanically connected to a blade. The blade is advanced through a trabecular meshwork of the eye to cut the trabecular meshwork and form an incision therein. At least a portion of the snorkel is inserted in the incision to implant the device in the eye.

Some aspects provide a self-trephining glaucoma stent and methods thereof, which advantageously allow for a "one-step" procedure in which the incision and placement of the stent are accomplished by a single device and operation. This desirably allows for a faster, safer, and less expensive surgical procedure. In any of the embodiments, fiducial markings, indicia, or the like and/or positioning of the stent device in a preloaded applicator may be used for proper orientation and alignment of the device during implantation.

Among the advantages of trabecular bypass surgery is its simplicity. The microsurgery may potentially be performed on an outpatient basis with rapid visual recovery and greatly decreased morbidity. There is a lower risk of infection and choroidal hemorrhage, and there is a faster recovery, than with previous techniques.

Some aspects of at least one of the inventions disclosed herein relate to a medical device system for treating glaucoma of an eye comprising using OCT (optical coherence tomography) as an imaging and locating system for trabecular stent placement. In one embodiment, the procedure would first be set up with triangulation or some means to reliably establish the implant location in x, y, and z coordinates by using OCT within a few microns, most preferably in a non-invasive, non-contact manner. Having acquired the target space or location, the trabecular stent device would then be injected into place either via an ab interno procedure or an ab externo procedure. An article by Hoerauf et al. (Greafe's Arch Clin Exp Ophthalmol 2000; 238:8-18 published by Springer-Verlag), entire contents of which are incorporated herein by reference, discloses a slit-lamp adapted optical coherence tomography of the anterior segment.

Some aspects of at least one of the inventions disclosed herein relate to a 'foldable' stent wherein the size of the stent is reduced in order to place it through a yet smaller ocular entrance wound, as small as half or less than the size of the unfolded stent. The smallest size wound is important to aid in recovery, to prevent complications, and to minimize the preparation and extent of the surgical environment. In another embodiment, the device is positioned through the trabecular meshwork in an ab externo or ab interno procedure. Reliable visualization (OCT, UBM, gonioscope, electromagnetic or other means) is a key enabler for micro precision surgery such as a trabecular bypass surgery using a microstent.

Some aspects of at least one of the inventions disclosed herein relate to a medical device system with trephining capability, wherein a cutting mechanism is on or as part of the applicator for purposes of making the hole in trabecular meshwork for stent insertion. In one aspect, a cutting tip may protrude through the lumen of the stent. In another, the tip extends down the side of the snorkel without entering the lumen. In still another, the tip either passes through the lumen or down the side and further extends to the tip of the stent that is the leading edge during insertion. In one embodiment, the cutting tip can be designed to retract after making the incision but before insertion of the stent into Schlemm's canal if it interferes with the insertion operation. It could also be retracted after insertion of the stent into Schlemm's canal.

Some aspects of at least one of the inventions disclosed herein provide an implant for treating glaucoma, the implant having a longitudinal implant axis, and comprising an outflow portion through which a portion of the longitudinal implant axis passes, the outflow portion shaped and sized to be (a) introduced into Schlemm's canal with the portion of the longitudinal implant axis at an angle to Schlemm's canal; and (b) received with Schlemm's canal regardless of the rotational orientation of the outflow portion about the portion of the longitudinal implant axis during the introduction; and an inflow portion in fluid communication with the outflow portion, the inflow portion configured to permit communication of fluid from the anterior chamber of the eye to the outflow portion.

Some aspects of at least one of the inventions disclosed herein provide an implant for treating glaucoma, comprising: an outflow portion, sized and shaped to be received within Schlemm's canal, the outflow portion comprising: an outflow portion base having an outflow opening and at least one standoff member disposed to space the outflow opening from a wall of Schlemm's canal, such that the opening is unobstructed by the canal wall.

Some aspects of at least one of the inventions disclosed herein provide an implant for treating glaucoma, the implant having a longitudinal implant axis and comprising: a first portion at a first end of the longitudinal implant axis, the first portion sized and configured to reside in Schlemm's canal, such that the first portion has a maximum dimension along a longitudinal axis of Schlemm's canal that is not substantially greater than a dimension of the first portion that runs perpendicular to both the longitudinal axis of Schlemm's canal and to the longitudinal implant axis; and a second portion at a second end of the longitudinal implant axis, the second portion configured to provide fluid communication between the anterior chamber and the first portion.

Some aspects of at least one of the inventions disclosed herein provide an implant for treating glaucoma, comprising: an outflow portion, sized and shaped to be received within Schlemm's canal; an inflow portion in fluid communication with the outflow portion, the inflow portion configured to be disposed in the anterior chamber of the eye; and a central portion extending between the inflow and outflow portions; the outflow portion having a diameter that is no more than three times the diameter of the central portion.

In accordance with one embodiment of at least one of the inventions disclosed herein, an implant for treating glaucoma is provided. The implant includes a longitudinal implant axis, and comprises an outflow portion through which said longitudinal implant axis passes. The outflow portion is shaped and sized to be introduced into Schlemm's canal with the portion of the longitudinal implant axis at an angle to Schlemm's canal. The outflow portion is also shaped and sized to be received within Schlemm's canal regardless of a rotational orientation of the outflow portion about said longitudinal implant axis during said introduction. The implant also comprises an inflow portion configured to permit communication of fluid from the anterior chamber of the eye to the outflow portion.

In accordance with another embodiment of at least one of the inventions disclosed herein, an implant for treating glaucoma is provided. The implant comprises an outflow portion, sized and shaped to be received within Schlemm's canal. The outflow portion comprises an outflow portion base having an outflow opening and at least one standoff member disposed to space said outflow opening from a wall of Schlemm's canal, such that said outflow opening is unobstructed by said canal wall.

In accordance with a further embodiment of at least one of the inventions disclosed herein, an implant for treating glaucoma is provided. The implant includes a longitudinal implant axis and comprises a first portion at a first end of said longitudinal implant axis. The first portion is sized and configured to reside in Schlemm's canal, such that said first portion has a maximum dimension along a longitudinal axis of Schlemm's canal that is not substantially greater than a dimension of the first portion that runs perpendicular to both said longitudinal axis of Schlemm's canal and to said longitudinal implant axis. A second portion at a second end of said longitudinal implant axis is configured to provide fluid communication between the anterior chamber and said first portion.

In accordance with yet another embodiment of at least one of the inventions disclosed herein, an implant for treating glaucoma comprises an outflow portion, sized and shaped to be received within Schlemm's canal. An inflow portion is in fluid communication with said outflow portion, the inflow portion configured to be disposed in the anterior chamber of the eye. A central portion extending between the inflow and outflow portions. The outflow portion having a diameter that is no more than three times the diameter of the central portion.

In accordance with yet another embodiment of at least one of the inventions disclosed herein, an instrument for delivering implants for treating an ophthalmic condition is provided. The instrument comprises an elongate body sized to be introduced into an eye through an incision in the eye. A plurality of implants is positioned in the elongate body. The elongate body further comprises an actuator that serially dispenses the implants from the elongate body for implanting in eye tissue.

In accordance with another embodiment of at least one of the inventions disclosed herein, a method of implanting a plurality of implants for treating glaucoma is provided. The method includes inserting an instrument into an eye through an incision, utilizing the instrument to deliver a first implant through a wall of Schlemm's canal at a first location, and utilizing the instrument to deliver a second implant through a wall of Schlemm's canal at a second location, without removing the instrument from the eye between the deliveries of said implants.

In accordance with yet another embodiment of at least one of the inventions disclosed herein, a method of implanting a plurality of implants for treating glaucoma is provided. The method includes inserting an instrument into an eye through an incision, utilizing the instrument to deliver a first implant through a wall of Schlemm's canal at a first location, and utilizing the instrument to deliver a second implant through a wall of Schlemm's canal at a second location, wherein the locations are determined from morphological data on collector channel locations.

In accordance with yet another embodiment of at least one of the inventions disclosed herein, a method of implanting a plurality of implants for treating glaucoma is provided. The method comprises inserting an instrument into an eye through an incision, utilizing the instrument to deliver a first implant through a wall of Schlemm's canal at a first location, and utilizing said instrument to deliver a second implant through a wall of Schlemm's canal at a second location. The locations are determined by imaging collector channel locations.

In accordance with a further embodiment of at least one of the inventions disclosed herein, a method of implanting a plurality of implants for treating glaucoma is provided. The method comprises inserting an instrument into an eye through an incision, utilizing the instrument to deliver a first implant through a wall of Schlemm's canal at a first location, and utilizing said instrument to deliver a second implant through a wall of Schlemm's canal at a second location. The locations are angularly spaced along Schlemm's canal by at least 20 degrees.

In accordance with yet another embodiment of at least one of the inventions disclosed herein, a method of implanting a plurality of implants for treating glaucoma is provided. The method comprises inserting an instrument into an eye through an incision, utilizing the instrument to deliver a first implant through a wall of Schlemm's canal at a first location, utilizing the instrument to deliver a second implant through a wall of Schlemm's canal at a second location. The first and second locations are substantially at collector channels.

In accordance with another embodiment of at least one of the inventions disclosed herein, a method of implanting a plurality of implants for treating glaucoma is provided. The method comprises inserting an instrument into an eye through an incision, utilizing the instrument to deliver a first implant through a wall of Schlemm's canal at a first location, and utilizing said instrument to deliver a second implant through a wall of Schlemm's canal at a second location. The implants have different flow characteristics.

In accordance with yet another embodiment of at least one of the inventions disclosed herein, a method of implanting a plurality of implants for treating glaucoma is provided. The method comprises inserting an instrument into an eye through an incision, utilizing the instrument to deliver a first implant into the posterior segment of the eye, and utilizing the instrument to deliver a second implant into the posterior segment of the eye at a second location. The instrument is not removed from the eye between said deliveries of the implants.

In accordance with a further embodiment of at least one of the inventions disclosed herein, a method of implanting a plurality of implants for treating glaucoma is provided. The method comprises serially dispensing a plurality of preloaded implants from an instrument into eye tissue at a respective plurality of locations within the eye.

For purposes of summarizing, certain aspects, advantages and novel features of the inventions disclosed herein have been described herein above. Of course, it is to be understood that not necessarily all such advantages may be achieved in accordance with any particular embodiment. Thus, the inventions may be embodied or carried out in a manner that achieves or optimizes one advantage or group of advantages as taught or suggested herein without necessarily achieving other advantages as may be taught or suggested herein.

Some embodiments include an implant for treating glaucoma, comprising a body comprising material that includes a drug, the body having an inlet portion and an outlet portion, the inlet portion configured to transport fluid from the anterior chamber of an eye to the outlet portion when the outlet portion is disposed in Schlemm's canal of the eye, the outlet portion having an outflow opening.

In some embodiments, the body is coated with the drug. In some embodiments, the drug comprises heparin.

Some embodiments include an implant for treating glaucoma, comprising a body having a bioactive agent in or on the body, the body having an inlet portion and an outlet portion, the inlet portion configured to transmit fluid from the anterior chamber to the outlet portion when the outlet portion is disposed in Schlemm's canal, the outlet portion having an outflow opening.

In some embodiments, the bioactive agent comprises TGF-beta, a gene, an anti-inflammatory drug, and/or an intraocular pressure-lowering drug.

In some embodiments, the bioactive agent comprises a growth factor and/or an antiproliferative agent.

In some embodiments, the bioactive agent is loaded onto a surface of the outlet section.

Some embodiments further comprise a biodegradable material in or on the implant. In some embodiments, the biodegradable material is selected from the group consisting of poly(lactic acid), polyethylene-vinyl acetate, poly(lactic-co-glycolic acid), poly(D,L-lactide), poly(D,L-lactide-co-trimethylene carbonate), collagen, heparinized collagen, poly(caprolactone), poly(glycolic acid), and a copolymer.

In some embodiments, the outlet end further comprises a plurality of pillars at the outlet end. In some embodiments, the bioactive agent is in or on at least one of the pillars.

In some embodiments, the implant is at least partially coated with at least one polymer film that contains the bioactive agent, the polymer film permitting a delivery of a quantity of the bioactive agent to ocular tissues over time.

Some embodiments include an ocular implant comprising a body having a bioactive agent in or on the body, the body further comprising an inlet section configured to be positioned in the anterior chamber of an eye; an outlet section configured to be positioned at least partially in Schlemm's canal of the eye, the outlet section being in fluid communication with the inlet section; a lumen extending between the inlet section and the outlet section; and a flow-restricting member within the lumen, the flow-restricting member being configured to prevent at least one component of blood from passing through the flow-restricting member.

In some embodiments, the bioactive agent comprises an Imidazole antiproliferative agent, a quinoxaline, a phsophonylmethoxyalkyl nucleotide analog, a potassium channel blocker, and/or a synthetic oligonucleotide. In some embodiments, the bioactive agent comprises 5-[1-hydroxy-2-[2-(2-methoxyphenoxyl)ethylamino]ethyl]-2-methylbenzenesulfonamide.

In some embodiments, the bioactive agent comprises a guanylate cyclase inhibitor, such as methylene blue, butylated hydroxyanisole, and/or N-methylhydroxylamine. In some embodiments, the bioactive agent comprises 2-(4-methylaminobutoxy) diphenylmethane. In some embodiments, the bioactive agent comprises a combination of apraclonidine and timolol.

In some embodiments, the bioactive agent comprises a cloprostenol analog or a fluprostenol analog. In some embodiments, the bioactive agent comprises a crosslinked carboxy-containing polymer, a sugar, and water. In some embodiments, the bioactive agent comprises a non-corneotoxic serine-threonine kinase inhibitor. In some embodiments, the bioactive agent comprises a nonsteroidal glucocorticoid antagonist. In some embodiments, the bioactive agent comprises a prostaglandin analog or a derivative thereof.

These and other embodiments of the inventions will become apparent to those skilled in the art from the following detailed description of exemplary embodiments having reference to the attached figures, the inventions not being limited to any particular preferred embodiment(s) disclosed.

BRIEF DESCRIPTION OF THE DRAWINGS

Certain preferred embodiments and modifications thereof will become apparent to those skilled in the art from the detailed description herein having reference to the figures that follow, of which:

FIG. 4 is a side elevational view of the stent of FIG. 3.

FIG. 5 is a top plan view of the stent of FIG. 3.

FIG. 6 is a bottom plan view of the stent of FIG. 3.

FIG. 7 is a front elevational view of the stent of FIG. 3 (along line 7-7 of FIG. 4).

FIG. 8 is a rear elevational view of the stent of FIG. 3 (along line 8-8 of FIG. 4).

FIG. 16 is a side elevational view of yet another modification of the glaucoma stent of FIG. 3.

FIG. 17 is a top plan view of the stent of FIG. 16.

FIG. 18 is a bottom plan view of the stent of FIG. 16.

FIG. 19 is a front elevational view along line 19-19 of FIG. 16.

FIG. 20 is a rear elevational view along line 20-20 of FIG. 16.

FIG. 21 is a side elevation view of still another modification of the glaucoma stent of FIG. 3.

FIG. 22 is a top plan view of the stent of FIG. 21.

FIG. 23 is a bottom plan view of the stent of FIG. 21.

FIG. 24 is a front elevational view along line 24-24 of FIG. 21.

FIG. 25 is a rear elevational view along line 25-25 of FIG. 21.

FIG. 26 is a front elevational view of a modification of the glaucoma stent illustrated in FIG. 3.

FIG. 27 is a right side elevational view of the stents illustrated in FIG. 26 as viewed along the line 27-27.

FIG. 28 is a right side elevational view of the glaucoma stent illustrated in FIG. 26, as viewed along the line 28-28.

FIG. 51D is an oblique side elevational view of the steerable section of the delivery applicator illustrated in FIG. 51A and including an optional ultrasonically enabled distal end.

DETAILED DESCRIPTION OF EXEMPLARY EMBODIMENTS

The preferred embodiments described herein relate particularly to surgical and therapeutic treatment of glaucoma through reduction of intraocular pressure and/or stimulation of the trabecular meshwork tissue. While the description sets forth various embodiment-specific details, it will be appreciated that the description is illustrative only and should not be construed in any way as limiting the invention. Furthermore, various applications of the inventions disclosed herein, and modifications thereto, which may occur to those who are skilled in the art, are also encompassed by the general concepts described herein.

Figure 1:
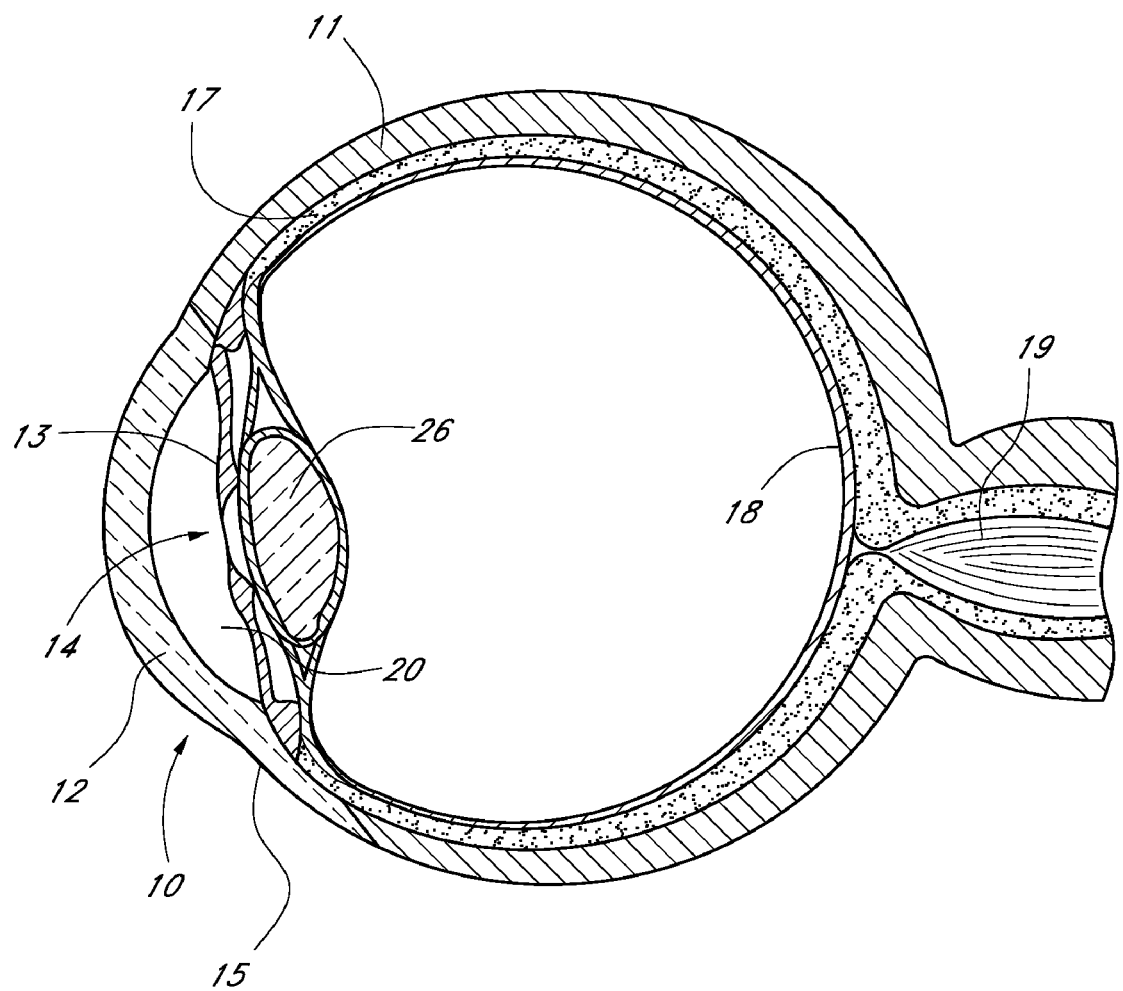
FIG. 1 is a coronal cross-sectional view of an eye.
Figure 2:
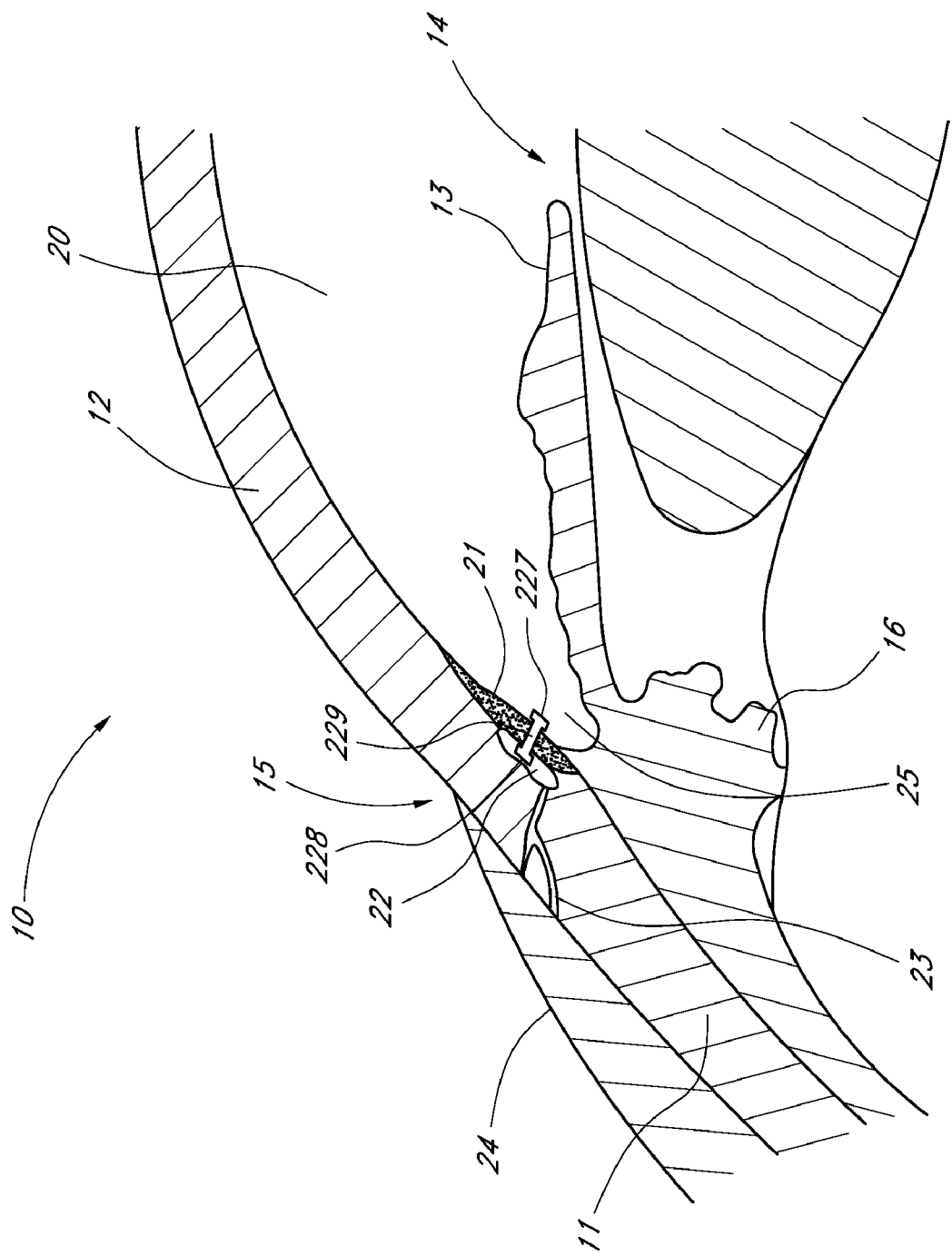
FIG. 2 is an enlarged cross-sectional view of an anterior chamber angle of the eye of FIG. 1 with a trabecular stent.

FIG. 1 is a cross-sectional view of an eye 10. FIG. 2 is an enlarged sectional view of the eye showing the relative anatomical locations of a trabecular meshwork 21, an anterior chamber 20, and a Schlemm's canal 22. A sclera 11 is a thick collagenous tissue that covers the entire eye 10 except a portion that is covered by a cornea 12.

With reference to FIGS. 1 and 2, the cornea 12 is a thin transparent tissue that focuses and transmits light into the eye and through a pupil 14, which is a circular hole in the center of an iris 13 (colored portion of the eye). The cornea 12 merges into the sclera 11 at a juncture referred to as a limbus 15. A ciliary body 16 extends along the interior of the sclera 11 and is coextensive with a choroid 17. The choroid 17 is a vascular layer of the eye 10, located between the sclera 11 and a retina 18. An optic nerve 19 transmits visual information to the brain and is the anatomic structure that is progressively destroyed by glaucoma.

With continued reference to FIGS. 1 and 2, the anterior chamber 20 of the eye 10, which is bound anteriorly by the cornea 12 and posteriorly by the iris 13 and a lens 26, is filled with aqueous humor (hereinafter referred to as "aqueous"). Aqueous is produced primarily by the ciliary body 16, then moves anteriorly through the pupil 14 and reaches an anterior chamber angle 25, formed between the iris 13 and the cornea 12.

As best illustrated by the drawing of FIG. 2, in a normal eye, aqueous is removed from the anterior chamber 20 through the trabecular meshwork 21. Aqueous passes through the trabecular meshwork 21 into Schlemm's canal 22 and thereafter through a plurality of collector ducts and aqueous veins 23, which merge with blood-carrying veins, and into systemic venous circulation. Intraocular pressure is maintained by an intricate balance between secretion and outflow of aqueous in the manner described above. Glaucoma is, in most cases, characterized by an excessive buildup of aqueous in the anterior chamber 20, which leads to an increase in intraocular pressure. Fluids are relatively incompressible, and thus intraocular pressure is distributed relatively uniformly throughout the eye 10.

As shown in FIG. 2, the trabecular meshwork 21 is adjacent a small portion of the sclera 11. Exterior to the sclera 11 is a conjunctiva 24. Traditional procedures that create a hole or opening for implanting a device through the tissues of the conjunctiva 24 and sclera 11 involve extensive surgery, as compared to surgery for implanting a device, as described herein, which ultimately resides entirely within the confines of the sclera 11 and cornea 12. A trabecular stent 229 can be placed bypassing the trabecular meshwork 21 with a proximal terminal 227 exposed to anterior chamber 20 and a distal terminal 228 exposed to Schlemm's canal 22.

Figure 3:
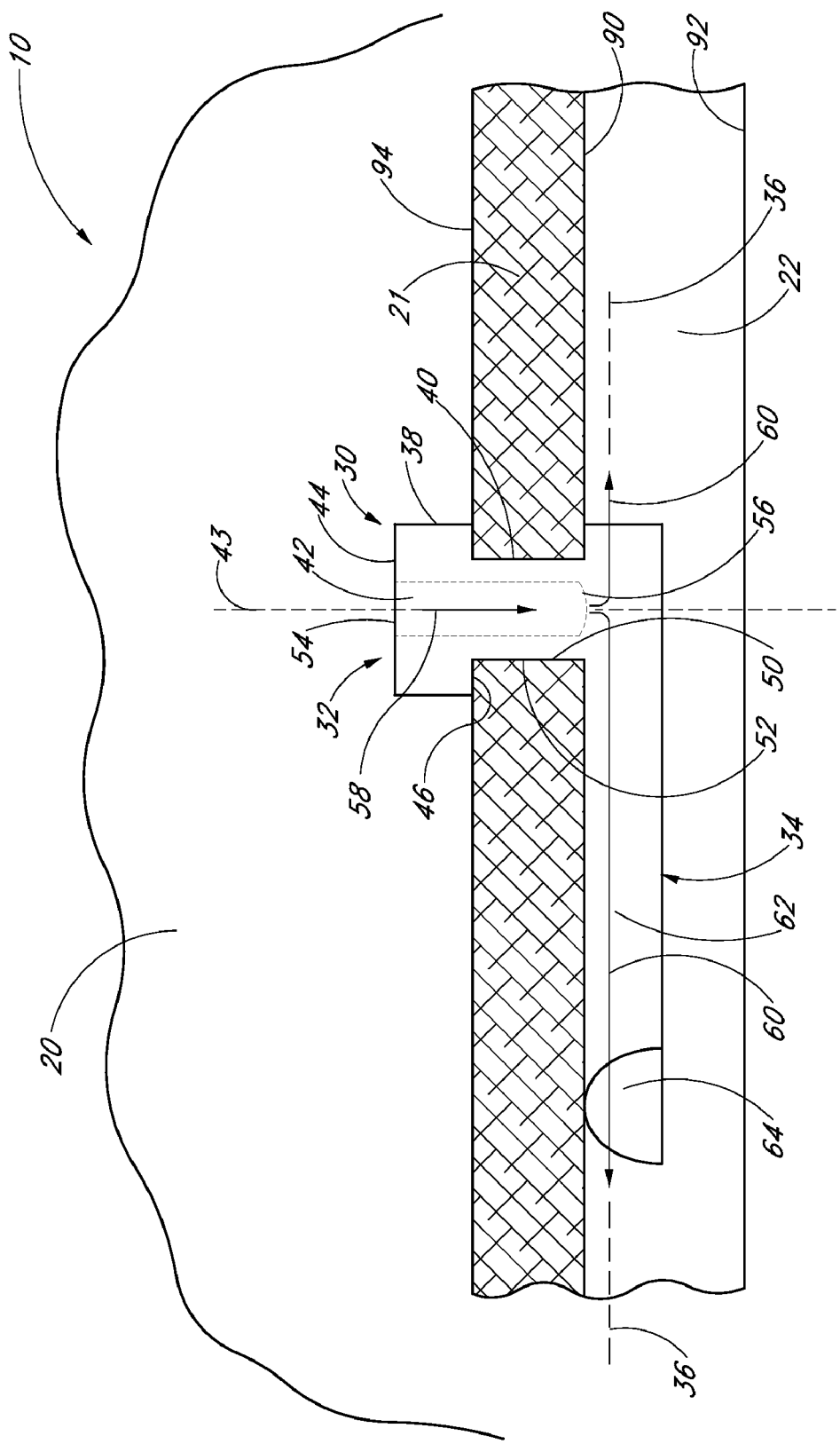
FIG. 3 is a schematic and partial sectional view of an eye illustrating an implanted glaucoma stent in accordance with one embodiment of at least one of the inventions disclosed herein.

FIG. 3 schematically illustrates the use of one embodiment of a trabecular stenting device 30 for establishing an outflow pathway, passing through the trabecular meshwork 21, described in greater detail below. FIGS. 4-9 are different views of the stent 30. Advantageously, and as discussed in further detail later herein, the self-trephining-stent allows a one-step procedure to make an incision in the trabecular mesh 21 and place the stent or implant 30 at the desired or predetermined position within the eye 10. Desirably, this facilitates and simplifies the overall surgical procedure.

In the illustrated embodiment of FIGS. 3-9, the shunt or stent 30 generally comprises an inlet portion or "snorkel" 32 and a main body portion or blade 34. The snorkel 32 and blade 34 are mechanically connected to or in mechanical communication with one another. A generally longitudinal axis 36 extends along the stent 30 and/or the body portion 34.

In the illustrated embodiment of FIGS. 3-9, the stent 30 comprises an integral unit. In modified embodiments, the stent 30 may comprise an assembly of individual pieces or components. For example, the stent 30 may comprise an assembly of the snorkel 32 and blade 34.

In the illustrated embodiment of FIGS. 3-9, the snorkel 32 is in the form of a generally elongate tubular member and generally comprises an upper seat, head or cap portion 38, a shank portion 40 and a lumen or passage 42 extending therethrough. The seat 38 is mechanically connected to or in mechanical communication with the shank 40, which is also mechanically connected to, or in mechanical communication with the blade 34. The longitudinal axis 43 extends along the snorkel 32 and/or the lumen 42.

In the illustrated embodiment of FIGS. 3-9, the seat 38 is generally circular in shape and has an upper surface 44 and a lower surface 46, which, as shown in FIG. 3, abuts or rests against the trabecular meshwork 21 to stabilize the glaucoma stent 30 within the eye 10. In modified embodiments, the seat 38 may efficaciously be shaped in other suitable manners, as required or desired, giving due consideration to the goals of stabilizing the glaucoma stent 30 within the eye 10 and/or of achieving one or more of the benefits and advantages as taught or suggested herein. For example, the seat 38 may be shaped in other polygonal or non-polygonal shapes and/or comprise one or more ridges which extend radially outwards, among other suitable retention devices.

Figure 10:
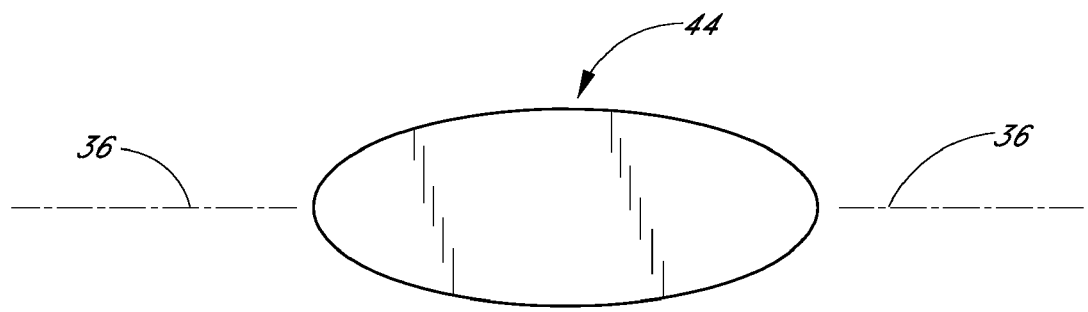
FIG. 10 is a top plan view of a modification of an inlet end of the stent of FIG. 3.
Figure 11:
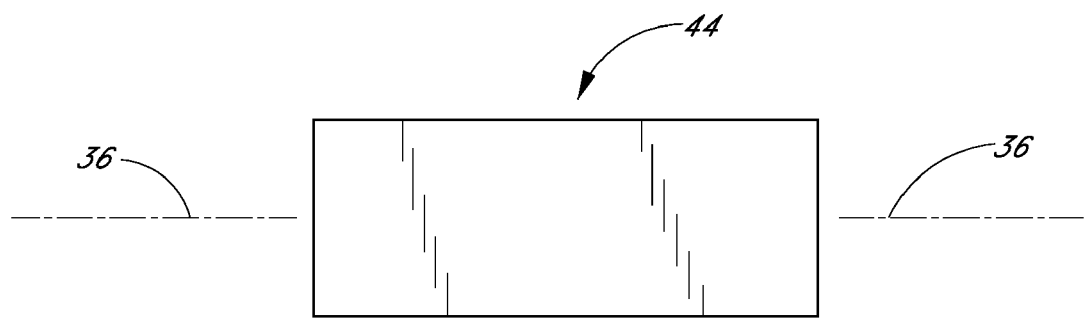
FIG. 11 is a top plan view of another modification of the inlet end of the stent of FIG. 3.
Figure 12:
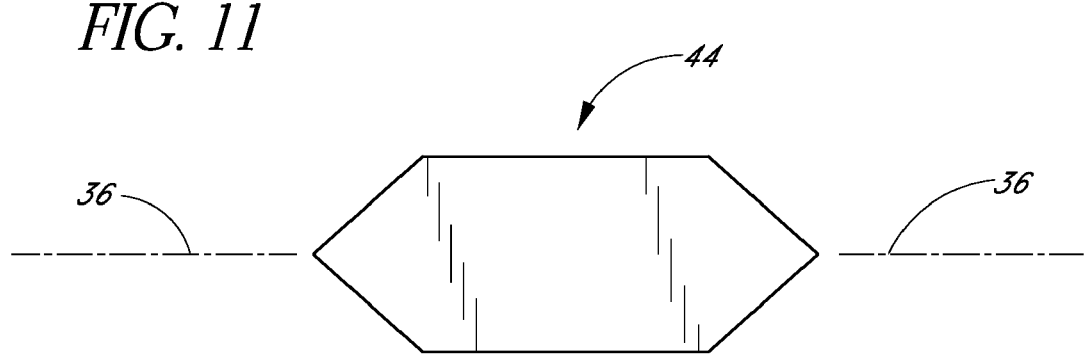
FIG. 12 is a top plan view of yet another modification of the inlet end of the stent of FIG. 3.
Figure 13:
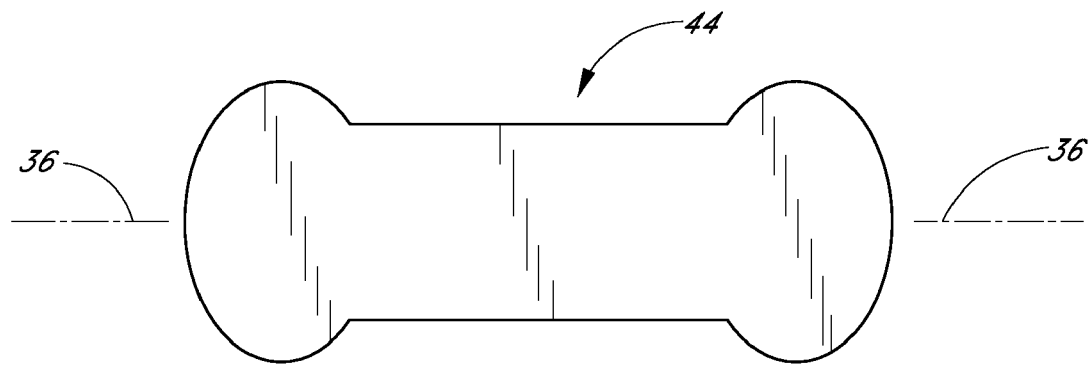
FIG. 13 is a top plan view of still another modification of the inlet end of the stent of FIG. 3.

In the illustrated embodiment of FIGS. 3-9, and as best seen in the top view of FIG. 5, the seat top surface 44 comprises fiducial marks or indicia 48. These marks or indicia 48 facilitate and ensure proper orientation and alignment of the stent 30 when implanted in the eye 10. The marks or indicia 48 may comprise visual differentiation means such as color contrast or be in the form of ribs, grooves, or the like. Alternatively, or in addition, the marks 48 may provide tactile sensory feedback to the surgeon by incorporating a radio-paque detectable or ultrasound imaginable substrate at about the mark 48. Also, the seat 38 and/or the seat top surface 44 may be configured in predetermined shapes aligned with the blade 34 and/or longitudinal axis 36 to provide for proper orientation of the stent device 30 within the eye 10. For example, the seat top surface 44 may be oval or ellipsoidal (FIG. 10), rectangular (FIG. 11), hexagonal (FIG. 12), among other suitable shapes (e.g. FIG. 13).

In the illustrated embodiment of FIGS. 3-9, and as indicated above, the seat bottom surface 46 abuts or rests against the trabecular meshwork 21 to stabilize and retain the glaucoma stent 30 within the eye 10. For stabilization purposes, the seat bottom surface 46 may comprise a studded surface, a ribbed surface, a surface with pillars, a textured surface, or the like.

In the illustrated embodiment of FIGS. 3-9, the snorkel shank 40 is generally cylindrical in shape. With the stent 30 implanted, as shown in FIG. 3, the shank 40 is generally positioned in an incision or cavity 50 formed in the trabecular meshwork 21 by the self-trephining stent 30. Advantageously, and as discussed further below, this single step of forming the cavity 50 by the stent 30 itself and placing the stent 30 in the desired position facilitates and expedites the overall surgical procedure. In modified embodiments, the snorkel shank 40 may efficaciously be shaped in other suitable manners, as required or desired. For example, the shank 40 may be in the shape of other polygonal or non-polygonal shapes, such as, oval, ellipsoidal, and the like.

In the illustrated embodiment of FIGS. 3-9, and as best seen in FIG. 3, the shank 40 has an outer surface 52 in contact with the trabecular meshwork 21 surrounding the cavity 50. For stabilization purposes, the shank outer surface 52 may comprise a studded surface, a ribbed surface, a surface with pillars, a textured surface, or the like.

In the illustrated embodiment of FIGS. 3-9, the snorkel lumen 42 has an inlet port, opening or orifice 54 at the seat top surface 44 and an outlet port, opening or orifice 56 at the junction of the shank 40 and blade 34. The lumen 42 is generally cylindrical in shape, that is, it has a generally circular cross-section, and its ports 54, 56 are generally circular in shape. In modified embodiments, the lumen 42 and ports 54, 56 may be efficaciously shaped in other manners, as required or desired, giving due consideration to the goals of providing sufficient aqueous outflow and/or of achieving one or more of the benefits and advantages as taught or suggested herein. For example, the lumen 42 and/or one or both ports 54, 56 may be shaped in the form of ovals, ellipsoids, and the like, or the lumen 42 may have a tapered or stepped configuration.

Referring in particular to FIG. 3, aqueous from the anterior chamber 20 flows into the lumen 42 through the inlet port 54 (as generally indicated by arrow 58) and out of the outlet port 56 and into Schlemm's canal 22 (as generally indicated by arrows 60) to lower and/or balance the intraocular pressure (IOP). In another embodiment, as discussed in further detail below, one or more of the outlet ports may be configured to face in the general direction of the stent longitudinal axis 36. In modified embodiments, the snorkel 32 may comprise more than one lumen, as needed or desired, to facilitate multiple aqueous outflow transportation into Schlemm's canal 22.

In the illustrated embodiment of FIGS. 3-9, the blade longitudinal axis 36 and the snorkel longitudinal axis 43 are generally perpendicular to one another. Stated differently, the projections of the axes 36, 43 on a common plane which is not perpendicular to either of the axes 36, 43 intersect at 90°. The blade longitudinal axis 36 and the snorkel longitudinal axis 43 may intersect one another or may be offset from one another.

In the illustrated embodiment of FIGS. 3-9, the main body portion or blade 34 is a generally curved elongated sheet- or plate-like structure with an upper curved surface 62 and a lower curved surface 64, which defines a trough or open face channel 66. The perimeter of the blade 34 is generally defined by a curved proximal edge 68 proximate to the snorkel 32, a curved distal edge 70 spaced from the proximal edge 68 by a pair of generally straight lateral edges 72, 74. The first lateral edge 72 extends beyond the second lateral edge 74 and intersects with the distal edge 70 at a distal-most point 76 of the blade 34. Preferably, the blade 34 defines a blade cutting tip 78.

Figure 9:
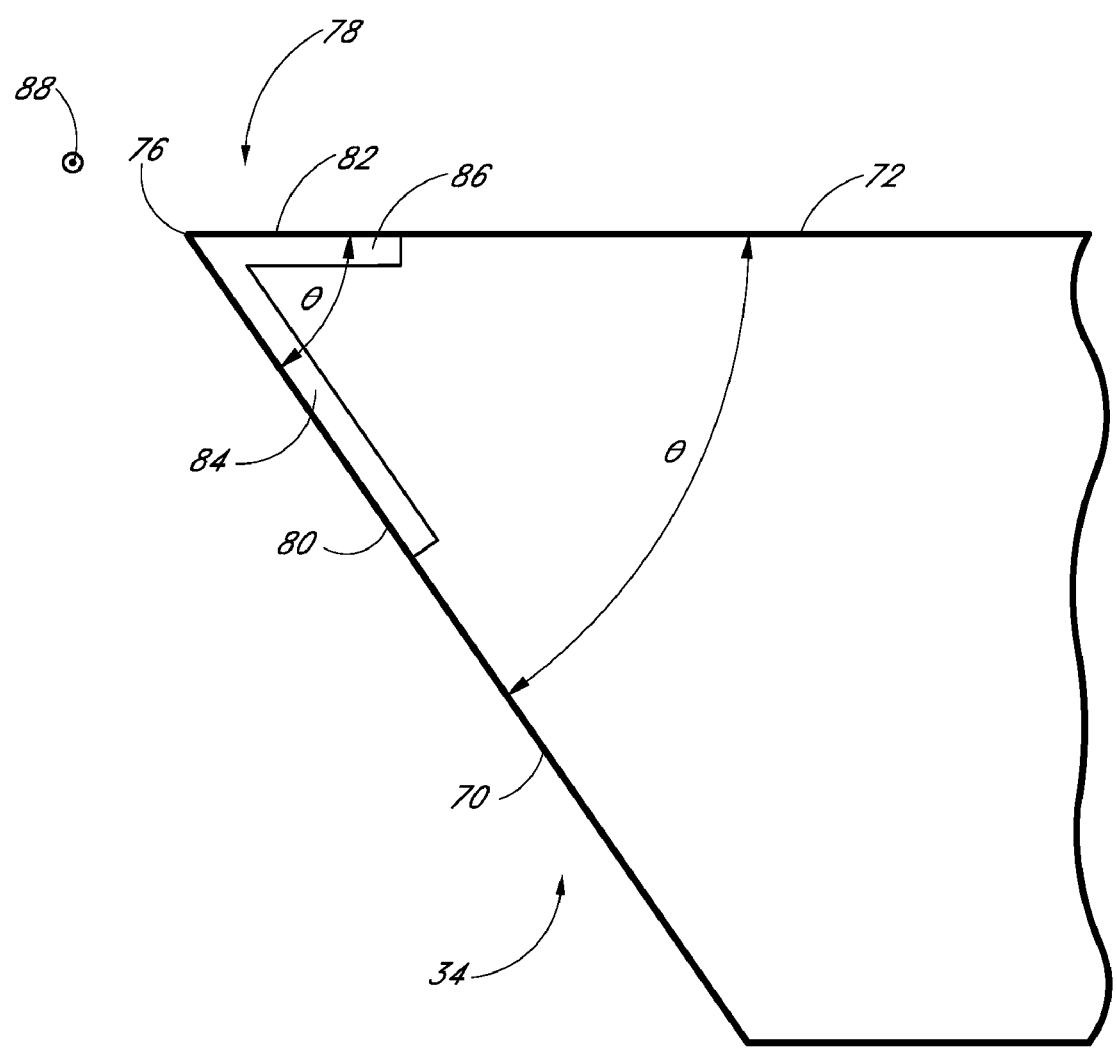
FIG. 9 is an enlarged top plan view of a forward end of the stent of FIG. 3.

In the illustrated embodiment of FIGS. 3-9, and as shown in the enlarged view of FIG. 9, the cutting tip 78 comprises a first cutting edge 80 on the distal edge 70 and a second cutting edge 82 on the lateral edge 72. The cutting edges 80, 82 preferably extend from the distal-most point 76 of the blade 34 and comprise at least a respective portion of the distal edge 70 and lateral edge 72. The respective cutting edges 80, 82 are formed at the sharp edges of respective beveled or tapered surfaces 84, 86. In one embodiment, the remainder of the distal edge 70 and lateral edge 72 are dull or rounded. In one embodiment, the tip 78 proximate to the distal-most end 76 is curved slightly inwards, as indicated generally by the arrow 88 in FIG. 5 and arrow 88 (pointed perpendicular and into the plane of the paper) in FIG. 9, relative to the adjacent curvature of the blade 34.

In modified embodiments, suitable cutting edges may be provided on selected portions of one or more selected blade edges 68, 70, 72, 74 with efficacy, as needed or desired, giving due consideration to the goals of providing suitable cutting means on the stent 30 for effectively cutting through the trabecular meshwork 21 (FIG. 3) and/or of achieving one or more of the benefits and advantages as taught or suggested herein.

Referring in particular to FIG. 9, in one embodiment, the ratio between the lengths of the cutting edges 80, 82 is about 2:1. In another embodiment, the ratio between the lengths of the cutting edges 80, 82 is about 1:1. In yet another embodiment, the ratio between the lengths of the cutting edges 80, 82 is about 1:2. In modified embodiments, the lengths of the cutting edges 80, 82 may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

Still referring in particular to FIG. 9, in one embodiment, the ratio between the lengths of the cutting edges 80, 82 is in the range from about 2:1 to about 1:2. In another embodiment, the ratio between the lengths of the cutting edges 80, 82 is in the range from about 5:1 to about 1:5. In yet another embodiment, the ratio between the lengths of the cutting edges 80, 82 is in the range from about 10:1 to about 1:10. In modified embodiments, the lengths of the cutting edges 80, 82 may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

As shown in the top view of FIG. 9, the cutting edge 80 (and/or the distal end 70) and the cutting edge 82 (and/or the lateral edge 72) intersect at an angle θ. Stated differently, θ is the angle between the projections of the cutting edge 80 (and/or the distal end 70) and the cutting edge 82 (and/or the lateral edge 72) on a common plane that is not perpendicular to either of these edges.

Referring to in particular to FIG. 9, in one embodiment, the angle θ is about 50°. In another embodiment, the angle θ is in the range from about 40° to about 60°. In yet another embodiment, the angle θ is in the range from about 30° to about 70°. In modified embodiments, the angle θ may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

The stent 30 of the embodiments disclosed herein can be dimensioned in a wide variety of manners. Referring in particular to FIG. 3, the depth of Schlemm's canal 22 is typically about less than 400 microns (μm). Accordingly, the stunt blade 34 is dimensioned so that the height of the blade 34 (referred to as $H_{41}$ in FIG. 4) is typically less than about 400 μm. The snorkel shank 40 is dimensioned so that it has a length (referred to as $L_{41}$ in FIG. 4) typically in the range from about 150 μm to about 400 μm, which is roughly the typical range of the thickness of the trabecular meshwork 21.

Of course, as the skilled artisan will appreciate, that with the stent 30 implanted, the blade 34 may rest at any suitable position within Schlemm's canal 22. For example, the blade 34 may be adjacent to a front wall 90 of Schlemm's canal 22 (as shown in FIG. 3), or adjacent to a back wall 92 of Schlemm's canal 22, or at some intermediate location therebetween, as needed or desired. Also, the snorkel shank 40 may extend into Schlemm's canal 22. The length of the snorkel shank 40 and/or the dimensions of the blade 34 may be efficaciously adjusted to achieve the desired implant positioning.

The trabecular stenting device 30 (FIGS. 3-9) of the exemplary embodiment may be manufactured or fabricated by a wide variety of techniques. These include, without limitation, molding, thermo-forming, or other micro-machining techniques, among other suitable techniques.

The trabecular stenting device 30 preferably comprises a biocompatible material such that inflammation arising due to irritation between the outer surface of the device 30 and the surrounding tissue is minimized. Biocompatible materials which may be used for the device 30 preferably include, but are not limited to, titanium, titanium alloys, medical grade silicone, e.g., Silastic™, available from Dow Corning Corporation of Midland, Mich.; and polyurethane, e.g., Pellethane™, also available from Dow Corning Corporation.

In other embodiments, the stent device 30 may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and/or a mixture of the aforementioned biocompatible materials, and the like. In still other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists and other anti-glaucoma drugs, or antibiotics), and the like.

In an exemplary embodiment of the trabecular meshwork surgery, the patient is placed in the supine position, prepped, draped and anesthetized as necessary. A small (less than about 1 mm) incision, which may be self sealing, can then be made through the cornea 12. The corneal incision can be made in a number of ways, for example, by using a micro-knife, among other tools.

An applicator or delivery apparatus is used to advance the glaucoma stent 30 through the corneal incision and to the trabecular meshwork 21. Some embodiments of such a delivery apparatus are disclosed in copending U.S. application Ser. No. 10/101,548, filed Mar. 18, 2002, entitled APPLICATOR AND METHODS FOR PLACING A TRABECULAR SHUNT FOR GLAUCOMA TREATMENT, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein. Some embodiments of a delivery apparatus are also described in further detail below. Gonioscopic, microscopic, or endoscopic guidance can be used during the trabecular meshwork surgery.

With the device 30 held by the delivery apparatus, the blade 34 of the device 30 is used to cut and/or displace the material of the trabecular meshwork 21. The snorkel shank 40 can also facilitate in removal of this material during implantation. The delivery apparatus is withdrawn once the device 30 has been implanted in the eye 10. As shown in FIG. 3, the snorkel seat 38 can rest on a top surface 94 of the trabecular meshwork 21 with the snorkel shank 40 extending through the cavity 50 (created by the device 30) in the trabecular meshwork 21, and with the blade 34 extending inside Schlemm's canal 22.

Advantageously, the embodiments of the self-trephining stent device 30 allow for a "one-step" procedure to make an incision in the trabecular meshwork and to implant the stent in the proper orientation and alignment within the eye to allow outflow of aqueous from the anterior chamber through the stent and into Schlemm's canal to lower and/or balance the intraocular pressure (IOP). Desirably, this provides for a faster, safer, and less expensive surgical procedure.

Many complications can arise in trabecular meshwork surgeries, wherein a knife is first used to create an incision in the trabecular meshwork, followed by removal of the knife and subsequent installation of the stent. For instance, the knife may cause some bleeding which clouds up the surgical site. This may require more effort and time to clean the surgical site prior to placement of the stent. Moreover, this may cause the intraocular pressure (IOP) to rise or to fall undesirably. Thus, undesirably, such a multiple step procedure may demand crisis management that slows down the surgery, makes it less safe, and more expensive.

Figure 14:
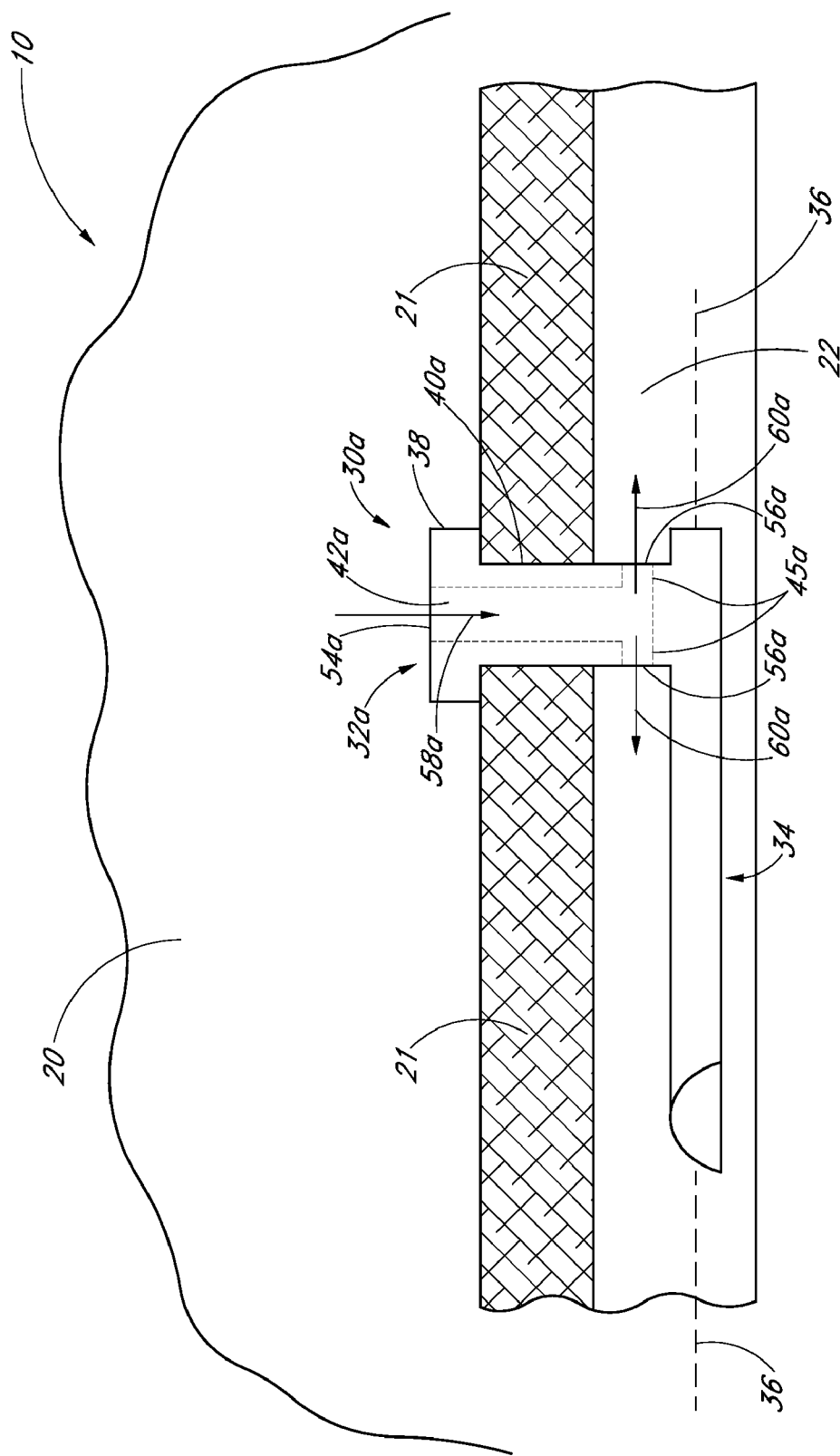
FIG. 14 is schematic and partial sectional view of an eye illustrating a modification of the implanted glaucoma stent of FIG. 3.

FIG. 14 is a simplified partial view of an eye 10 illustrating the implantation of a self-trephining glaucoma stent device 30a having features and advantages in accordance with one embodiment. The stent 30a is generally similar to the stent 30 of FIGS. 3-9 except that its snorkel 32a comprises a longer shank 40a, which extends into Schlemm's canal 22 and a lumen 42a, which bifurcates into two output channels 45a.

In the illustrated embodiment of FIG. 14, the shank 40a terminates at the blade 34. Aqueous flows from the anterior chamber 20 into the lumen 42a through an inlet port 54a (as generally indicated by arrow 58a). Aqueous then flows through the output channels 45a and out of respective outlet ports 56a and into Schlemm's canal 22 (as generally indicated by arrows 60a). The outlet channels 45a extend radially outwards in generally opposed directions and the outlet ports 56a are configured to face in the general direction of the stent longitudinal axis 36 so that they open into Schlemm's canal 22 and are in proper orientation to allow aqueous outflow into Schlemm's canal 22 for lowering and/or balancing the intraocular pressure (IOP). As indicated above, fiducial marks or indicia and/or predetermined shapes of the snorkel seat 38 allow for proper orientation of the blade 34 and also the output channels 45a and respective ports 56a within Schlemm's canal.

In the illustrated embodiment of FIG. 14, two outflow channels 45a are provided. In another embodiment, only one outflow channel 45a is provided. In yet another embodiment, more than two outflow channels 45a are provided. In modified embodiments, the lumen 42a may extend all the way through to the blade 34 and provide an outlet port as discussed above with reference to the embodiment of FIGS. 3-9.

Figure 15:
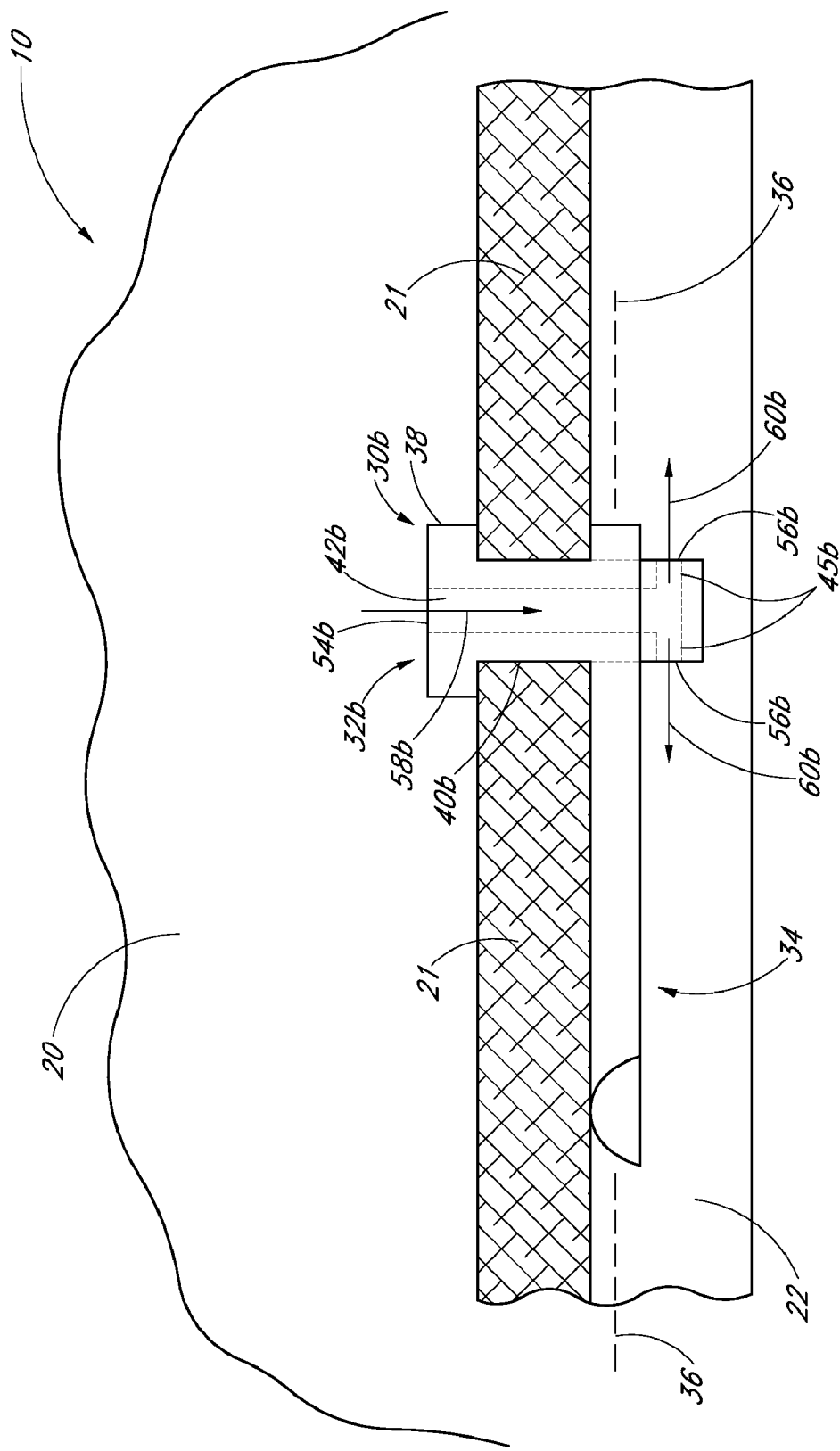
FIG. 15 is a schematic and partial sectional view of an eye illustrating a further modification of the implanted glaucoma stent of FIG. 3.

FIG. 15 is a simplified partial view of an eye 10 illustrating the implantation of a self-trephining glaucoma stent device 30b having features and advantages in accordance with one embodiment. The stent 30b is generally similar to the stent 30 of FIGS. 3-9 except that its snorkel 32b comprises a longer shank 40b, which extends into Schlemm's canal 22 and a lumen 42b, which bifurcates into two output channels 45b.

In the illustrated embodiment of FIG. 15, the shank 40b extends through the blade 34. Aqueous flows from the anterior chamber 20 into the lumen 42b through an inlet port 54b (as generally indicated by arrow 58b). Aqueous then flows through the output channels 45b and out of respective outlet ports 56b and into Schlemm's canal 22 (as generally indicated by arrows 60b). The outlet channels 45b extend radially outwards in generally opposed directions and the outlet ports 56b are configured to face in the general direction of the stent longitudinal axis 36 so that they open into Schlemm's canal 22 and are in proper orientation to allow aqueous outflow into Schlemm's canal 22 for lowering and/or balancing the intraocular pressure (IOP). As indicated above, fiducial marks or indicia and/or predetermined shapes of the snorkel seat 38 allow for proper orientation of the blade 34 and also the output channels 45b and respective ports 56b within Schlemm's canal.

In the illustrated embodiment of FIG. 15, two outflow channels 45b are provided. In another embodiment, only one outflow channel 45b is provided. In yet another embodiment, more than two outflow channels 45b are provided. In modified embodiments, the lumen 42b may extend all the way through to the blade 34 and provide an outlet port as discussed above with reference to the embodiment of FIGS. 3-9.

FIGS. 16-20 show different views of a self-trephining glaucoma stent device 30c having features and advantages in accordance with one embodiment. The stent 30c is generally similar to the stent 30 of FIGS. 3-9 except that it has a modified blade configuration. The stent 30c comprises a blade 34c which is a generally curved elongated sheet- or plate-like structure with an upper curved surface 62c and a lower curved surface 64c which defines a trough or open face channel 66c. The perimeter of the blade 34c is generally defined by a curved proximal edge 68c proximate to the snorkel 32, a curved distal edge 70c spaced from the proximal edge 68c by a pair of generally straight lateral edges 72c, 74c which are generally parallel to one another and have about the same length.

In the illustrated embodiment of FIGS. 16-20, the blade 34c comprises a cutting tip 78c. The cutting tip 78c preferably includes cutting edges formed on selected portions of the distal edge 70c and adjacent portions of the lateral edges 72c, 74c for cutting through the trabecular meshwork for placement of the snorkel 32. The cutting edges are sharp edges of beveled or tapered surfaces as discussed above in reference to FIG. 9. The embodiment of FIGS. 16-20 may be efficaciously modified to incorporate the snorkel configuration of the embodiments of FIGS. 14 and 15.

FIGS. 21-25 show different views of a self-trephining glaucoma stent device 30d having features and advantages in accordance with one embodiment. The stent 30d is generally similar to the stent 30 of FIGS. 3-9 except that it has a modified blade configuration. The stent 30d comprises a blade 34d which is a generally curved elongated sheet- or plate-like structure with an upper curved surface 62d and a lower curved surface 64d which defines a trough or open face channel 66d. The perimeter of the blade 34d is generally defined by a curved proximal edge 68d proximate to the snorkel 32, a pair of inwardly converging curved distal edges 70d', 70d" spaced from the proximal edge 68d by a pair of generally straight respective lateral edges 72d, 74d which are generally parallel to one another and have about the same length. The distal edges 70d', 70d" intersect at a distal-most point 76d of the blade 34d proximate a blade cutting tip 78d.

In the illustrated embodiment of FIGS. 21-25, the cutting tip 78d preferably includes cutting edges formed on the distal edges 70d', 70d" and extending from the distal-most point 76d of the blade 34d. In one embodiment, the cutting edges extend along only a portion of respective distal edges 70d', 70d." In another embodiment, the cutting edges extend along substantially the entire length of respective distal edges 70d', 70d." In yet another embodiment, at least portions of the lateral edges 72d, 74d proximate to respective distal edges 70d', 70d" have cutting edges. In a further embodiment, the tip 78d proximate to the distal-most end 76d is curved slightly inwards, as indicated generally by the arrow 88d in FIG. 21 and arrow 88d (pointed perpendicular and into the plane of the paper) in FIG. 22, relative to the adjacent curvature of the blade 34d.

In the embodiment of FIGS. 21-25, the cutting edges are sharp edges of beveled or tapered surfaces as discussed above in reference to FIG. 9. The embodiment of FIGS. 21-25 may be efficaciously modified to incorporate the snorkel configuration of the embodiments of FIGS. 14 and 15.

FIGS. 26-28 show different views of a self-trephining glaucoma stent device 30e having features and advantages in accordance with one embodiment. The stent device 30e generally comprises a snorkel 32e mechanically connected to or in mechanical communication with a blade or cutting tip 34e. The snorkel 32e has a seat, head or cap portion 38e mechanically connected to or in mechanical communication with a shank 40e, as discussed above. The shank 40e has a distal end or base 47e. The snorkel 32e further has a lumen 42e, which bifurcates into a pair of outlet channels 45e, as discussed above in connection with FIGS. 14 and 15. Other lumen and inlet and outlet port configurations as taught or suggested herein may also be efficaciously used, as needed or desired.

In the illustrated embodiment of FIGS. 26-28, the blade 34e extends downwardly and outwardly from the shank distal end 47e. The blade 34e is angled relative to a generally longitudinal axis 43e of the snorkel 32e, as best seen in FIGS. 27 and 28. The blade 34e has a distal-most point 76e. The blade or cutting tip 34e has a pair of side edges 70e', 70e," including cutting edges, terminating at the distal-most point 76e, as best seen in FIG. 26. In one embodiment, the cutting edges are sharp edges of beveled or tapered surfaces as discussed above in reference to FIG. 9.

Referring to FIGS. 26-28, in one embodiment, the blade 34e includes cutting edges formed on the edges 70e', 70e" and extending from the distal-most point 76e of the blade 34d. In one embodiment, the cutting edges extend along only a portion of respective distal edges 70e', 70e." In another embodiment, the cutting edges extend along substantially the entire length of respective distal edges 70e', 70e." In yet another embodiment, the blade or cutting tip 34e comprises a bent tip of needle, for example, a 30 gauge needle.

In general, any of the blade configurations disclosed herein may be used in conjunction with any of the snorkel configurations disclosed herein or incorporated by reference herein to provide a self-trephining glaucoma stent device for making an incision in the trabecular meshwork for receiving the corresponding snorkel to provide a pathway for aqueous outflow from the eye anterior chamber to Schlemm's canal, thereby effectively lowering and/or balancing the intraocular pressure (IOP). The self-trephining ability of the device, advantageously, allows for a "one-step" procedure in which the incision and placement of the snorkel are accomplished by a single device and operation. In any of the embodiments, fiducial markings or indicia, and/or preselected configuration of the snorkel seat, and/or positioning of the stent device in a preloaded applicator may be used for proper orientation and alignment of the device during implantation.

Figure 29:
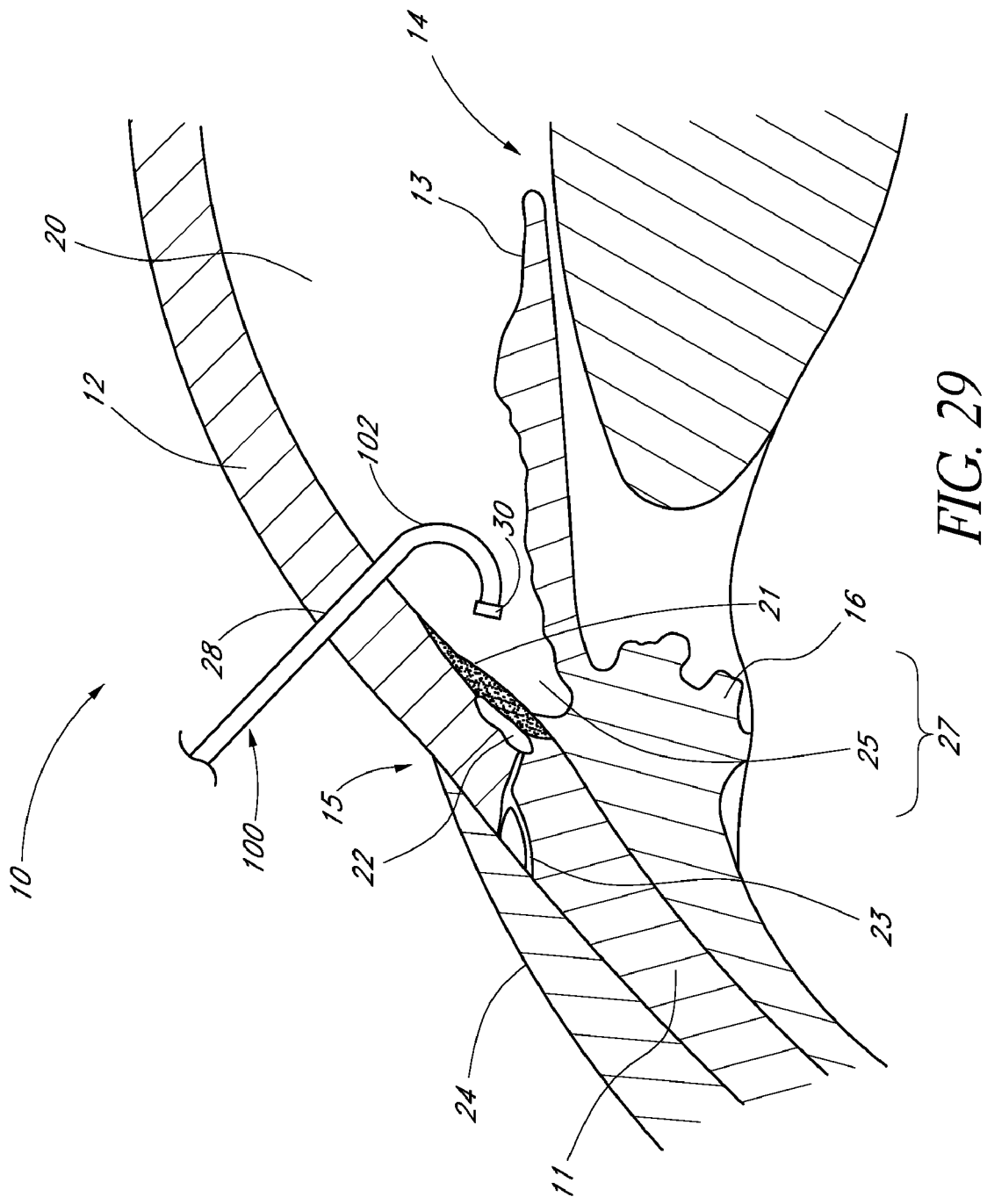
FIG. 29 is a schematic and partial sectional view of an eye illustrating a temporal implantation of a glaucoma stent using a delivery apparatus having features and advantages in accordance with at least one of the inventions disclosed herein.

In many cases, a surgeon works from a temporal incision when performing cataract or goniometry surgery. FIG. 29 illustrates a temporal implant procedure, wherein a delivery apparatus or "applicator" 100 having a curved tip 102 is used to deliver a stent 30 to a temporal side 27 of the eye 10. An incision 28 is made in the cornea 10, as discussed above. The apparatus 100 is then used to introduce the stent 30 through the incision 28 and implant it within the eye 10.

Still referring in particular to FIG. 29, in one embodiment, a similarly curved instrument would be used to make the incision through the trabecular meshwork 21. In other embodiments, a self-trephining stent device 30 may be used to make this incision through the trabecular meshwork 21, as discussed above. The temporal implantation procedure illustrated in FIG. 29 may be employed with the any of the various stent embodiments taught or suggested herein.

Figure 30:
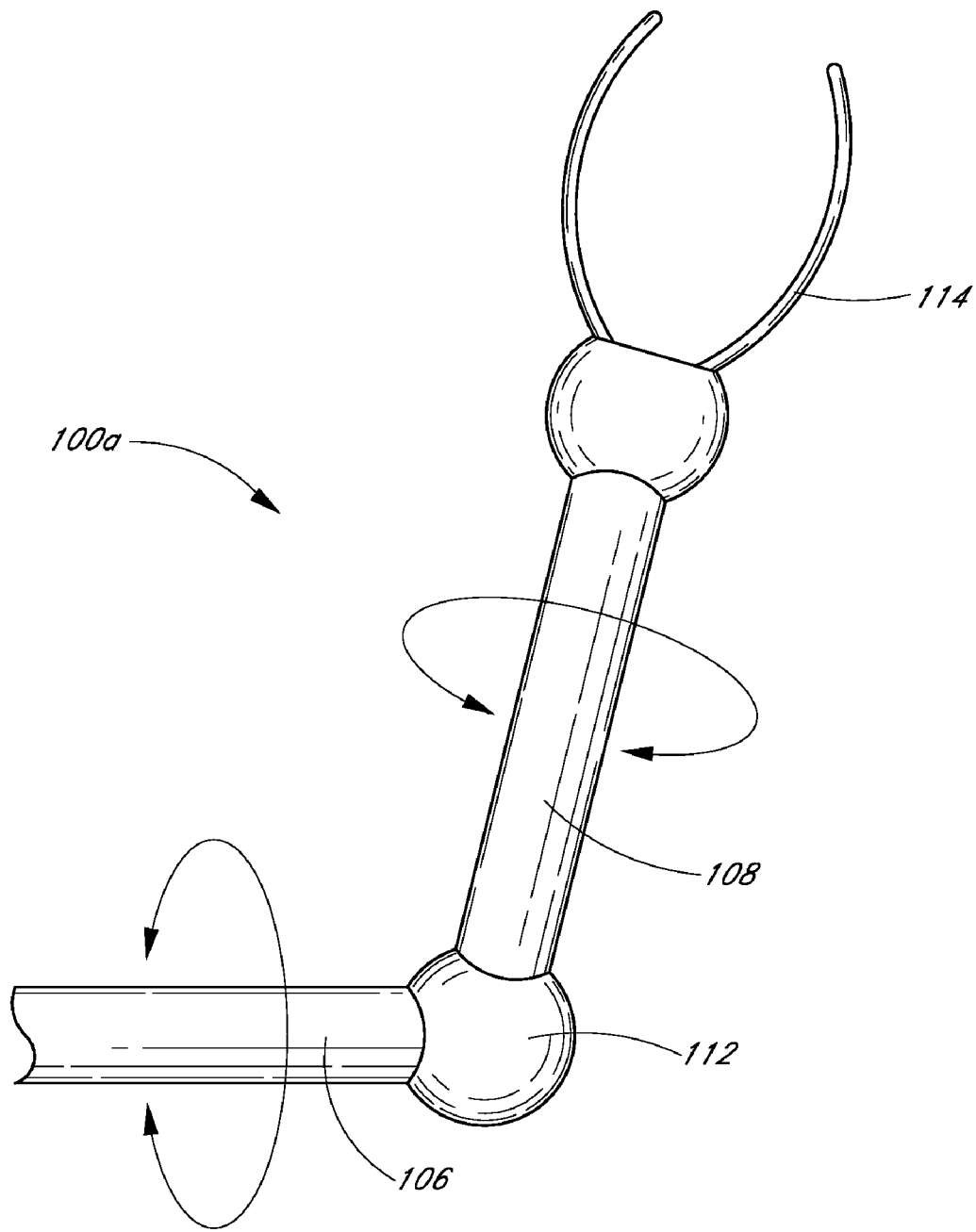
FIG. 30 is an oblique elevational view of an articulating arm stent delivery/retrieval apparatus having features and advantages in accordance with an embodiment of at least one of the inventions disclosed herein.

FIG. 30 illustrates one embodiment of an apparatus comprising an articulating stent applicator or retrieval device 100a. In this embodiment, a proximal arm 106 is attached to a distal arm 108 at a joint 112. This joint 112 is movable such that an angle formed between the proximal arm 106 and the distal arm 108 can change. One or more claws 114 can extend from the distal arm 108, in the case of a stent retrieval device. Similarly, this articulation mechanism may be used for the trabecular stent applicator, and thus the articulating applicator or retrieval device 100a may be either an applicator for the trabecular stent, a retrieval device, or both, in various embodiments. The embodiment of FIG. 30 may be employed with the any of the various stent embodiments taught or suggested herein.

Figure 31:
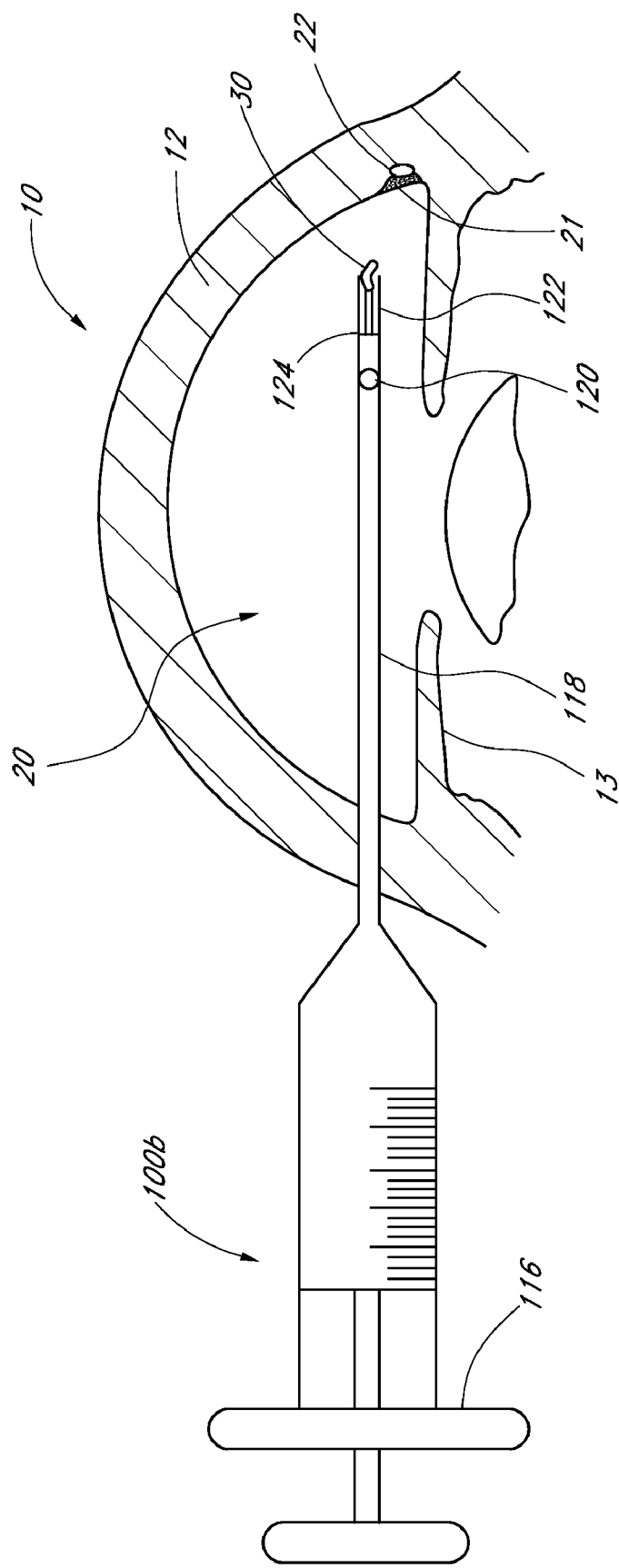
FIG. 31 is a schematic and partial sectional view of a portion of an eye and illustrating an implantation of a glaucoma stent using a delivery apparatus extending through the anterior chamber of the eye.

FIG. 31 shows another illustrative method for placing any of the various stent embodiments taught or suggested herein at the implant site within the eye 10. A delivery apparatus 100b generally comprises a syringe portion 116 and a cannula portion 118. The distal section of the cannula 118 has at least one irrigating hole 120 and a distal space 122 for holding the stent device 30. The proximal end 124 of the lumen of the distal space 122 is sealed from the remaining lumen of the cannula portion 118. The delivery apparatus of FIG. 30 may be employed with the any of the various stent embodiments taught or suggested herein.

In one aspect of the invention, a delivery apparatus (or "applicator") is used for placing a trabecular stent through a trabecular meshwork of an eye. Certain embodiments of such a delivery apparatus are disclosed in copending U.S. application Ser. No. 10/101,548, filed Mar. 18, 2002, entitled APPLICATOR AND METHODS FOR PLACING A TRABECULAR SHUNT FOR GLAUCOMA TREATMENT, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein.

The stent has an inlet section and an outlet section. The delivery apparatus includes a handpiece, an elongate tip, a holder and an actuator. The handpiece has a distal end and a proximal end. The elongate tip is connected to the distal end of the handpiece. The elongate tip has a distal portion and is configured to be placed through a corneal incision and into an anterior chamber of the eye. The holder is attached to the distal portion of the elongate tip. The holder is configured to hold and release the inlet section of the trabecular stent. The actuator is on the handpiece and actuates the holder to release the inlet section of the trabecular stent from the holder. When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger.

In some embodiments, the holder comprises a clamp. In some embodiments, the apparatus further comprises a spring within the handpiece that is configured to be loaded when the stent is being held by the holder, the spring being at least partially unloaded upon actuating the actuator, allowing for release of the stent from the holder.

In various embodiments, the clamp comprises a plurality of claws configured to exert a clamping force onto the inlet section of the stent. The holder may also comprise a plurality of flanges.

In some embodiments, the distal portion of the elongate tip is made of a flexible material. This can be a flexible wire. The distal portion can have a deflection range, preferably of about 45 degrees from the long axis of the handpiece.

The delivery apparatus can further comprise an irrigation port in the elongate tip.

Some aspects include a method of placing a trabecular stent through a trabecular meshwork of an eye, the stent having an inlet section and an outlet section, including advancing a delivery apparatus holding the trabecular stent through an anterior chamber of the eye and into the trabecular meshwork, placing part of the stent through the trabecular meshwork and into a Schlemm's canal of the eye; and releasing the stent from the delivery apparatus.

In various embodiments, the method includes using a delivery apparatus that comprises a handpiece having a distal end and a proximal end; an elongate tip connected to the distal end of the handpiece, the elongate tip having a distal portion and being configured to be placed through a corneal incision and into an anterior chamber of the eye; a holder attached to the distal portion of the elongate tip, the holder configured to hold and release the inlet section of the trabecular stent; and an actuator on the handpiece that actuates the holder to release the inlet section of the trabecular stent from the holder.

In one aspect, the trabecular stent is removably attached to a delivery apparatus (also known as "applicator"). When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger. In some embodiments, the delivery applicator may be a guidewire, an expandable basket, an inflatable balloon, or the like.

Screw/Barb Anchored Stent

Figure 32:
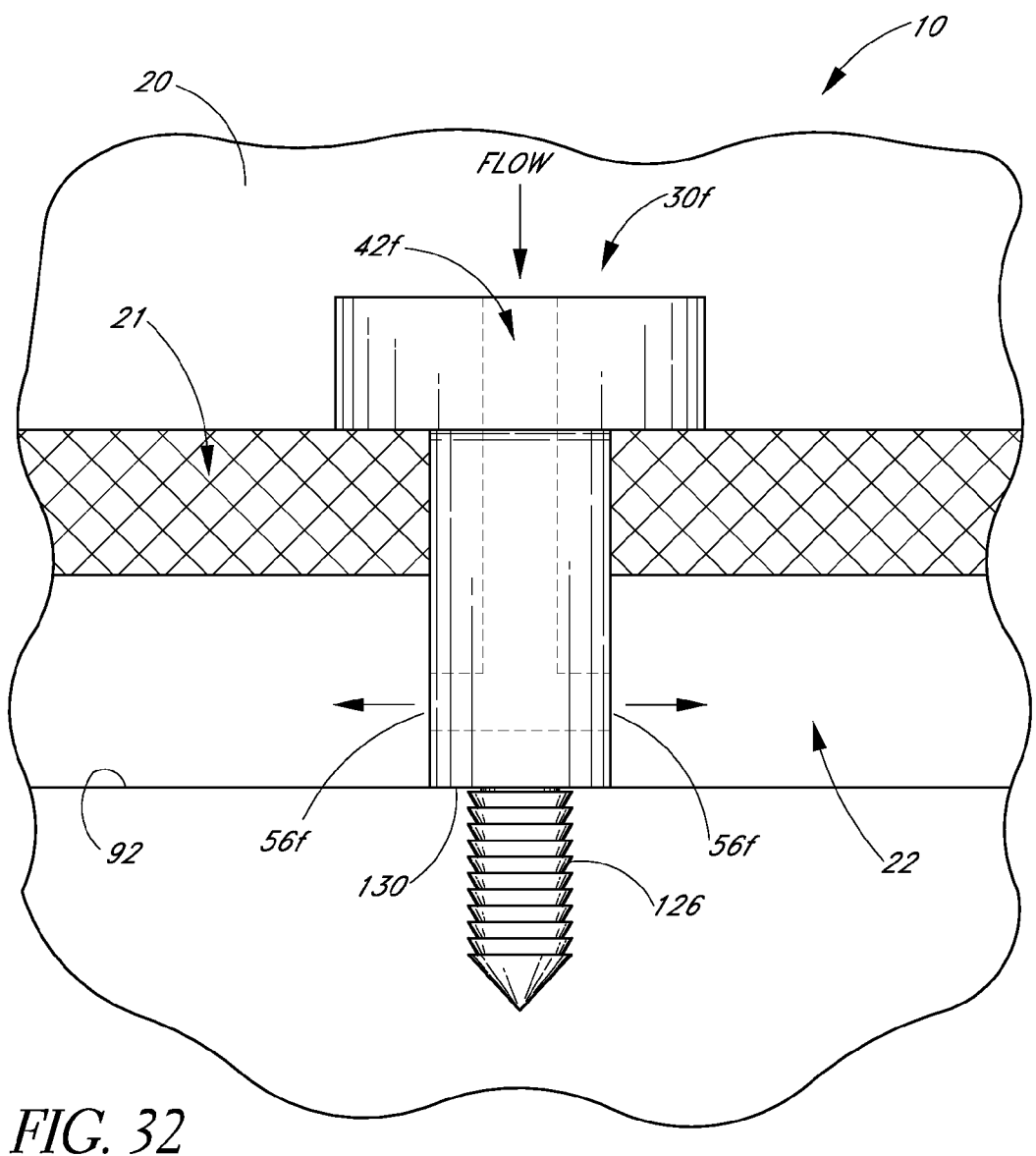
FIG. 32 is a schematic and partial sectional view of a Schlemm's canal and trabecular meshwork of an eye with another glaucoma stent extending from the anterior chamber of the eye, through the trabecular meshwork, and into a rear wall of the Schlemm's canal.
Figure 33:
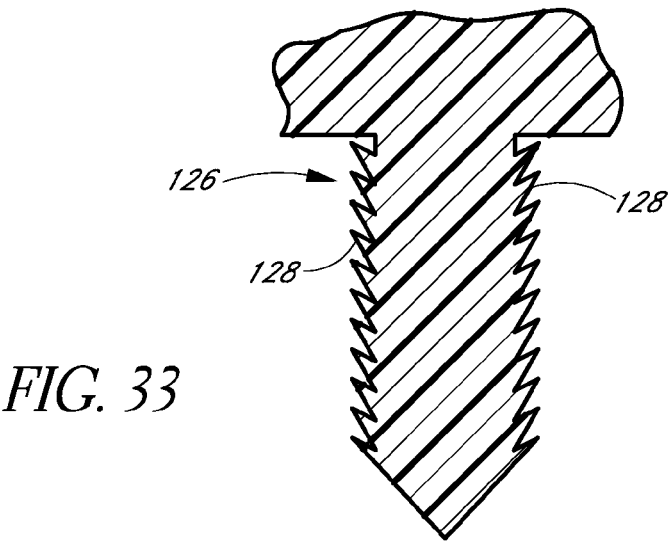
FIG. 33 is an enlarged cross-sectional view of a distal portion of the stent illustrated in FIG. 32.

FIGS. 32 and 33 illustrate a glaucoma stent device 30*f* having features and advantages in accordance with one embodiment. This embodiment of the trabecular stent 30*f* includes a barbed or threaded screw-like extension or pin 126 with barbs 128 for anchoring. The barbed pin 126 extends from a distal or base portion 130 of the stent 30*f*.

In use, the stent 30*f* (FIG. 32) is advanced through the trabecular meshwork 21 and across Schlemm's canal 22. The barbed (or threaded) extension 126 penetrates into the back wall 92 of Schlemm's canal 22 up to the shoulder or base 130 that then rests on the back wall 92 of the canal 22. The combination of a shoulder 130 and a barbed pin 126 of a particular length limits the penetration depth of the barbed pin 126 to a predetermined or preselected distance. In one embodiment, the length of the pin 126 is about 0.5 mm or less. Advantageously, this barbed configuration provides a secure anchoring of the stent 30*f*. As discussed above, correct orientation of the stent 30*f* is ensured by appropriate fiducial marks, indicia or the like and by positioning of the stent in a preloaded applicator.

Referring to FIG. 32, the aqueous flows from the anterior chamber 20, through the lumen 42*f*, then out through two side-ports 56*f* to be directed in both directions along Schlemm's canal 22. Alternatively, flow could be directed in only one direction through a single side-port 56*f*. In other embodiments, more then two outlet ports 56*f*, for example, six to eight ports (like a pin wheel configuration), may be efficaciously used, as needed or desired.

Still referring to FIG. 32, in one embodiment, the stent 30*f* is inserted through a previously made incision in the trabecular meshwork 21. In other embodiments, the stent 30*f* may be combined with any of the blade configurations taught or suggested herein to provide self-trephining capability. In these cases, the incision through the trabecular meshwork 21 is made by the self-trephining stent device that has a blade at its base or proximate to the base.

Deeply Threaded Stent

Figure 34:
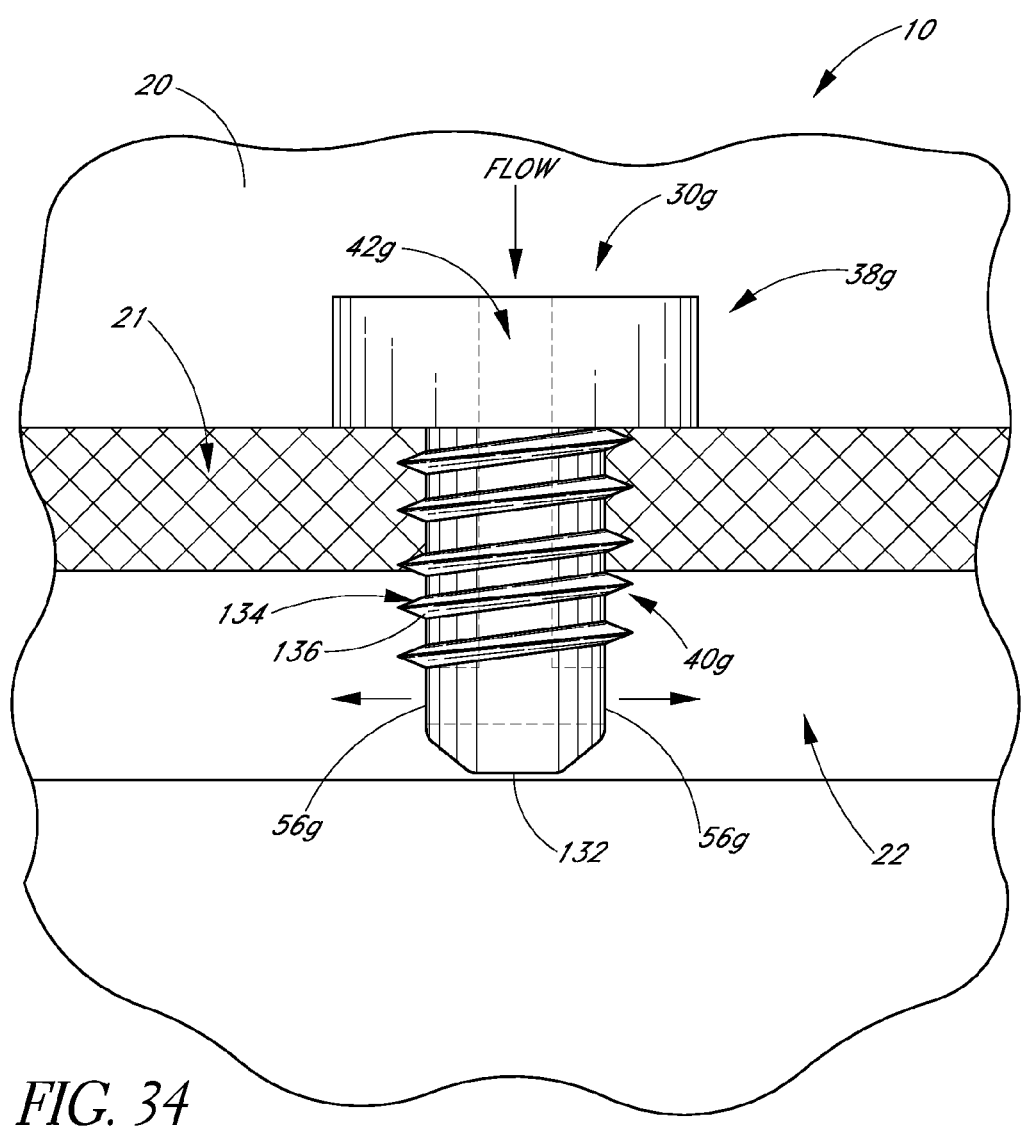
FIG. 34 is a schematic and partial sectional view of the eye of FIG. 32 and a side elevational view of a modification of the stent illustrated in FIG. 32.

FIG. 34 illustrates a glaucoma stent device 30*g* having features and advantages in accordance with one embodiment. The stent 30*g* has a head or seat 38*g* and a shank or main body portion 40*g* with a base or distal end 132. This embodiment of the trabecular stent 30*g* includes a deep thread 134 (with threads 136) on the main body 40*g* of the stent 30*g* below the head 38*g*. The threads may or may not extend all the way to the base 132.

In use, the stent 30*g* (FIG. 34) is advanced through the meshwork 21 through a rotating motion, as with a conventional screw. Advantageously, the deep threads 136 provide retention and stabilization of the stent 30*g* in the trabecular meshwork 21.

Referring to FIG. 34, the aqueous flows from the anterior chamber 20, through the lumen 42*g*, then out through two side-ports 56*g* to be directed in both directions along Schlemm's canal 22. Alternatively, flow could be directed in only one direction through a single side-port 56*g*. In other embodiments, more then two outlet ports 56*g* may be efficaciously used, as needed or desired.

One suitable applicator or delivery apparatus for this stent 30*g* (FIG. 34) includes a preset rotation, for example, via a wound torsion spring or the like. The rotation is initiated by a release trigger on the applicator. A final twist of the applicator by the surgeon and observation of suitable fiducial marks, indicia or the like ensure proper alignment of the side ports 56*g* with Schlemm's canal 22.

Referring to FIG. 34, in one embodiment, the stent 30*g* is inserted through a previously made incision in the trabecular meshwork 21. In other embodiments, the stent 30g may be combined with any of the blade configurations taught or suggested herein to provide self-trephining capability. In these cases, the incision through the trabecular meshwork 21 is made by the self-trephining stent device that has a blade at its base or proximate to the base.

Rivet Style Stent

Figure 35:
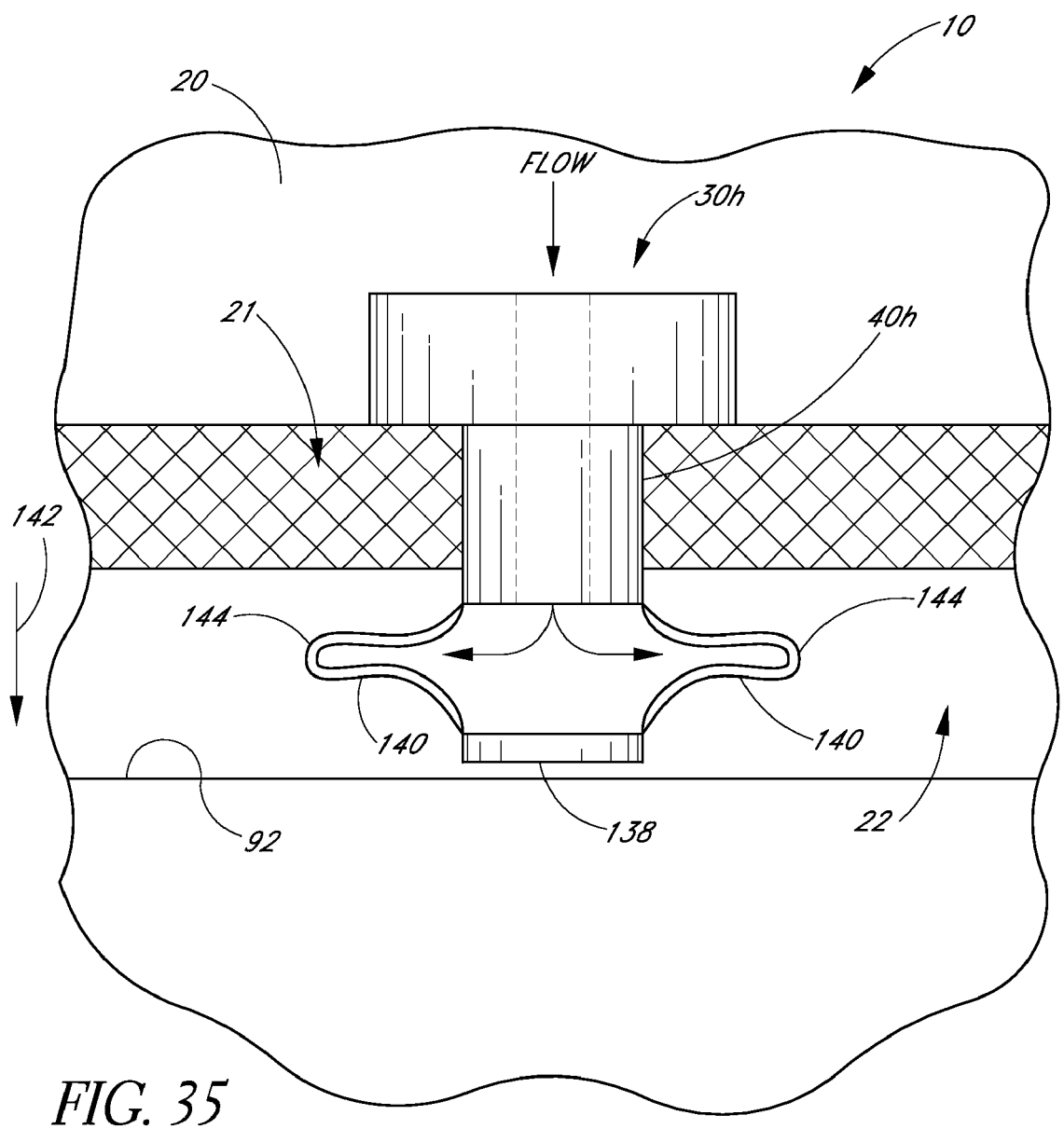
FIG. 35 is a schematic and partial sectional view of the eye illustrated in FIG. 32, and a side elevational view of a photo-modification of the stent illustrated in FIG. 32.

FIG. 35 illustrates a glaucoma stent device 30h having features and advantages in accordance with one embodiment. The stent has a base or distal end 138. This embodiment of the trabecular stent 30h has a pair of flexible ribs 140. In the unused state, the ribs are initially generally straight (that is, extend in the general direction of arrow 142).

Referring to FIG. 35, upon insertion of the stent 30h through the trabecular meshwork 21, the ends 144 of respective ribs 140 of the stent 30h come to rest on the back wall 92 of Schlemm's canal 22. Further advancement of the stent 30h causes the ribs 140 to deform to the bent shape as shown in the drawing of FIG. 35. The ribs 140 are designed to first buckle near the base 138 of the stent 30h. Then the buckling point moves up the ribs 140 as the shank part 40h of the stent 30h is further advanced through the trabecular meshwork 21.

The lumen 42h (FIG. 35) in the stent 30h is a simple straight hole. The aqueous flows from the anterior chamber 20, through the lumen 42h, then out around the ribs 140 to the collector channels further along Schlemm's canal 22 in either direction.

Referring to FIG. 35, in one embodiment, the stent 30h is inserted through a previously made incision in the trabecular meshwork 21. In other embodiments, the stent 30h may be combined with any of the blade configurations taught or suggested herein to provide self-trephining capability. In these cases, the incision through the trabecular meshwork 2.1 is made by the self-trephining stent device that has a blade at its base or proximate to the base.

Grommet Style Stent

Figure 36:
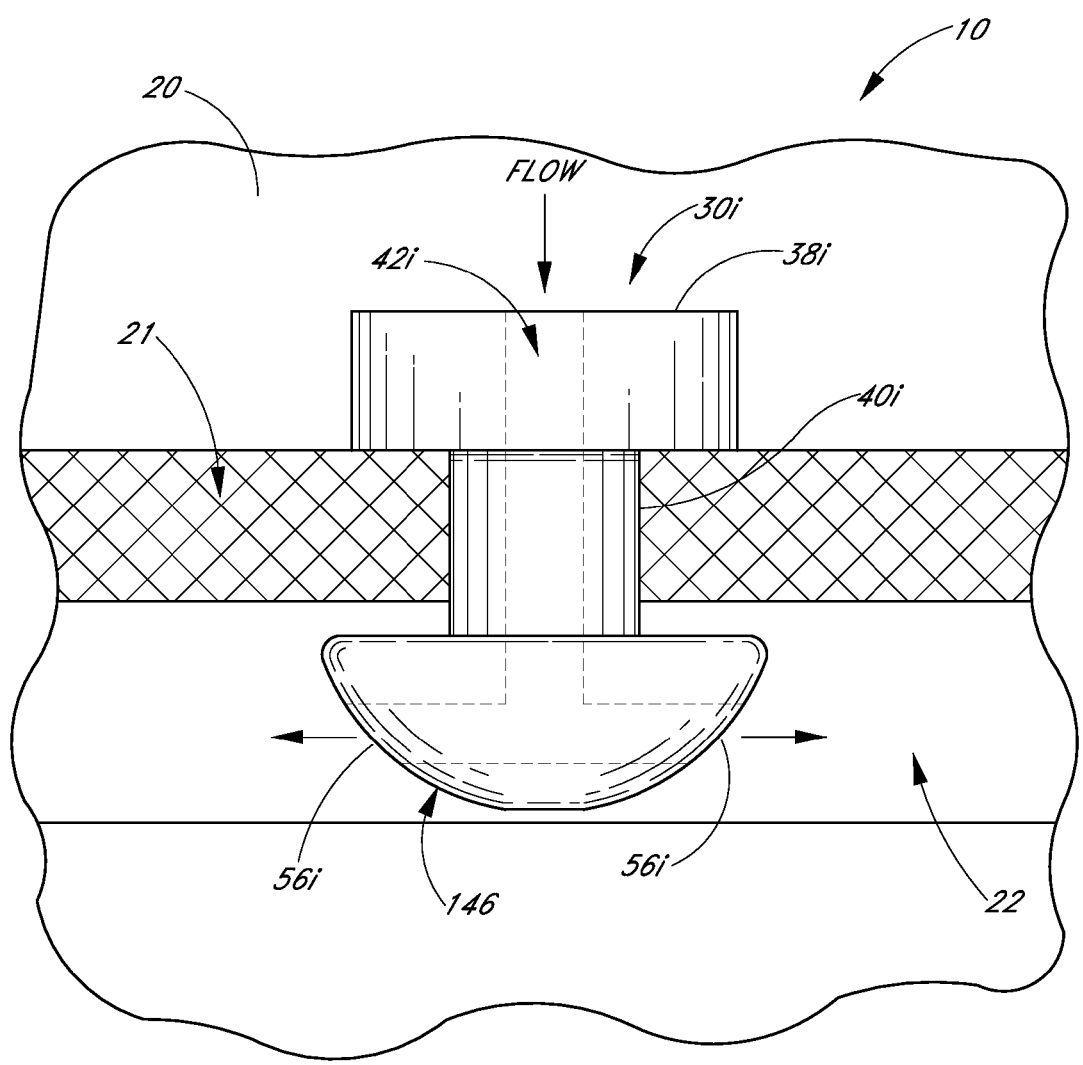
FIG. 36 is a schematic and partial sectional view of the eye illustrated in FIG. 32, and a side elevational view of another modification of the stent of FIG. 32.

FIG. 36 illustrates a glaucoma stent device 30i having features and advantages in accordance with one embodiment. This embodiment of the trabecular stent 30i includes a head or seat 38i, a tapered base portion 146 and an intermediate narrower waist portion or shank 40i.

In use, the stent 30i (FIG. 36) is advanced through the trabecular meshwork 21 and the base 146 is pushed into Schlemm's canal 22. The stent 30i is pushed slightly further, if necessary, until the meshwork 21 stretched by the tapered base 146 relaxes back and then contracts to engage the smaller diameter portion waist 40i of the stent 30i. Advantageously, the combination of the larger diameter head or seat 38i and base 146 of the stent 30i constrains undesirable stent movement. As discussed above, correct orientation of the stent 30i is ensured by appropriate fiducial marks, indicia or the like and by positioning of the stent in a preloaded applicator.

Referring to FIG. 36, the aqueous flows from the anterior chamber 20, through the lumen 42i, then out through two side-ports 56i to be directed in both directions along Schlemm's canal 22. Alternatively, flow could be directed in only one direction through a single side-port 56i. In other embodiments, more then two outlet ports 56i may be efficaciously used, as needed or desired.

Still referring to FIG. 36, in one embodiment, the stent 30i is inserted through a previously made incision in the trabecular meshwork 21. In other embodiments, the stent 30i may be combined with any of the blade configurations taught or suggested herein to provide self-trephining capability. In these cases, the incision through the trabecular meshwork 21 is made by the self-trephining stent device, which has a blade at its base or proximate to the base.

Biointeractive Stent

Figure 37:
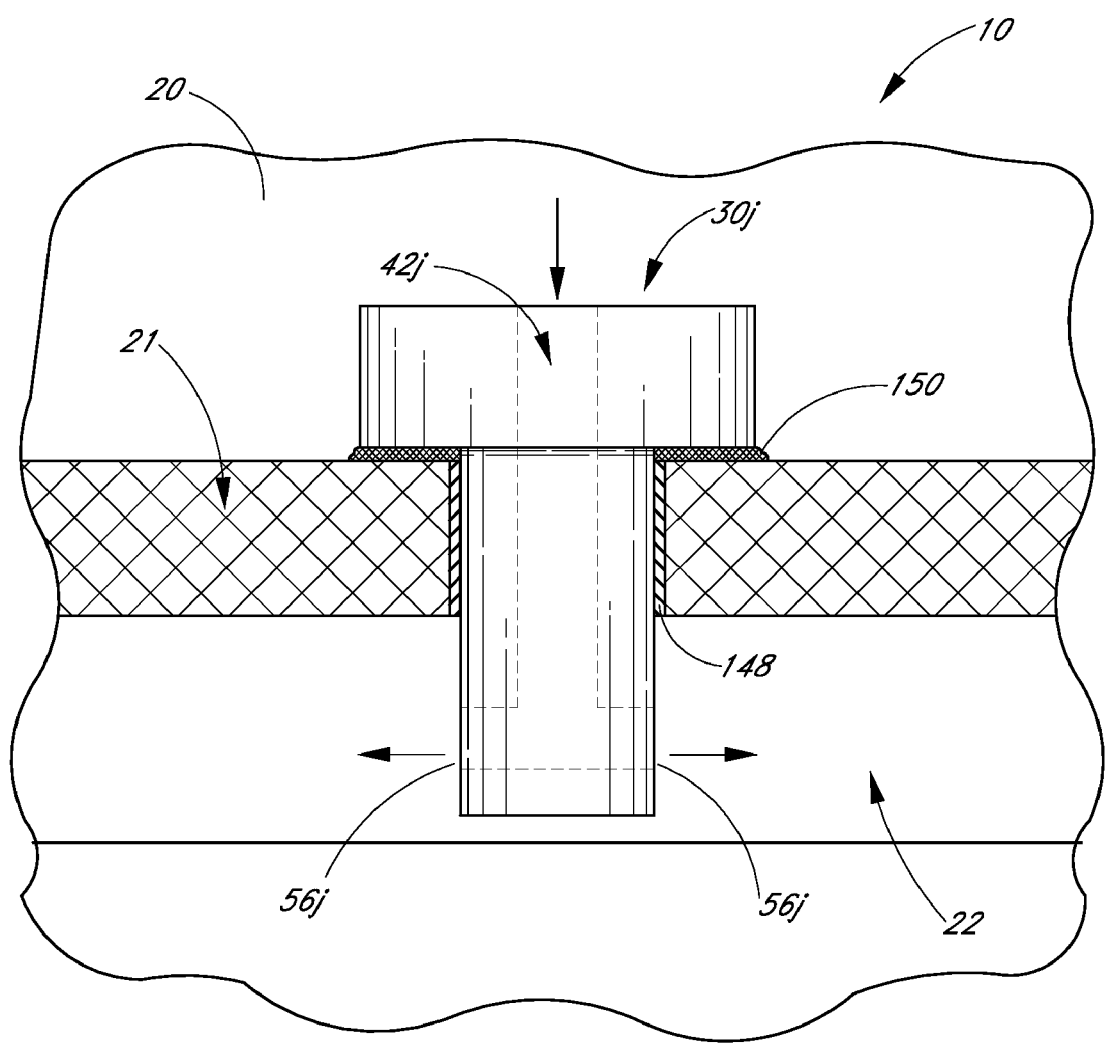
FIG. 37 is a schematic and partial sectional view of the eye illustrated in FIG. 32, and a side elevational view of a further modification of the implant illustrated in FIG. 32.

FIG. 37 illustrates a glaucoma stent device 30j having features and advantages in accordance with one embodiment. This embodiment of the trabecular stent 30j utilizes a region of biointeractive material 148 that provides a site for the trabecular meshwork 21 to firmly grip the stent 30j by ingrowth of the tissue into the biointeractive material 148. As shown in FIG. 37, preferably the biointeractive layer 148 is applied to those surfaces of the stent 30j, which would abut against or come in contact with the trabecular meshwork 21.

In one embodiment, the biointeractive layer 148 (FIG. 37) may be a region of enhanced porosity with a growth promoting chemical. In one embodiment, a type of bio-glue 150 that dissolves over time is used to hold the stent secure during the time between insertion and sufficient ingrowth for stabilization. As discussed above, correct orientation of the stent 30j is ensured by appropriate fiducial marks, indicia or the like and by positioning of the stent in a preloaded applicator.

Referring to FIG. 37, the aqueous flows from the anterior chamber 20, through the lumen 42j, then out through two side-ports 56j to be directed in both directions along Schlemm's canal 22. Alternatively, flow could be directed in only one direction through a single side-port 56j. In other embodiments, more then two outlet ports 56j may be efficaciously used, as needed or desired.

Still referring to FIG. 37, in one embodiment, the stent 30j is inserted through a previously made incision in the trabecular meshwork 21. In other embodiments, the stent 30j may be combined with any of the blade configurations taught or suggested herein to provide self-trephining capability. In these cases, the incision through the trabecular meshwork 21 is made by the self-trephining stent device, which has a blade at its base or proximate to the base.

Glued or Welded Stent

Figure 38:
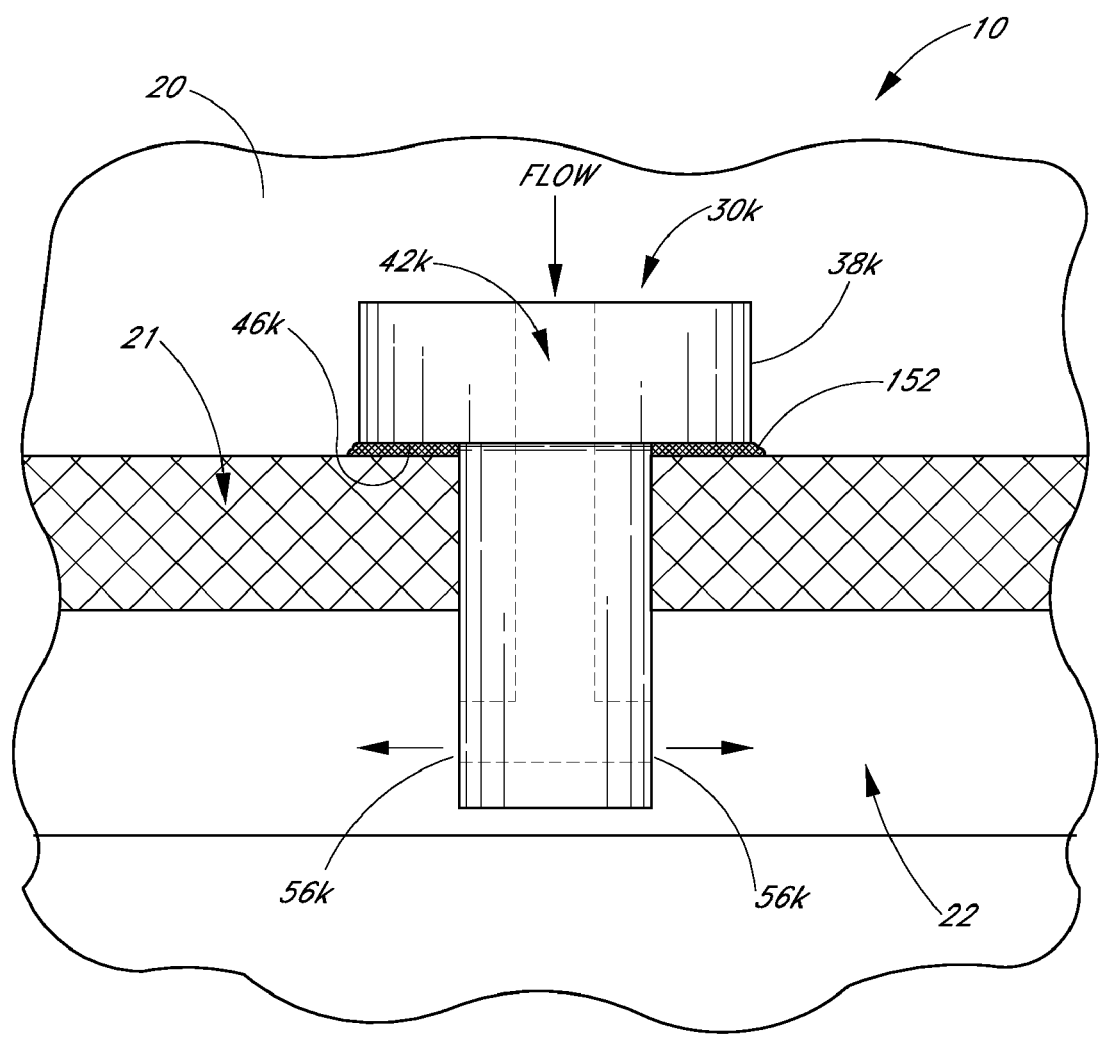
FIG. 38 is a schematic and partial sectional view of the eye illustrated in FIG. 32 and a side elevational view of another modification of the stent illustrated in FIG. 32.

FIG. 38 illustrates a glaucoma stent device 30k having features and advantages in accordance with one embodiment. This embodiment of the trabecular stent 30k is secured in place by using a permanent (non-dissolving) bio-glue 152 or a "welding" process (e.g., heat) to form a weld 152. The stent 30k has a head or seat 38k and a lower surface 46k.

The stent 30k is advanced through the trabecular meshwork 21 until the head or seat 38k comes to rest on the trabecular meshwork 21, that is, the head lower surface 46k abuts against the trabecular meshwork 21, and the glue or weld 152 is applied or formed therebetween, as shown in FIG. 38. As discussed above, correct orientation of the stent 30k is ensured by appropriate fiducial marks, indicia or the like and by positioning of the stent in a preloaded applicator.

Referring to FIG. 38, the aqueous flows from the anterior chamber 20, through the lumen 42k, then out through two side-ports 56k to be directed in both directions along Schlemm's canal 22. Alternatively, flow could be directed in only one direction through a single side-port 56k. In other embodiments, more then two outlet ports 56k may be efficaciously used, as needed or desired.

Still referring to FIG. 38, in one embodiment, the stent 30k is inserted through a previously made incision in the trabecular meshwork 21. In other embodiments, the stent 30k may be combined with any of the blade configurations taught or suggested herein to provide self-trephining capability. In these cases, the incision through the trabecular meshwork 21 is made by the self-trephining stent device, which has a blade at its base or proximate to the base.

Hydrophilic Latching Stent

Figure 39:
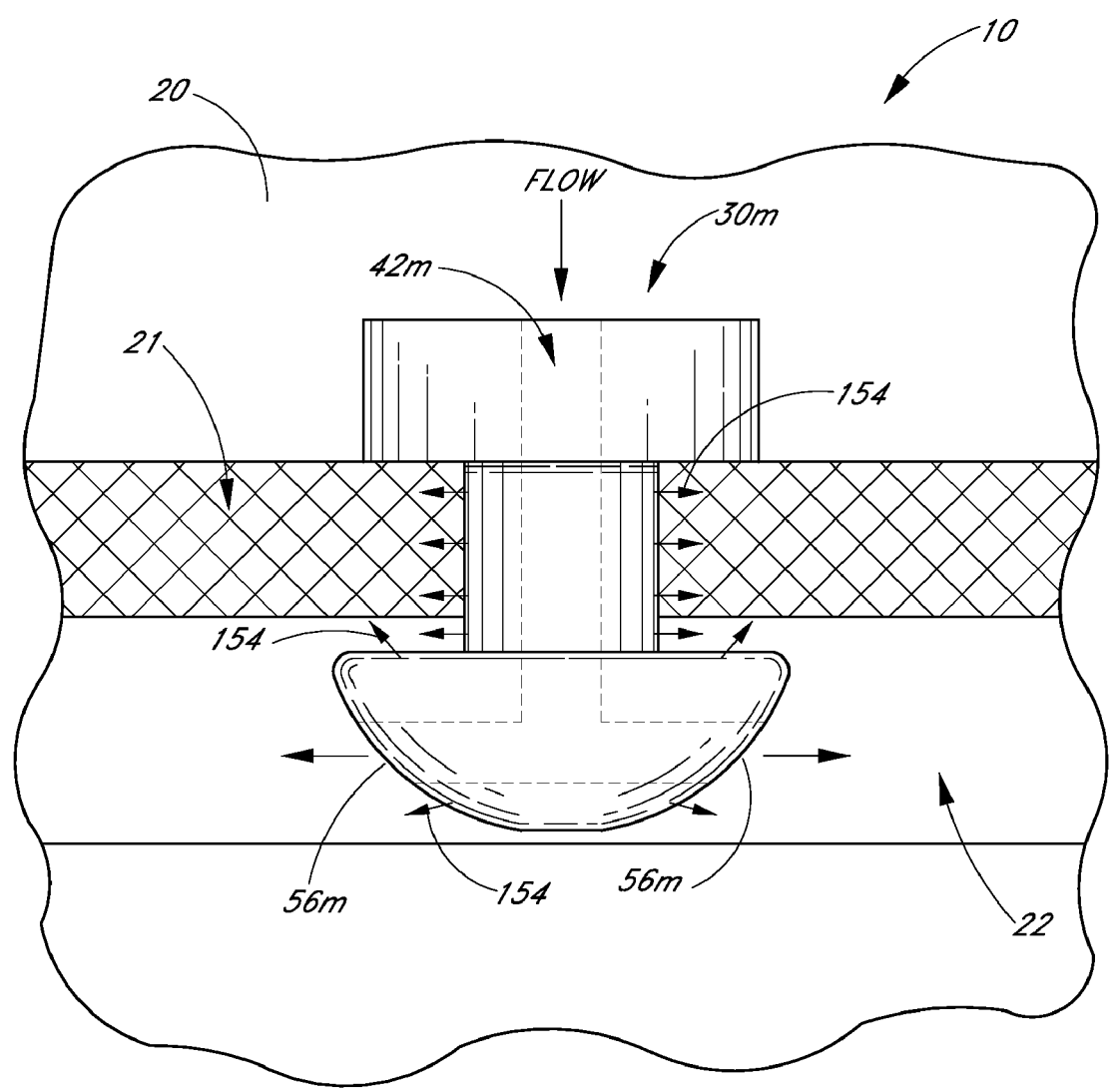
FIG. 39 is a schematic and partial sectional view of the eye illustrated in FIG. 32, and a side elevational view of the further modification of the implant illustrated in FIG. 32.

FIG. 39 illustrates a glaucoma stent device 30m having features and advantages in accordance with one embodiment. This embodiment of the trabecular stent 30m is fabricated from a hydrophilic material that expands with absorption of water. Desirably, this would enable the device 30m to be inserted through a smaller incision in the trabecular meshwork 21. The subsequent expansion (illustrated by the smaller arrows 154) of the stent 30m would advantageously enable it to latch in place in the trabecular meshwork 21. As discussed above, correct orientation of the stent 30m is ensured by appropriate fiducial marks, indicia or the like and by positioning of the stent in a preloaded applicator.

Referring to FIG. 39, the aqueous flows from the anterior chamber 20, through the lumen 42m, then out through two side-ports 56m to be directed in both directions along Schlemm's canal 22. Alternatively, flow could be directed in only one direction through a single side-port 56m. In other embodiments, more then two outlet ports 56m may be efficaciously used, as needed or desired.

Still referring to FIG. 39, in one embodiment, the stent 30m is inserted through a previously made incision in the trabecular meshwork 21. In other embodiments, the stent 30m may be combined with any of the blade configurations taught or suggested herein to provide self-trephining capability. In these cases, the incision through the trabecular meshwork 21 is made by the self-trephining stent device, which has a blade at its base or proximate to the base.

Photodynamic Stent

Figure 40:
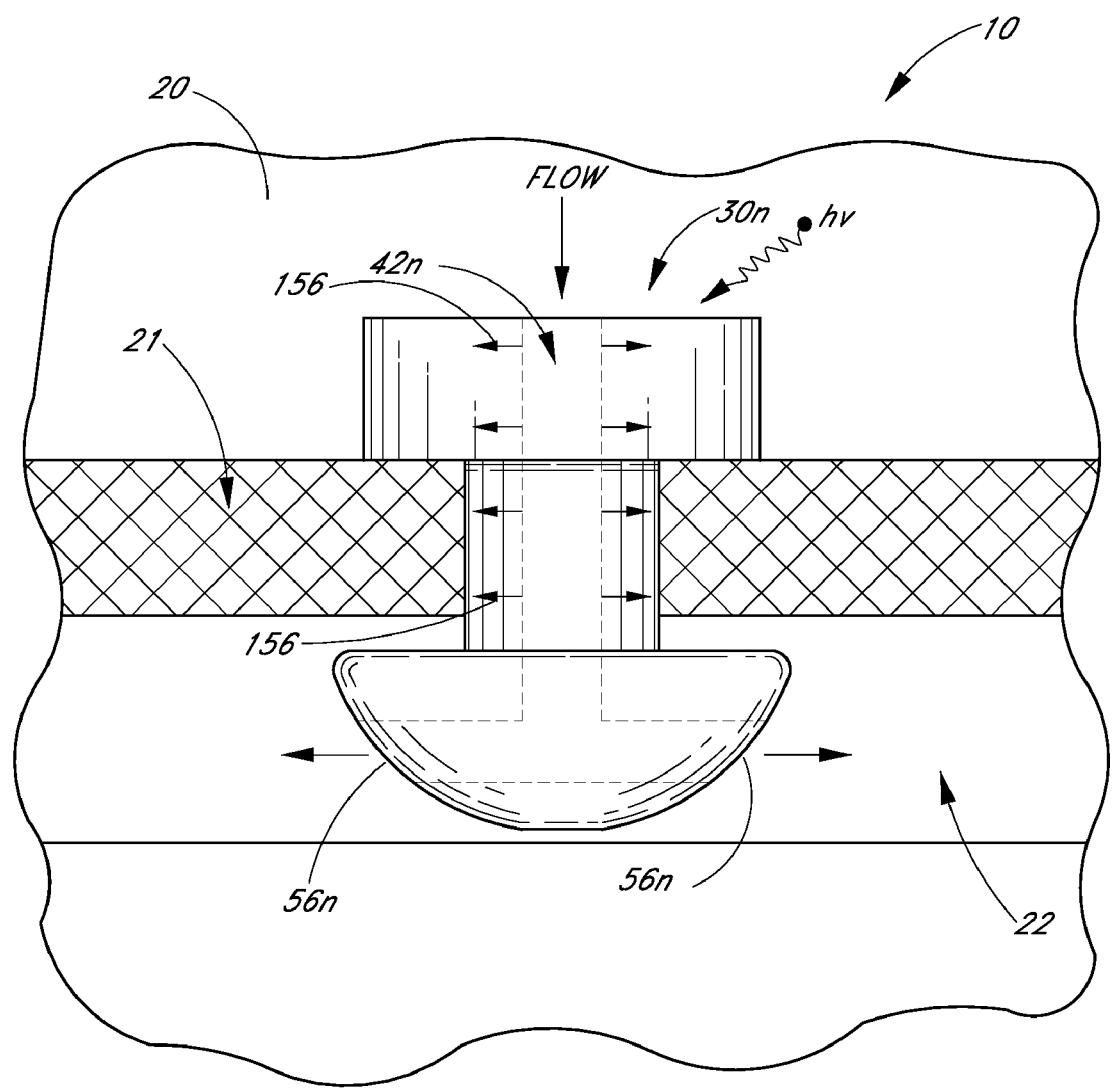
FIG. 40 is a schematic and partial sectional view of the eye illustrated in FIG. 32, and a side elevational view of yet another modification of the stent illustrated in FIG. 32.

FIG. 40 illustrates a glaucoma stent device 30n having features and advantages in accordance with one embodiment. This embodiment of the trabecular stent 30n is fabricated from a photodynamic material that expands on exposure to light.

It is commonly known that there is a diurnal variation in the aqueous humor production by the eye—it is higher during the day than it is at night. The lumen 42n of the stent 30n responds to light entering the cornea during the day by expanding and allowing higher flow of aqueous through the lumen 42n and into Schlemm's canal 22. This expansion is generally indicated by the smaller arrows 156 (FIG. 40) which show the lumen 42n (and ports) expanding or opening in response to light stimulus. (The light or radiation energy E is generally given by E=hv, where h is Planck's constant and v is the frequency of the light provided.) At night, in darkness, the lumen diameter decreases and reduces the flow allowed through the lumen 42n. In one embodiment, an excitation wavelength that is different from that commonly encountered is provided on an as-needed basis to provide higher flow of aqueous to Schlemm's canal 22.

This photodynamic implementation is shown in FIG. 40 for the self-latching style of stent 30n, but can be efficaciously used with any of the other stent embodiments, as needed or desired. As discussed above, correct orientation of the stent 30n is ensured by appropriate fiducial marks, indicia or the like and by positioning of the stent in a preloaded applicator.

Referring to FIG. 40, the aqueous flows from the anterior chamber 20, through the lumen 42n, then out through two side-ports 56n to be directed in both directions along Schlemm's canal 22. Alternatively, flow could be directed in only one direction through a single side-port 56n. In other embodiments, more then two outlet ports 56n may be efficaciously used, as needed or desired.

Still referring to FIG. 40, in one embodiment, the stent 30n is inserted through a previously made incision in the trabecular meshwork 21. In other embodiments, the stent 30n may be combined with any of the blade configurations taught or suggested herein to provide self-trephining capability. In these cases, the incision through the trabecular meshwork 21 is made by the self-trephining stent device, which has a blade at its base or proximate to the base.

Collector Channel Alignment Stent

Figure 41:
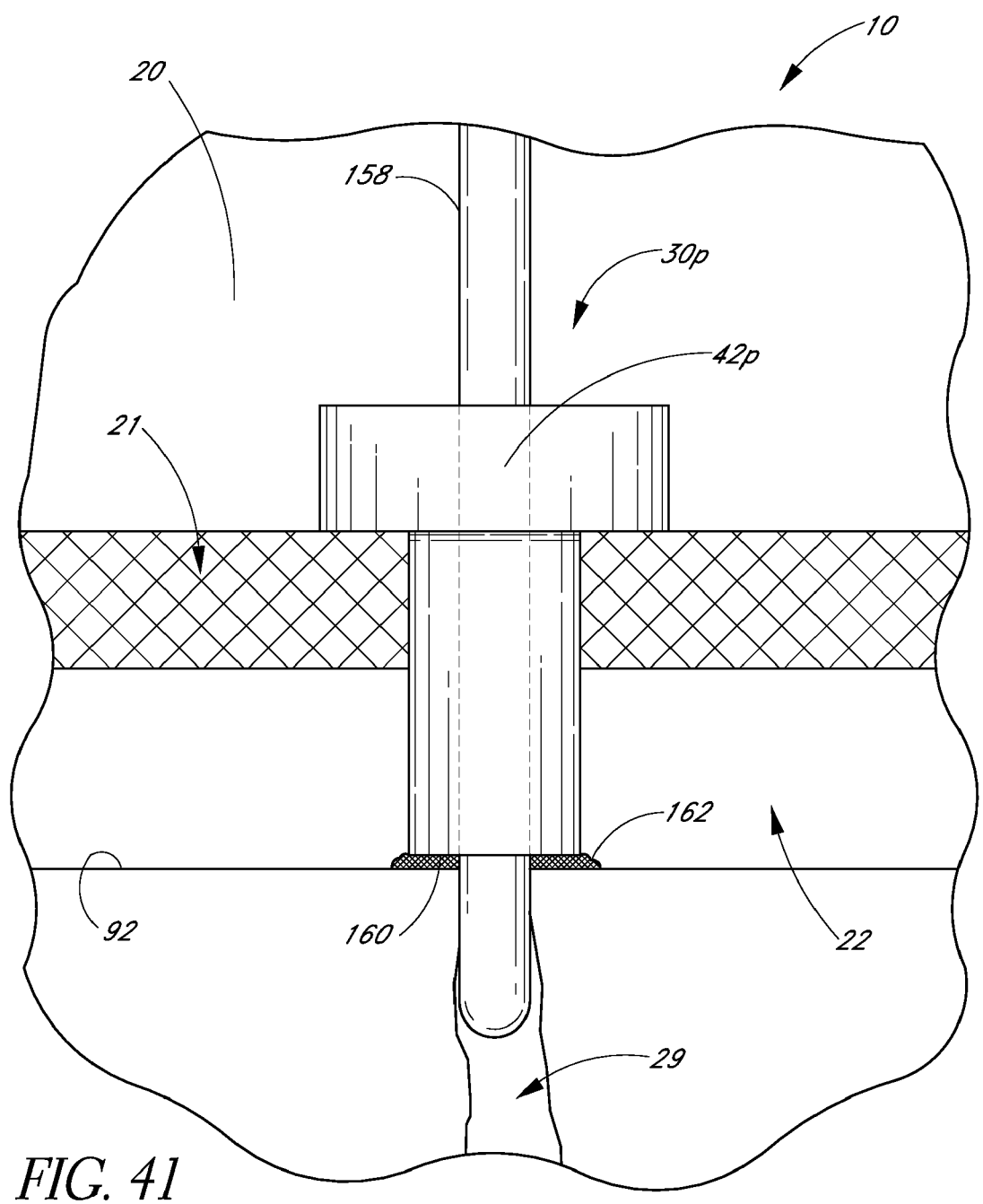
FIG. 41 is a schematic and partial sectional view of an eye and the side elevational view of yet another modification of the stent illustrated in FIG. 32.

FIG. 41 illustrates a glaucoma stent device 30p having features and advantages in accordance with one embodiment. This figure depicts an embodiment of a stent 30p that directs aqueous from the anterior chamber 20 directly into a collector channel 29, which empties into aqueous veins. The stent 30p has a base or distal end 160.

In the illustrated embodiment of FIG. 41, a removable alignment pin 158 is utilized to align the stent lumen 42p with the collector channel 29. In use, the pin 158 extends through the stent lumen 42p and protrudes through the base 160 and extends into the collector channel 29 to center and/or align the stent 30p over the collector channel 29. The stent 30p is then pressed firmly against the back wall 92 of Schlemm's canal 22. A permanent bio-glue 162 is used between the stent base and the back wall 92 of Schlemm's canal 22 to seat and securely hold the stent 30p in place. Once positioned, the pin 158 is withdrawn from the lumen 42p to allow the aqueous to flow directly from the anterior chamber 20 into the collector duct 29. The collector ducts are nominally 20 to 100 micrometers (μm) in diameter and are visualized with a suitable microscopy method (such as ultrasound biomicroscopy (UBM)) or laser imaging to provide guidance for placement of the stent 30p.

Referring to FIG. 41, in one embodiment, the stent 30p is inserted through a previously made incision in the trabecular meshwork 21. In other embodiments, the stent 30p may be combined with any of the blade configurations taught or suggested herein to provide self-trephining capability. In these cases, the incision through the trabecular meshwork 21 is made by the self-trephining stent device, which has a blade at its base or proximate to the base.

Barbed Stent (Anterior Chamber to Collector Channel)

Figure 42:
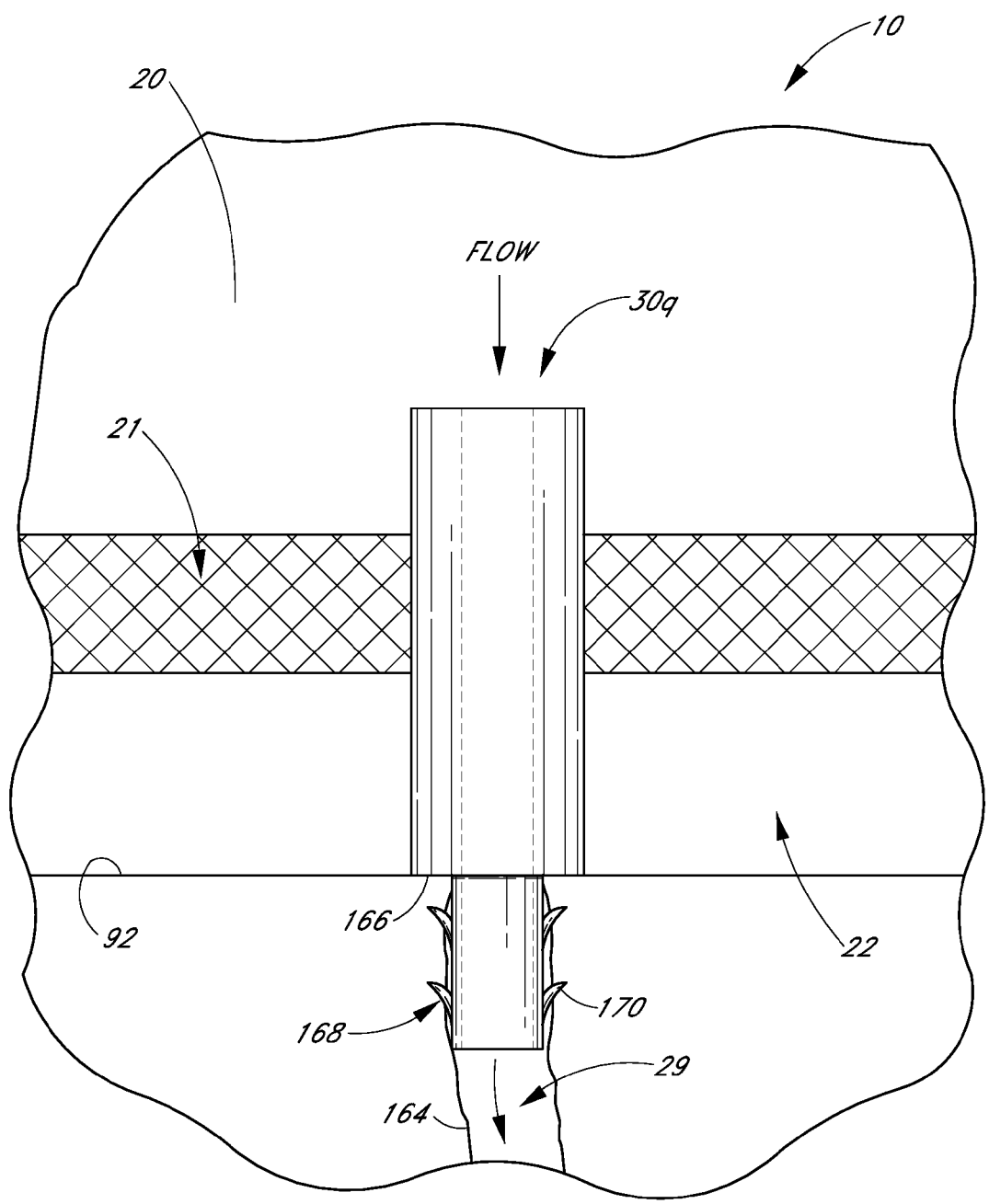
FIG. 42 is a schematic and partial sectional view of the eye illustrated in FIG. 32, and a side elevational view of yet another modification of the implant illustrated in FIG. 32.

FIG. 42 illustrates a glaucoma stent device 30q having features and advantages in accordance with one embodiment. This figure depicts an embodiment of a stent 30q that directs aqueous from the anterior chamber 20 directly into a collector channel 29, which empties into aqueous veins. The stent 30q has a base or distal end 166 and the channel 29 has wall(s) 164.

In the illustrated embodiment of FIG. 42, a barbed, small-diameter extension or pin 168 on the stent base 166 is guided into the collector channel 29 and anchors on the wall(s) 164 of the channel 29. The pin 168 has barbs 170 which advantageously provide anchoring of the stent 30q. The collector ducts 29 are nominally 20 to 100 micrometers (μm) in diameter and are visualized with a suitable microscopy method (such as ultrasound biomicroscopy (UBM)) or laser imaging to provide guidance for placement of the stent.

Referring to FIG. 42, in one embodiment, the stent 30q is inserted through a previously made incision in the trabecular meshwork 21. In other embodiments, the stent 30q may be combined with any of the blade configurations taught or suggested herein to provide self-trephining capability. In these cases, the incision through the trabecular meshwork 21 is made by the self-trephining stent device, which has a blade at its base or proximate to the base.

Valved Tube Stent (Anterior Chamber to Choroid)

Figure 43:
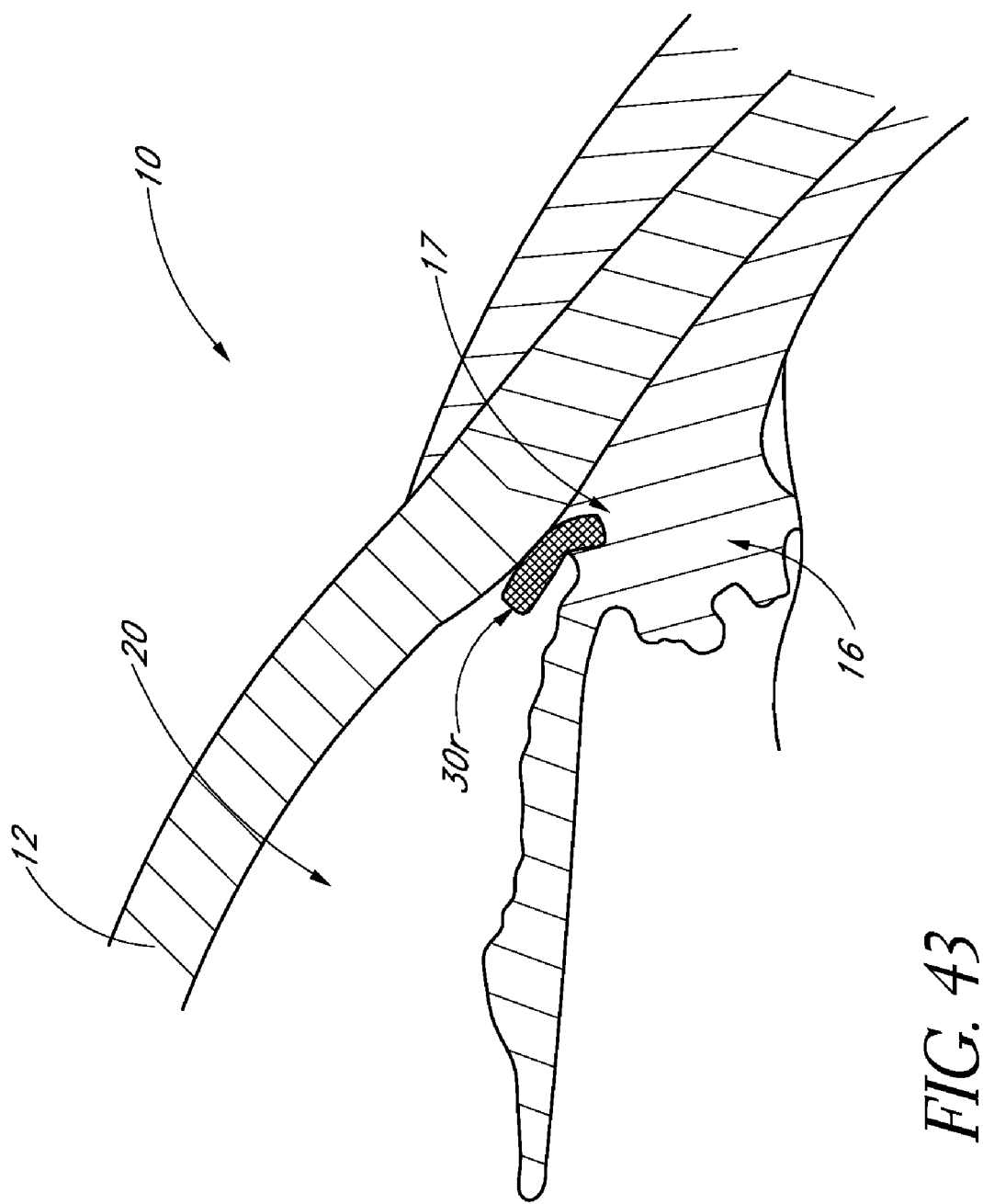
FIG. 43 is an enlarged schematic and partial cross-sectional view of an anterior chamber angle of an eye having a valve stent implanted therein.

FIG. 43 illustrates a valved tube stent device 30r having features and advantages in accordance with one embodiment. This is an embodiment of a stent 30r that provides a channel for flow between the anterior chamber 20 and the highly vascular choroid 17. Clinically, the choroid 17 can be at pressures lower than those desired for the eye 10. Therefore, this stent 30r includes a valve with an opening pressure equal to the desired pressure difference between the choroid 17 and the anterior chamber 10 or a constriction that provide the desired pressure drop.

Osmotic Membrane (Anterior Chamber to Choroid)

Figure 44:
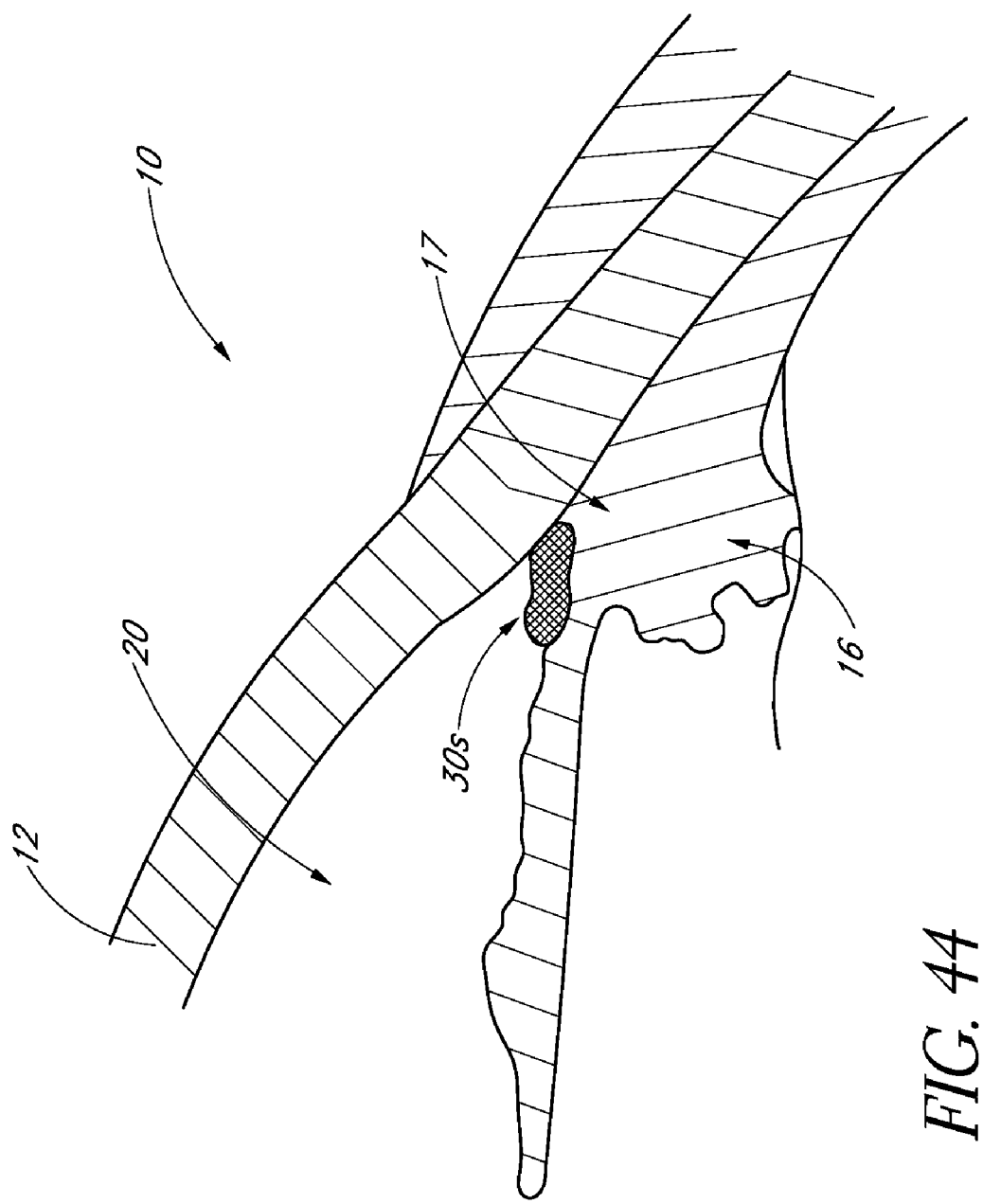
FIG. 44 is an enlarged cross-sectional view of an anterior chamber angle of an eye including an osmotic membrane device implanted therein.

FIG. 44 illustrates a osmotic membrane device 30s having features and advantages in accordance with one embodiment. This embodiment provides a channel for flow between the anterior chamber 20 and the highly vascular choroid 17. The osmotic membrane 30s is used to replace a portion of the endothelial layer of the choroid 17. Since the choroid 17 is highly vascular with blood vessels, the concentration of water on the choroid side is lower than in the anterior chamber 20 of the eye 10. Therefore, the osmotic gradient drives water from the anterior chamber 20 into the choroid 17.

Clinically, the choroid 17 (FIG. 44) can be at pressures lower than those desired for the eye 10. Therefore, desirably, both osmotic pressure and the physical pressure gradient are in favor of flow into the choroid 17. Flow control is provided by proper sizing of the area of the membrane; the larger the membrane area is the larger the flow rate will be. This advantageously enables tailoring to tune the flow to the desired physiological rates.

Ab Externo Insertion of Stent via Small Puncture

Figure 45:
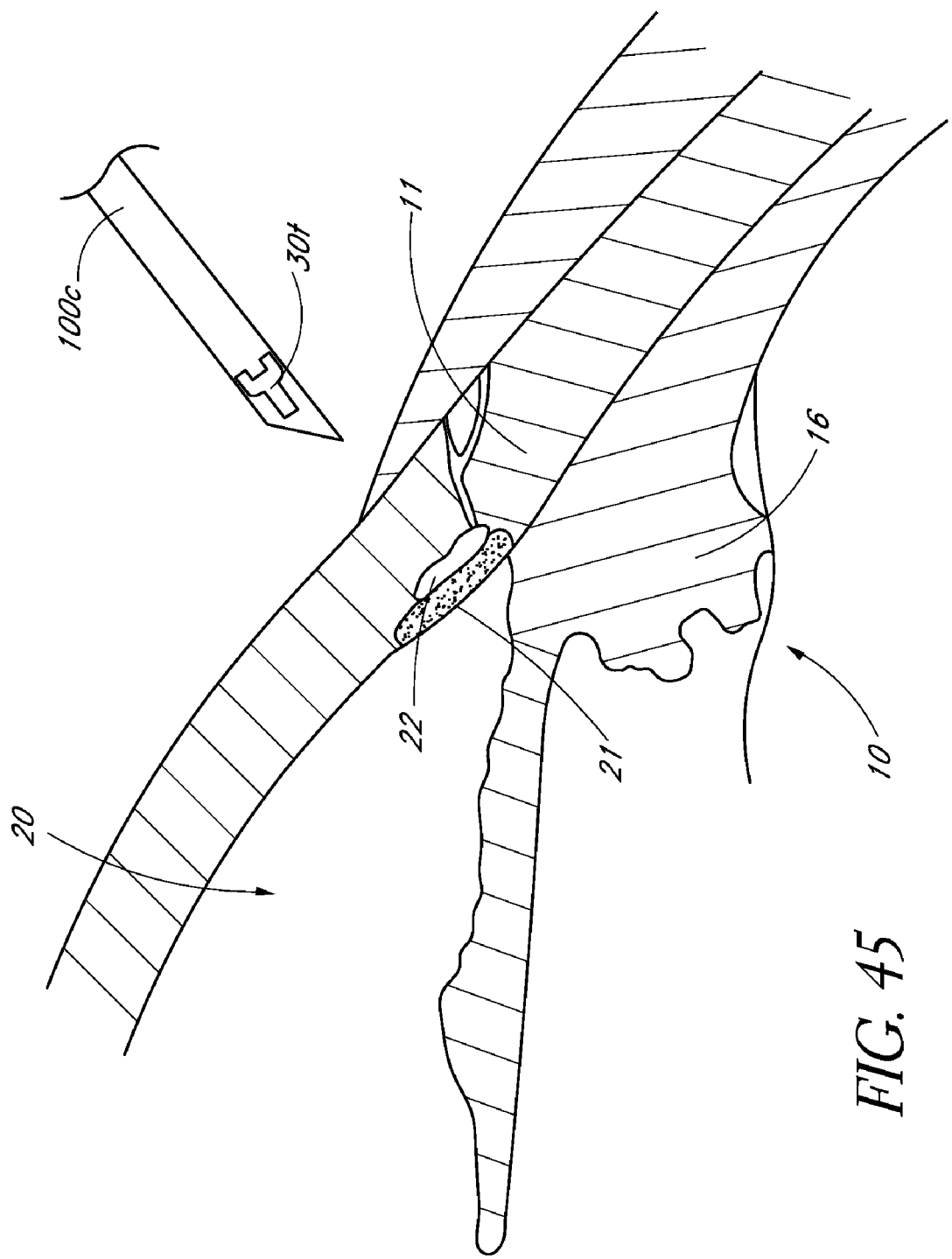
FIG. 45 is an enlarged cross-sectional view of an anterior chamber angle of an eye illustrating an implantation of a glaucoma stent using an ab externo procedure.

FIG. 45 illustrates the implantation of a stent 30t using an ab externo procedure having features and advantages in accordance with one embodiment. In the ab externo procedure of FIG. 45, the stent 30t is inserted into Schlemm's canal 21 with the aid of an applicator or delivery apparatus 100c that creates a small puncture into the eye 10 from outside.

Referring to FIG. 45, the stent 30t is housed in the applicator 100c, and pushed out of the applicator 100c once the applicator tip is in position within the trabecular meshwork 21. Since the tissue surrounding the trabecular meshwork 21 is optically opaque, an imaging technique, such as ultrasound biomicroscopy (UBM) or a laser imaging technique, is utilized. The imaging provides guidance for the insertion of the applicator tip and the deployment of the stent 30t. This technique can be used with a large variety of stent embodiments with slight modifications since the trabecular meshwork 21 is punctured from the scleral side rather than the anterior chamber side in the ab externo insertion.

Figure 46:
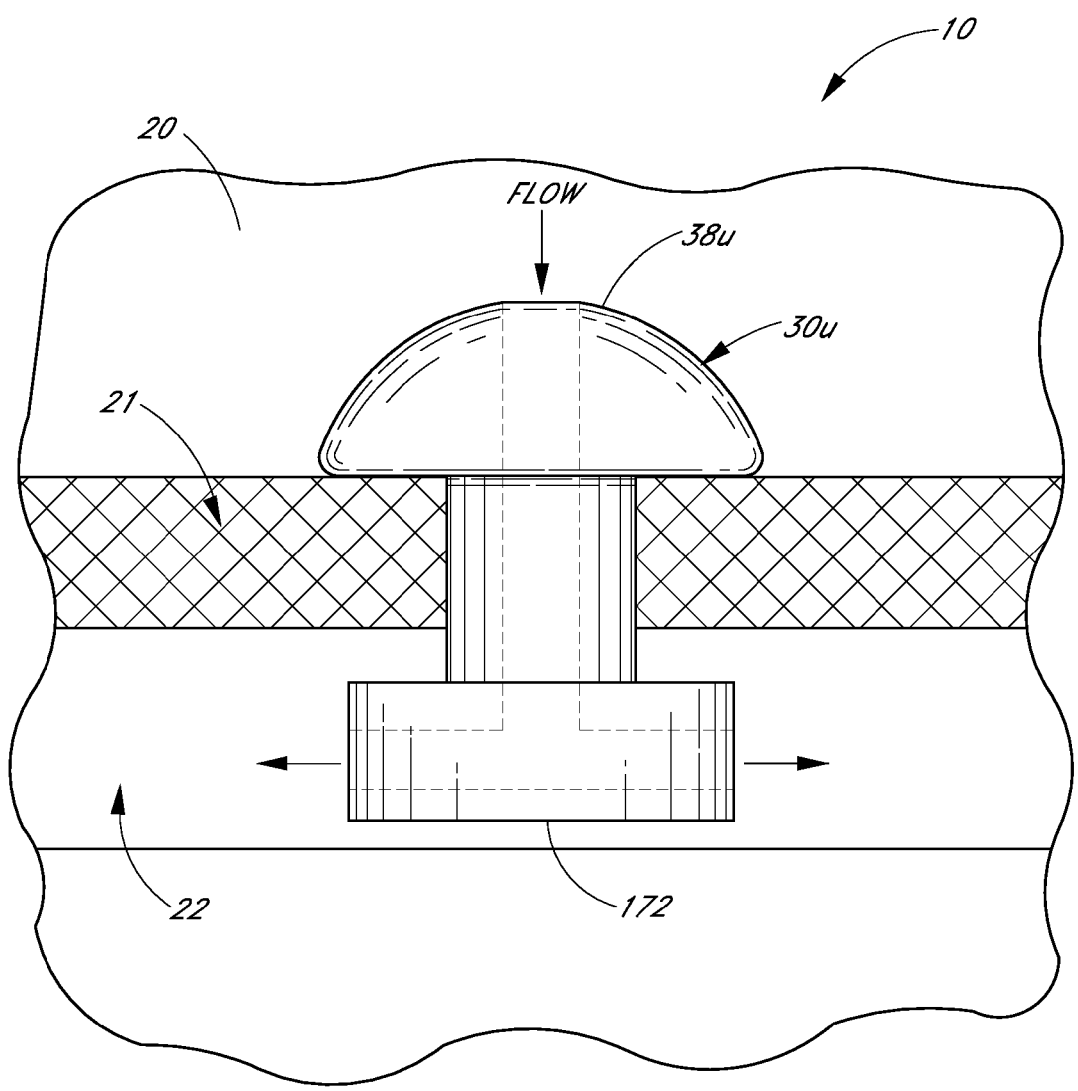
FIG. 46 is a schematic and partial sectional view of the eye illustrated in FIG. 32 and a side elevational view of another modification of the implant illustrated in FIG. 32.

FIG. 46 a glaucoma stent device 30u having features and advantages in accordance with a modified embodiment. This grommet-style stent 30u for ab externo insertion is a modification of the embodiment of FIG. 36. In the embodiment of FIG. 46, the upper part or head 38u is tapered while the lower part or base 172 is flat, as opposed to the embodiment of FIG. 36. The stent 30u is inserted from the outside of the eye 10 through a puncture in the sclera. Many of the other embodiments of stents taught or suggested herein can be modified for similar implantation.

This ultra microscopic device 30u (FIG. 46) can be used with (1) a targeting Lasik-type laser, or with (2) contact on eyes or with (3) combined ultrasound microscope or (4) other device inserter handpiece.

Targeted Drug Delivery to the Trabecular Meshwork

Figure 47:
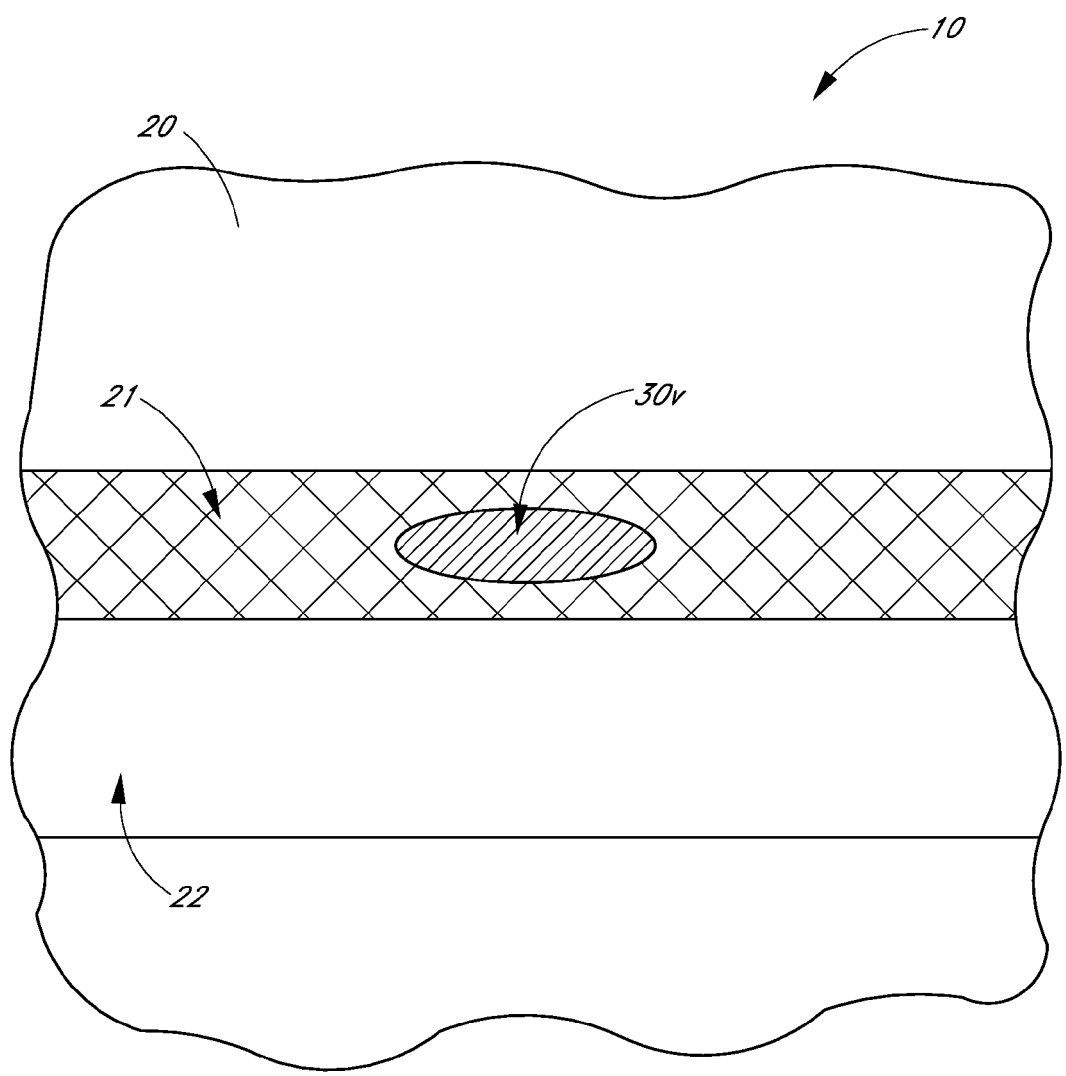
FIG. 47 is an enlarged schematic and partial sectional view of the eye illustrated in FIG. 32 and including a drug release device implanted therein.

FIG. 47 illustrates a targeted drug delivery implant 30v having features and advantages in accordance with one embodiment. This drawing is a depiction of a targeted drug delivery concept. The slow release implant 30v is implanted within the trabecular meshwork 21.

A drug that is designed to target the trabecular meshwork 21 to increase its porosity, or improve the active transport across the endothelial layer of Schlemm's canal 22 can be stored in this small implant 30v (FIG. 47). Advantageously, slow release of the drug promotes the desired physiology at minimal dosage levels since the drug is released into the very structure that it is designed to modify.

Dose Response

The programmed (also know as "Targeted") stent placement refers to the intentional placement of a stent or stents at a particular location or locations in Schlemm's canal for the purpose of providing a benefit in the form of more optimal outflow. For example, a method can be provided which includes assessing the aqueous flow characteristics of an eye. Such characteristics can include, for example, but without limitation, collector channel distribution, collector channel flow characteristics, outflow resistance, outflow capacity, shape/size/tortuosity of Schlemm's canal, and other factors). The method can also include determining an optimal stent placement and implanting stents in one or plurality of positions and procedures. For example, the determination of the desired stent placement can include consideration of a database of cadaver anatomy regarding the number and location of collector channels, the patient's micro-anatomy data, the number of stents to be used, the type of stents to be used, the location of any previously implanted stents whether the desired stent is drug-loaded, gene-loaded or surface treated, and/or any associated drug therapy.

Figure 48:
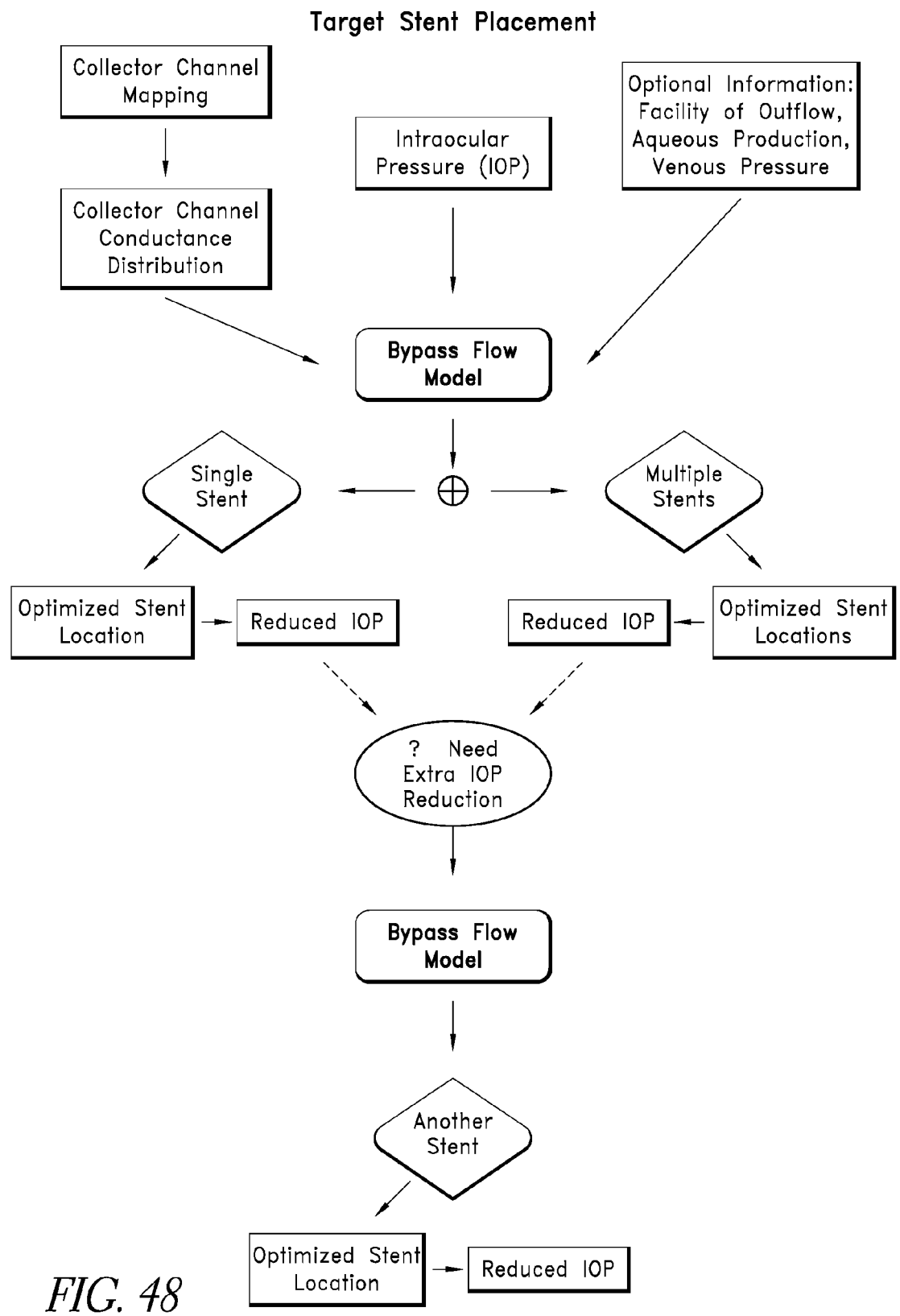
FIG. 48 is a flow diagram illustrating a method for treating glaucoma.

FIG. 48 includes a flow diagram illustrating a decision tree for determining desired stent placement. In the illustrated embodiment, after it is determined that a patient is suffering from excess of intraocular pressure (IOP), a bypass flow model is determined to aid in the decision of whether or not to use single or multiple stents. Optionally, the configuration of collector channels in the patient's eye can be met to aid in the creation of a bypass flow model. Further, other information can be used, such as, for example, but without limitation, outflow resistance, aqueous production, and venous pressure.

The bypass flow model, which can be based on the above-noted information, is determined so as to provide a desired strategy for lowering the excessive intraocular pressure. If it is decided that a single stent should be used, an optimized stent location is first determined based on the bypass flow model. The implantation of the single stent results in reduced IOP. After this implantation, it is again determined if there is a need for further reduction in IOP. If additional IOP reduction is desired, then a further bypass flow model is created. For example, the second bypass flow model can be determined in the same or similar manner as the first bypass flow model described above. In light of the second bypass flow model, an additional stent can be implanted at an optimized location to further reduce IOP.

If it is determined, in light of the first bypass flow model, that multiple stents should be used, the location of the multiple stents is first optimized. Then, the multiple stents are implanted. Afterwards, it is again determined if additional intraocular pressure reduction is needed, and the trimming can continue as noted above.

Where additional stents are implanted in light of the second bypass flow model, the additional stents can be different from the first stents implanted. For example, where single or multiple stents are implanted in accordance with the first bypass flow model, the additional stents can be of a different type. For example, in one embodiment, the first stent is a G1 (First generation) trabecular stent that has been disclosed in copending applications and the second stent(s) is the same G1 trabecular stent. In another embodiment, the second stent(s) is different from the first stent; for example, the second stent is a G2 stent (that is, "injectable axisymmetric stent"; a second generation stent). In still another embodiment, the second stent(s) is smaller than (in some case, larger than) the first stent. The dose response may also relate to the stent configuration or characteristics such as drug-loading or surface treatment enabling enhancing aqueous transport or therapeutic effects on the tissue as needed. Drug-loaded or drug-eluting stent may comprise different types of drugs including, but not limited to, those cited in copending patent application Ser. No. 10/046,137 filed Nov. 8, 2001, entitled DRUG RELEASING TRABECULAR IMPLANT FOR GLAUCOMA TREATMENT, the entire contents of which is hereby incorporated by reference.

Figure 49A:
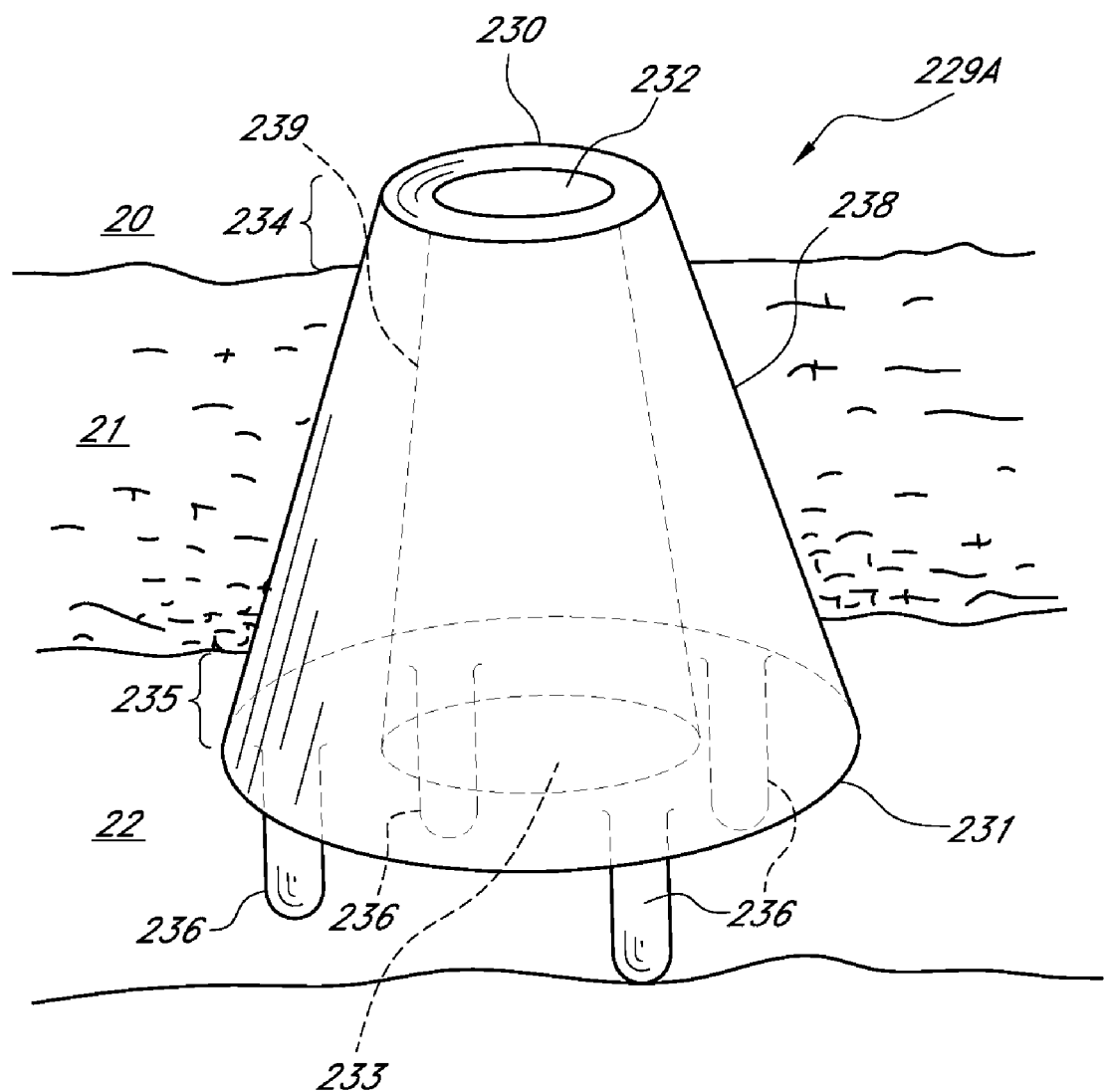
FIG. 49A is an enlarged schematic illustration showing an anterior chamber, trabecular meshwork and a Schlemm's canal of an eye and an oblique elevational view of yet another modification of the stent illustrated in FIG. 32.

With reference to FIG. 49A, a stent extending between an anterior chamber 20 of an eye, through the trabecular meshwork 21, and into Schlemm's canal 22 of an eye can be configured to be axisymmetric with respect to the flow of aqueous therethrough. For example, as shown in FIG. 49A, the stent 229A comprises an inlet end 230 configured to be disposed in the anterior chamber 20. The second end 231 of the stent 229A is configured to be disposed in Schlemm's canal 22.

At least one lumen 239 extends through the stent 229A between the inlet and outlet ends 230, 232. The lumen 239 defines an opening 232 at the inlet end 230 as well as an outlet 233 at the outlet end 231.

In the illustrated embodiment, an exterior surface 238 of the stent 229A is cone-shaped. Thus, a circumference of the exterior surface 238 adjacent to the inlet end 230 is smaller than the circumference of the outer surface 238 at the outlet end 231.

With the stent 229A extending through the trabecular meshwork 21, the tissue of the trabecular meshwork 221 provides additional anchoring force for retaining the stent 229A with its inlet end 230 in the anterior chamber and its outlet end 231 in Schlemm's canal. For example, the trabecular meshwork 21 would naturally tend to close an aperture occupied by the stent 229A. As such, the trabecular meshwork 221 would tend to squeeze the stent 229A. Because the exterior surface 238 is conical, the squeezing force applied by the trabecular meshwork 221 would tend to draw the stent 229A towards Schlemm's canal 22. In the illustrated embodiment, the stent 229A is sized such that a portion 234 of the stent 229 adjacent to the inlet end 230 remains in the anterior chamber 20 while a portion 235 of the stent 229 adjacent to the outlet end 231 remains in Schlemm's canal 22.

In the illustrated embodiment, the outer surface 238 of the stent 229A is straight. Alternatively, the outer surface 238 can have other contours such as, for example, but without limitation curved or stepped. In one embodiment, the outer surface 238 can be curved in a concave manner so as to produce a trumpet-like shape. Alternatively, the outer surface 238 can be convex.

The stent 229A preferably includes one or plurality of posts or legs 236 configured to maintain a space between the outlet opening 233 and a wall of Schlemm's canal 22. As such, the legs 236 prevent a wall of Schlemm's canal from completely closing off the outlet opening 233 of the stent 229A. In the illustrated embodiment, the legs 236 are coupled to the distal-most surface of the stent 229A and are substantially parallel to an implant axis extending through the stent 229A and between the anterior chamber 20 and Schlemm's canal 22.

This arrangement of the legs 236 and the outlet 233 imparts an axisymmetric flow characteristic to the stent 229A. For example, aqueous can flow from the outlet 233 in any direction. Thus, the stent 229A can be implanted into Schlemm's canal at any angular position relative to its implant axis. Thus, it is not necessary to determine the angular orientation of the stent 229A prior to implantation, nor is it necessary to preserve a particular orientation during an implantation procedure.

Figure 49B:
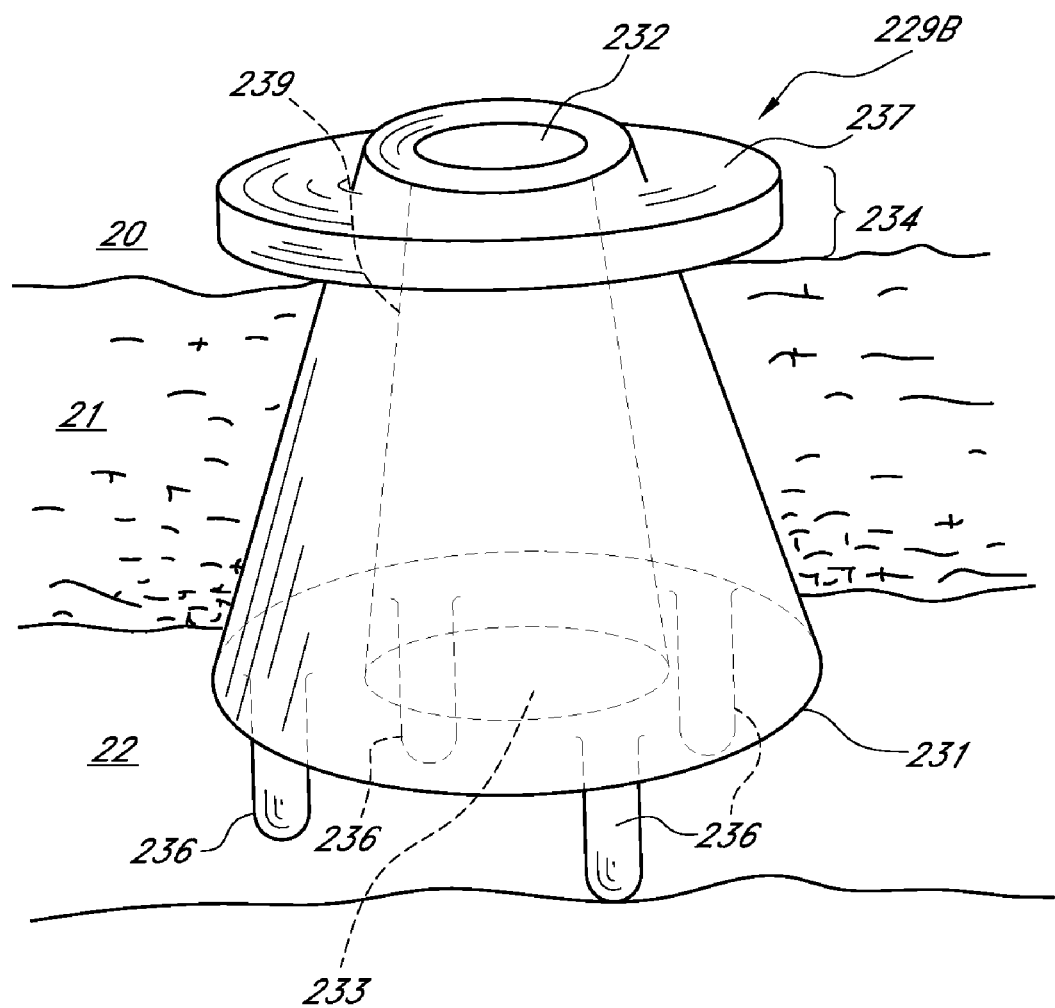
FIG. 49B is an oblique elevational view of a modification of the stent illustrated in FIG. 49A.

FIG. 49B illustrates a modification of the stent 229A, identified generally by the reference numeral 229B. In this embodiment, the stent 229B includes a flange 237 extending radially from the portion 234. Preferably, the flange 237 is configured to retain the first portion 234 within the anterior chamber 20. It is to be recognized that although generally, aqueous will flow from the anterior chamber 20 towards Schlemm's canal 22, the stent 229A, 229B or any of the above-described stents as well as other stents described below, can provide for omni-directional flow of aqueous.

Figure 49C:
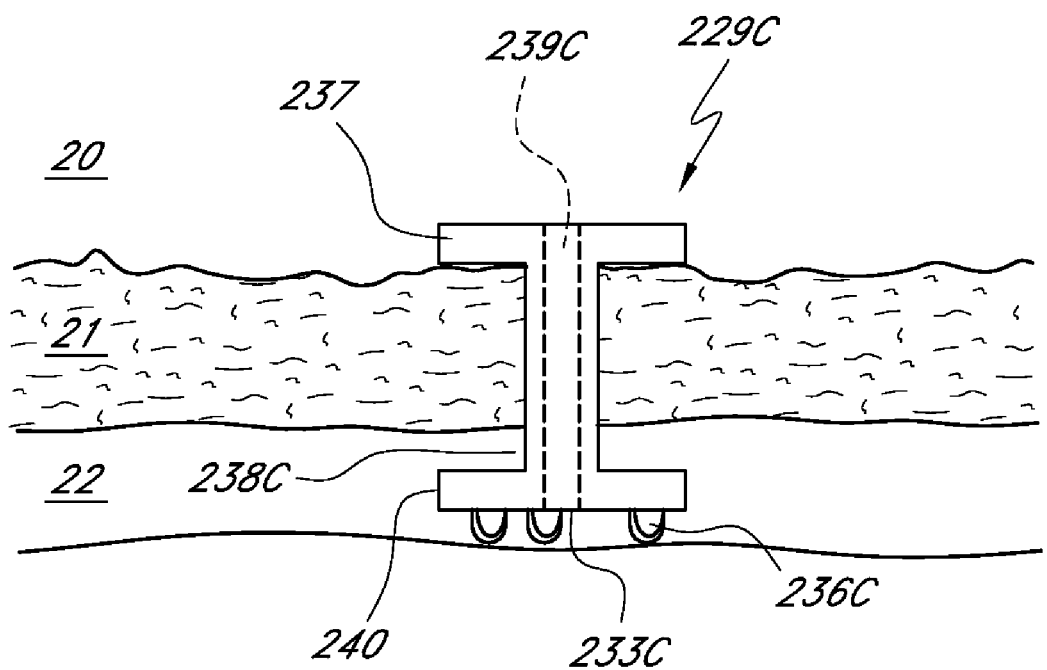
FIG. 49C is a side elevational view of another modification of the stent illustrated in FIG. 49A.

FIG. 49C illustrates another modification of the stent 229A, identified generally by the reference numeral 229C. In this embodiment, the outer surface 238C is not conical. Rather, the outer surface 238C is cylindrical. The stent 229C includes a flange 240 that can be the same size and shape as the flange 237. The legs 236C extend from the flange 240.

Constructed as such, the natural tendency of the tissue of the trabecular meshwork 21 to close the hole in which the stent 229C is disposed, aids in anchoring the stent 229C in place. Additionally, the legs 236C aid in preventing the walls of Schlemm's canal from completely closing the outlet 233C of the lumen 239C.

Device for Mechanically Distending Collector Duct

Figure 50A:
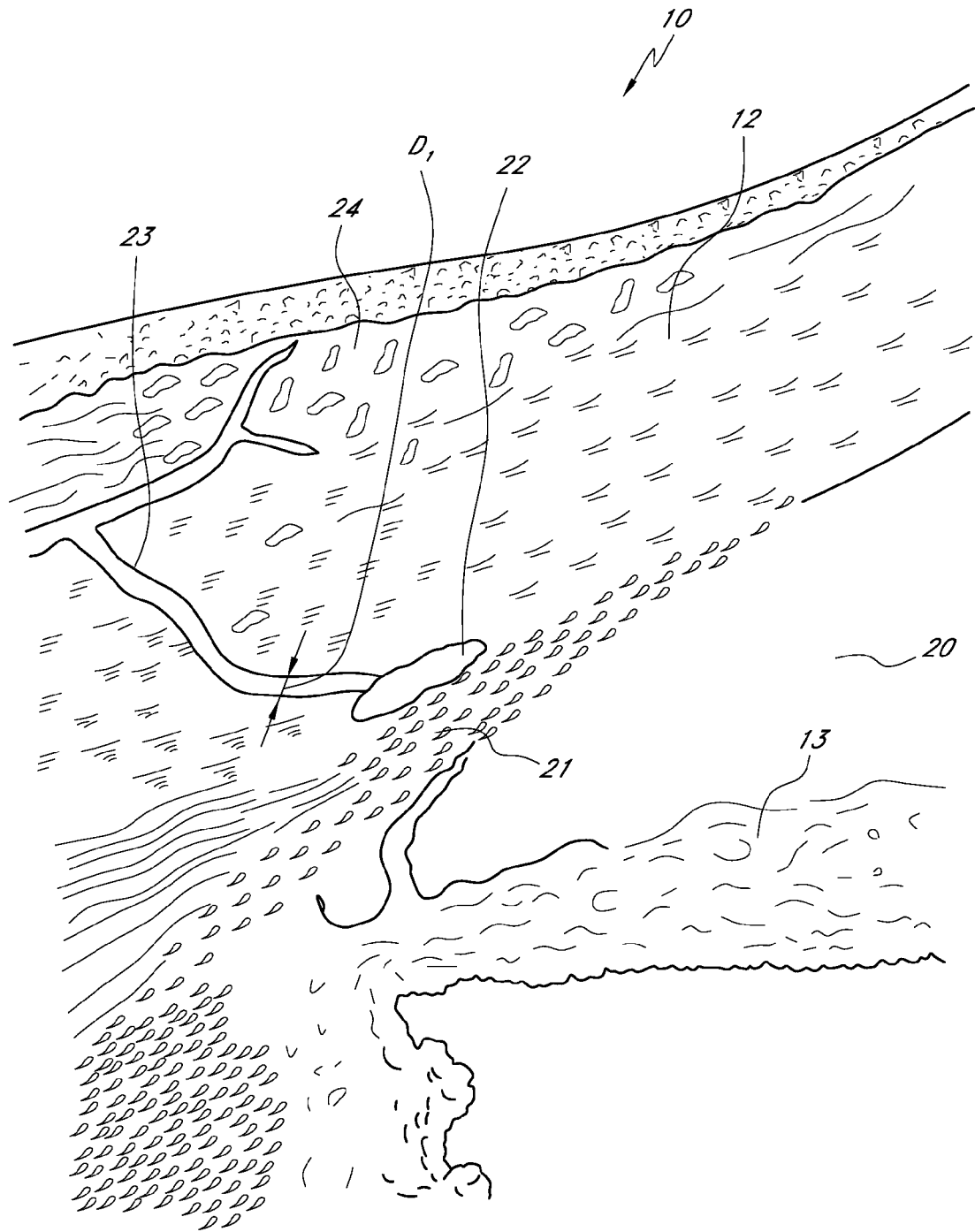
FIG. 50A is a cross-sectional view of the eye portion showing anatomically the trabecular meshwork, Schlemm's canal and one collector duct.
Figure 50B:
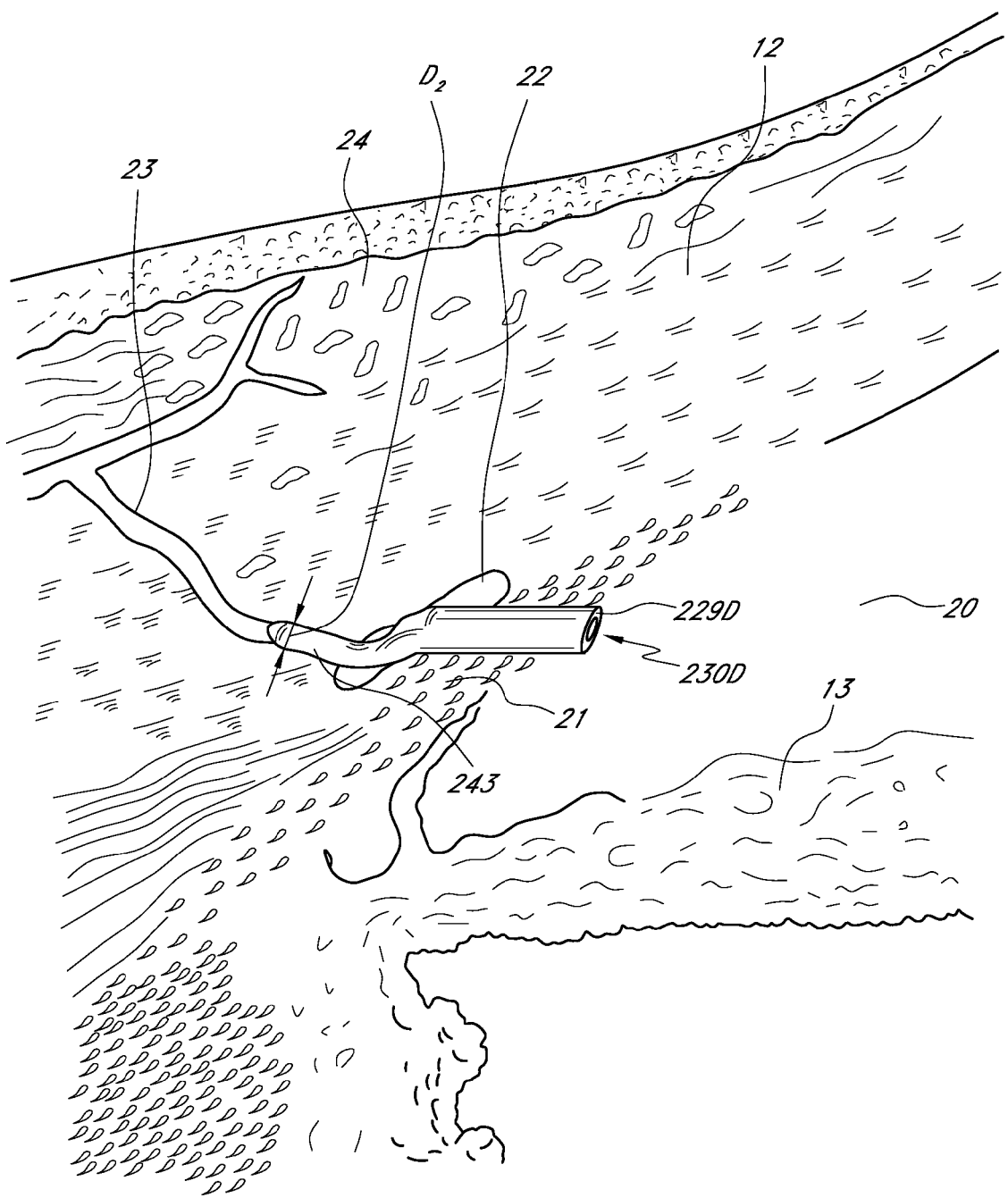
FIG. 50B is a cross-sectional view of FIG. 50A with a portion of a stent mechanically inserted into one of the collector ducts.

FIG. 50A is an enlarged cross-sectional view of a portion of the eye 10 showing, anatomically, the trabecular meshwork 21, Schlemm's canal 22, and a collector duct 23 in a natural state. FIG. 50B shows a stent 229C extending into and thereby distending the collector duct 23.

The collector duct 23 has an inner diameter identified generally by the reference numeral $D_1$, when in a relaxed or natural state. Because the collector duct 23 is not typically perfectly round, the diameter $D_1$ can correspond to an "equivalent" diameter. As used herein, the equivalent diameter can be determined by dividing the circumference of the inner surface of the collector duct 23 by $\pi$.

The stent 229D is sized to extend from the anterior chamber 20 and into the collector duct 23. Thus, in the illustrated embodiment, the stent 229D includes an upstream end portion 230D and a downstream end portion 243.

The upstream portion 230D is configured to open into the anterior chamber 20. The stent 229D is sized so as to extend from the anterior chamber 20 and into the collector duct 23. In the illustrated embodiment, the stent 229D is sized so as to extend from the anterior chamber 20, through the trabecular meshwork 21, through a portion of Schlemm's canal 22, and into the collector duct 23. However, it is conceived that the stent 229D could bypass Schlemm's canal 22 and extend directly into a portion of the collector duct 23 downstream from Schlemm's canal 22.

The downstream end portion 243 can have an outer diameter $D_2$ that is larger that the diameter $D_1$. Preferably, the end potion 243 is sized and configured for easy insertion into a collect duct 23 without injuring the tissue or tissue surface of the collector duct 23. Thus, when the end portion 243 is disposed in the collector duct 23, the collector duct 23 is distended, i.e., enlarged. As such, the resistance against the outflow of aqueous provided by the collector duct 23 in its natural state can be reduced, thereby reducing IOP.

Preferably, the end portion 243 has a diameter $D_2$ substantially larger than the equivalent diameter $D_1$ of the duct 23 so as to deform the collector duct beyond its elastic threshold into plastic deformation region. As such, the collector duct 23 can aid in anchoring the stent 229D in place.

Applicator for Multiple Stent Implantation

Figure 51A:
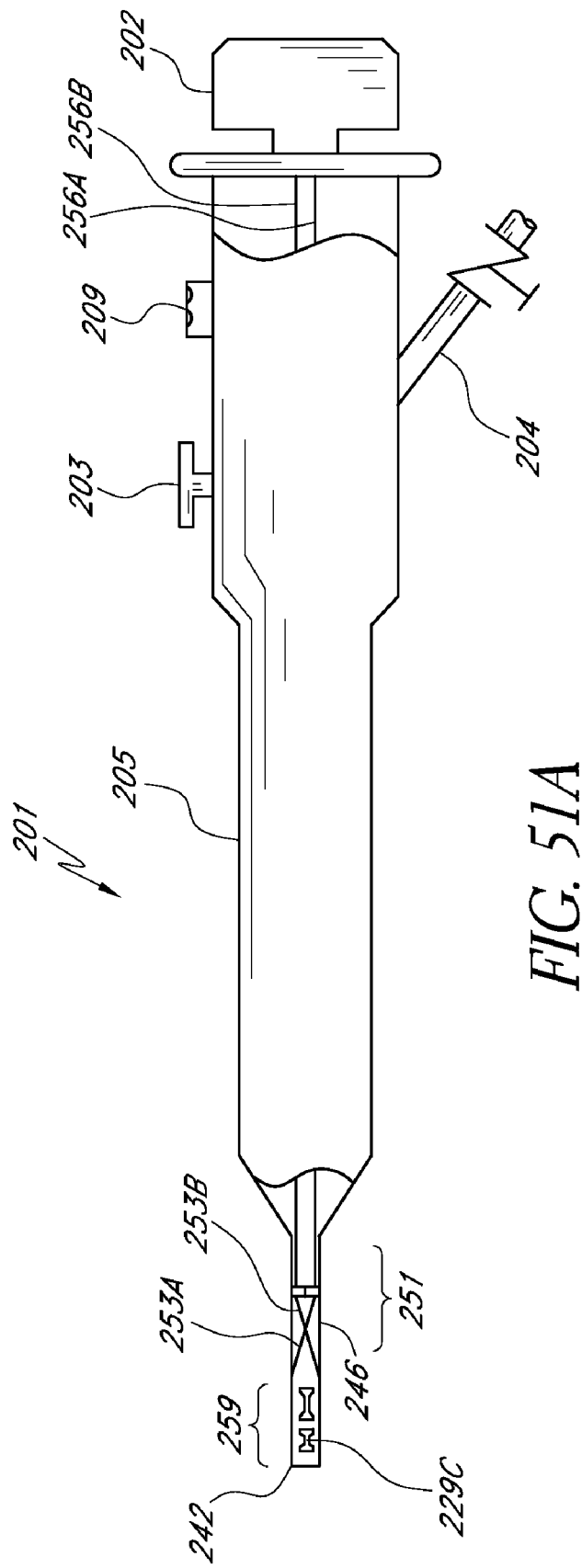
FIG. 51A is a side elevational view of a stent delivery applicator with a steerable distal section for multiple stent deployment.

FIG. 51A is a perspective view of a stent delivery applicator 201 configured for multiple stent deployment. The delivery applicator 201 comprises an injection sheath 246 defining a stent lumen 249, a distal stent-holding section 259, and a handle 205.

The handle 205 includes an outer surface preferably configured to be grasped by a human hand. Additionally, the handle can comprise a stent delivery button 203. By way of example, the stent delivery button 203 is configured to cause a stent discharge mechanism to discharge, from the applicator sheath 246, one stent at a time. The applicator 201 can be configured to store and discharge a plurality of any combination of the stents 229, 30, 30a, 30b, 30c, 30d, 30e, 30f, 30g, 30h, 30i, 30j, 30k, 30m, 30n, 30p, 30q, 30r, 30s, 30t, 30u, 30v, 229A, 229B, 229C, and 229D described above, the additional stents described below, or any other ocular stent or implant. In the illustrated embodiment, the applicator 201 is loaded with a plurality of the stents 229C The applicator 201 can include other features as well, for example, but without limitation, an optional connector 209 for connecting to an external ultrasound power source, a fluid infusing port 204 for fluid infusion or viscocanalostomy, and a steering mechanism control device 202 configured to control the steering of a steerable section 251 of the applicator 201.

The steerable section 251 can be configured to deflect the distal stent-holding section 259 about at least one axis. Optionally, the steerable section 251 can configured to deflect the distal stent-holding section 259 about at least two axes, one axis being substantially perpendicular to the other. Thus, the portion of the sheath 246 that defines part of the steerable section 251 is flexible. Generally, similar steering mechanisms for deflecting a portion of an medical device, such as endoscopes, are well-known in the art.

Figure 51B:
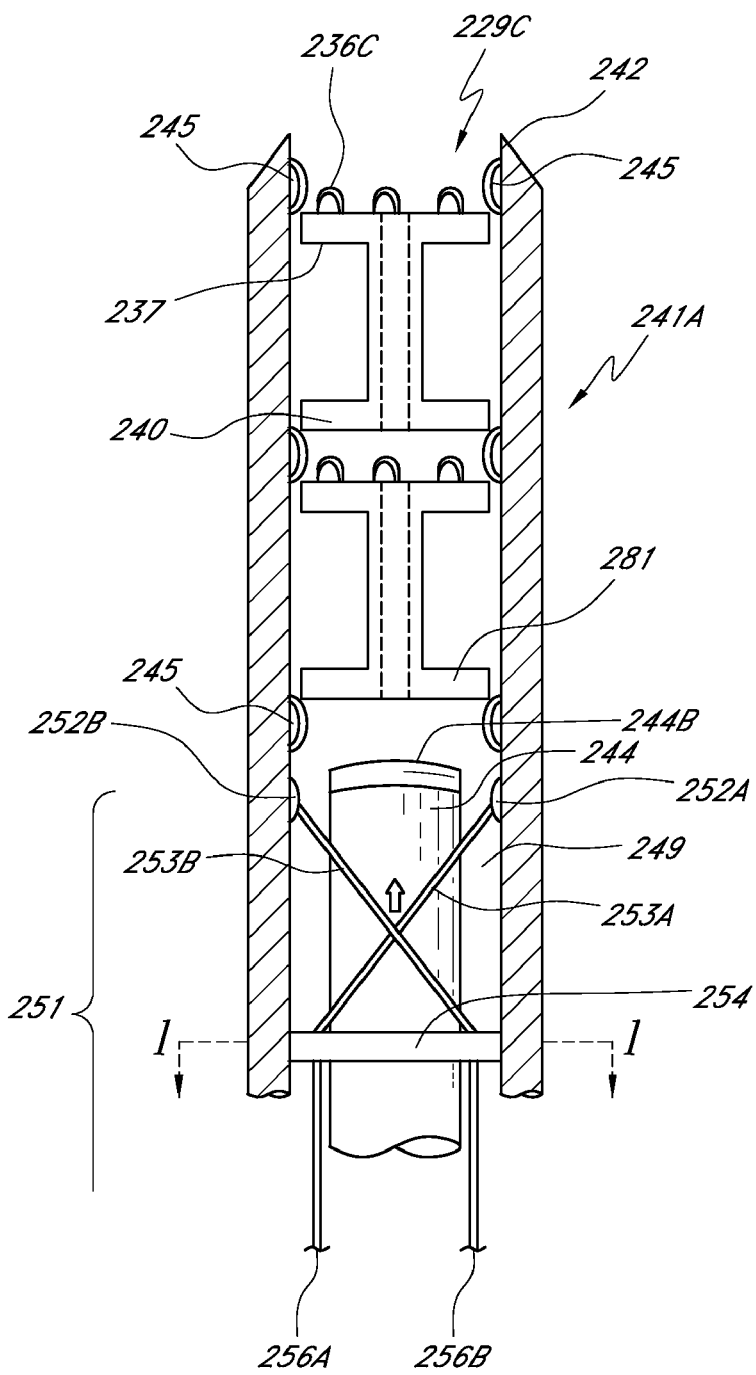
FIG. 51B is a schematic and partial sectional view of the distal section of the stent delivery applicator of FIG. 51A.

With reference to FIG. 51B, in the illustrated embodiment, the steering actuator 202 is connected to a plurality of pulling wires 256A, 256B. The wires 256A, 256B have distal portions 253A, 253B, respectively, disposed distally from the handle 205. The end 252A of the distal wire portion 253A of the first pulling wire 256A is attached to one side of an inner surface of the sheath 246. The second pulling wire 256B has its end 252B of the distal wire portion 253B attached to the opposite side of the inner surface of the sheath 246. The wire ends 252A and 252B are disposed within the steerable distal section 251.

Figure 51C:
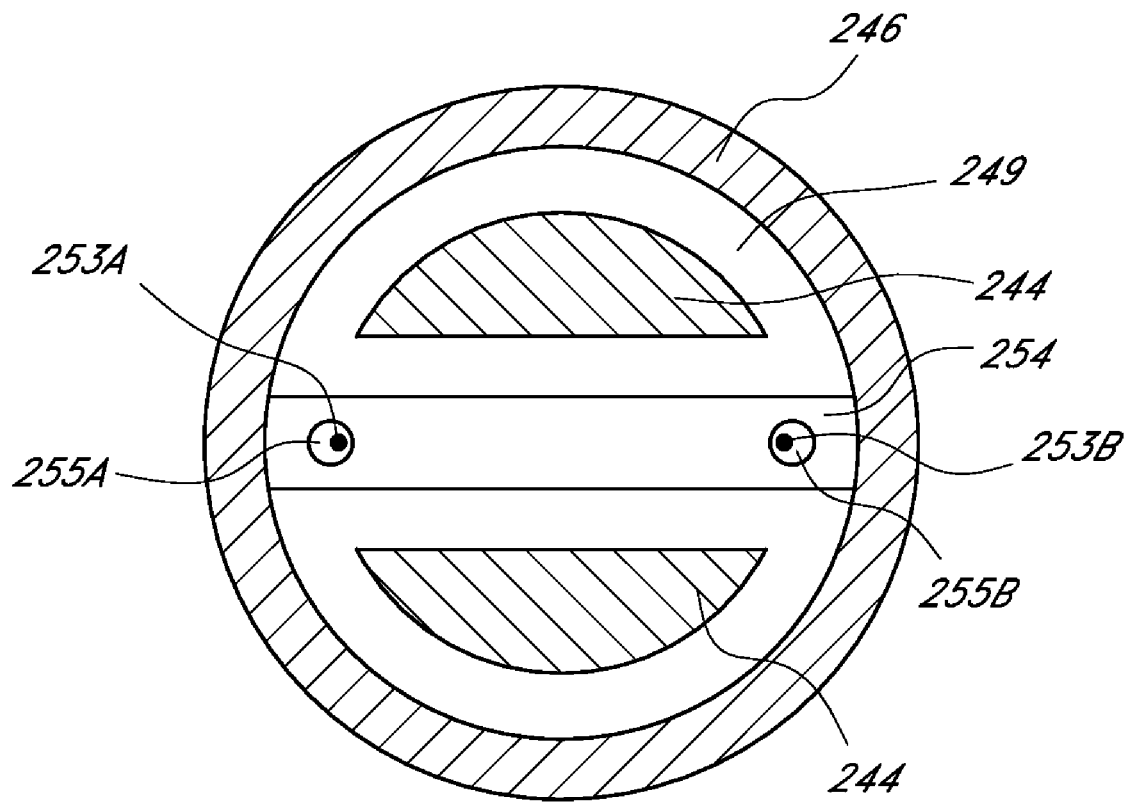
FIG. 51C is a cross-sectional view, section 1-1 of FIG. 51B.

With reference to FIG. 51C, a relatively rigid guide 254 is disposed in the lumen at an appropriate location proximal to the wire ends 252A, 252B. The guide is configured to guide the pull wires 256A, 256B such that the sheath 246 is deflected when the pull wires 256A, 256B are pulled. In the illustrated embodiment, the guide 254 is in the form of a plate member.

The guide 254 can include holes 255A, 255B through which the pulling wires 253A, 253B extend. The guide 254 and the points at which the wire ends 252A, 25B are spaced. As such, when the pull wires 253A, 253B are pulled by actuation of the steering actuator 202, the distal end of the sheath 246 is deflected. For example, as shown in FIG. 51D, when the wire 256A is pulled, the sheath deflects from Position I to Position II.

As noted above, the delivery apparatus 201 can be configured to discharge a plurality of stents, one at a time, for implantation. In the illustrated embodiment, as shown in FIG. 51B, the delivery apparatus 201 includes a plunger 244 connected with the stent delivery button 203. The plunger 244 can comprise one or a plurality of plunger bodies that are joined at the distal plunger end 244B. The distal plunger end 244B has a generally round configuration and smooth surface adapted for evenly pushing a stent, such as the stent 229C, out of the sheath during a deployment phase of an implantation procedure.

As noted above, the sheath 246 defines a lumen 249 having a plunger 244. A space between the plunger 244 and the distal end 242 is reserved for storing a plurality of stents. The sheath 246 includes at least one holding member 245 for each stent 229C stored therein. The holding members 245 are configured to retain the stents 229C in place during storage and use, and to allow the stents 229C to pass when the stent 229C is pushed by the plunger 244.

In the illustrated embodiment, the sheath 146 includes a row of a plurality of holding members 245 upstream and downstream from each stent 229C stored in the sheath 246. Thus, each stent 229C is prevented from unintentionally moving in the upstream and downstream directions.

FIG. 51B illustrates two stents 229C being stored in the sheath 246. However, it is conceived that the sheath 246 and holding members 245 can be configured to hold one, three, or more stents 229C within the stent-holding distal end 259.

The holding member 245 can be a wire configured to exerted a force to hold the stents 229C in place during storage and use, until the plunger 244 is moved to discharge a stent 229C from the end 242. For example, the wire can be made from a spring metal, an elastically deformable plastic, or other material, sized and shaped to retain the stents 229C during storage, and to allow the stents 229C to pass under a force that can be generated by or applied to the plunger 244, toward the end 242. In the illustrated embodiment, the wires forming the holding members 245 extend generally parallel to and convexly into the lumen 249, and thus define stops for preventing unintentional movement of the stents 229C.

Alternatively, the holding members 245 can be in the form of a mechanically or electronically actuatable gate. Such a gate can be configured to move from a closed position in which the stents 229C are retained in the storage positions, and an open position in which the stents 229C can be moved in the downstream direction. A mechanical gate can be formed from members that can be moved or deflected radially from the inner surface of the lumen 249, under the control of a pull wire (not shown). An electronic gate can also include radially moveable or deflectable members controlled by an electronic actuator, such as, for example, but without limitation, solenoids, stepper motors, servo motors, and piezoelectric modules.

Alternatively, piezoelectric modules can be used to form the holding members. For example, small piezoelectric modules can be mounted on the inner surface of the sheath 246 to form stops when in a locked position. The piezoelectric modules can be connected to a power supply with conduits. Thus, when actuated, the piezoelectric modules can contract so as to move to an open position in which the stents 229C can pass.

As noted above, the applicator 201 preferably is configured to eject one stent at a time from the end 242. Thus, the applicator 201 can be configured to move the plunger 244 a predetermined distance each time the button 203 is depressed. For example, the button can be mechanically connected to the plunger 244 so as to move the plunger 244 downstream through the sheath 246 over the predetermined distance. The predetermined distance can be, for example, equal to about the length of the stent 229C.

Alternatively, the plunger can be driven by an electronic actuator (not shown) configured to eject one stent 229C at a time from the sheath 246. For example, the electronic actuator can be configured to drive the plunger 244 over the predetermined distance each time the button 203 is depressed. The electronic actuator can be, for example but without limitation, solenoids, stepper motors, servo motors, and piezoelectric modules. Driver electronics (not shown) can be configured to drive the actuator so as to urge the plunger 244 over the predetermined distance.

Preferably, the end 242 of the sheath 246 is sharpened to define a cutting (microtrephining) tip for creating a hole within the trabecular meshwork 21 for stent placement. Thus, the applicator 201 can be used for cutting the trabecular meshwork 21 and for implanting stents.

A further advantage is provided where the applicator includes an illumination feature for illuminating at least a portion of the implantation site. For example, the illumination feature can be configured to generally illuminate the site at which a stent is to be implanted. Optionally, the illumination feature can be configured to generate a reticule for aligning the applicator with the desired implantation site. In one embodiment, a light source is provided to the tip section 242 of the stent applicator 201 wherein either laser light is provided for cutting/spotting or fiber optic light is provided for illumination.

For example, but without limitation, the illumination feature can comprise a small diameter light pipe or optic fiber element configured to emit a fine point or beam of light and configured to be introduced ab-internally. Additionally, the face or lens of the pipe or element can be configured to be placed against the trabecular meshwork. In one embodiment, the light pipe or optic fiber is the construct material of the sheath 246 of the stent delivery applicator 241A for multiple stent deployment as shown in FIG. 51B. In another embodiment, the light pipe or optic fiber is snugly inserted within the lumen 249 of the applicator sheath 246 or over the outer periphery of the applicator sheath 246. Optionally, the illumination device can be configured such that the point or beam emitting from the light tube would be highly visible from the outside of the eye and serve to guide the implantation of a stent.

As an alternative to including an illumination feature with the applicator 201, simple non-invasive trans-scleral illumination, if of the proper intensity and wavelength, perhaps in a darkened environment, could silhouette the Schlemm's canal, trabecular meshwork, or more probably, the scleral spur with sufficient resolution to enable ab-externo placement of a device into Schlemm's canal. In this case, blood could be backed up in a retrograde manner into Schlemm's canal by the surgeon to provide additional optical density. Imaging means for ab internally imaging the anatomic structures for TBS stent implantation using ultrasound imaging, laser imaging, OCT imaging or multi-wavelength scanning can also be provided.

A further advantage is provided where the applicator 201 also includes an imaging feature. For example, where the applicator 201 includes an imaging feature for transmitting a video representation of an implantation site of a stent to a user of the applicator, an implantation procedure can be further simplified. The imaging feature can utilize any type of known imaging techniques, including, for example, but without limitation, optical, and ultrasonic. In one embodiment, an endoscope is mounted at the tip section 242 of the stent applicator 201 for visualization during stent deployment and/or implantation.

FIG. 51D shows one embodiment of the applicator 201 of FIG. 51A having an ultrasonic imaging system. The illustrated embodiment of the imaging system is included on an applicator with a steerable section. However, it is to be noted that the imaging system can be used on an applicator that does not have a steerable section.

In one embodiment, the ultrasonic imaging system comprises two ultrasonic probes or transducers 206, 207. The transducers 206, 207 can be formed from an ultrasound ring or ultrasound tape. Preferably, the transducers 206, 207 are located adjacent to the distal end 242 of the delivery apparatus 201. As such, the transducers 206, 207 can move with the distal end 242 during an implantation procedure.

The ultrasonic transducers 206, 207 are connected by flexible wires (not shown) through the interior void 243 of the apparatus or through within the sheath 246 to the connector 209 located at the handle 205 so that the ultrasonic signals are directed outwardly and received inwardly relative to the transducers 206, 207. For example, one of the transducers 206, 207 can be configured to emit ultrasonic energy, and the other can be configured to absorb the reflected portion of the emitted ultrasonic energy and to produce a signal indicative of the absorbed energy.

In order to enhance the viewing and positioning of the distal end 242 of the apparatus, an ultrasonic marker 208, which is visible to ultrasonic energy, can be mounted at about the distal end 242 of the applicator 201. For example, but without limitation, such a marker 208 can be in the form of one or a plurality of encapsulated air bubbles. In one illustrative example, the bubble in a marker 208 can be formed by introducing air by a syringe (not shown) penetrating the wall of the sheath 246 and thereafter sealing the hole created by the syringe with epoxy.

Optionally, a plurality of markers 208 can be disposed in the front distal section 259. The markers 208 can be sized and configured to aid in locating and identifying the orientation of the distal end section 259. For example, the markers 208 can be located and/or viewed with external ultrasonic imaging systems (not shown), such as those commonly used in similar medical procedures.

A further advantage is provided where the stent delivery applicator 201 is both steerable and configured for multiple stent implantation. As such, the applicator 201 can be inserted into the anterior chamber 20, through an incision, such as a corneal incision, and multiple stents can then be implanted at different locations without removing the applicator 201 or creating other incisions, described in greater detail below.

Figure 52A:
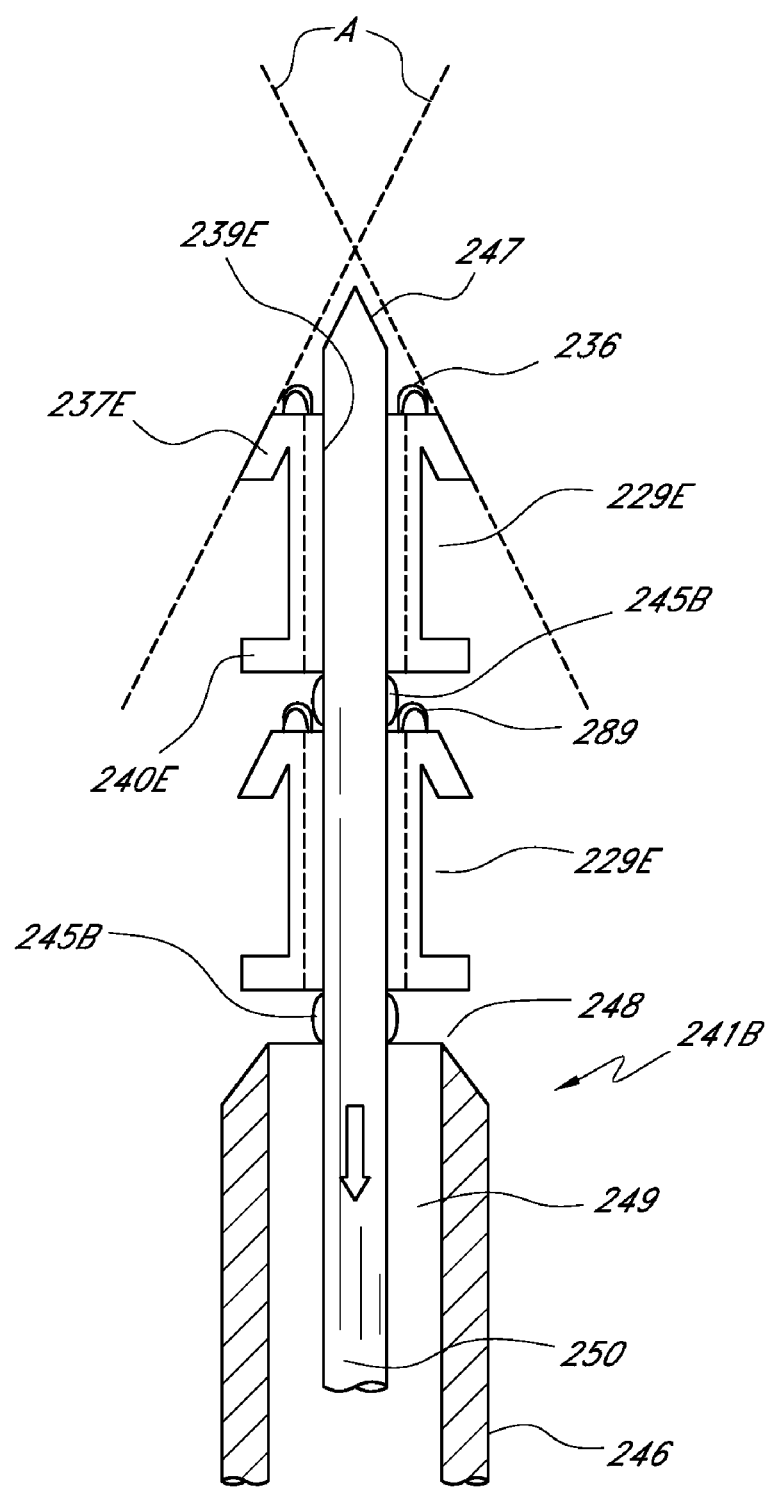
FIG. 52A is a partial sectional and side elevational view of a distal section of a modification of the stent delivery applicator illustrated in FIG. 51A.

FIG. 52A shows another embodiment of the stent delivery distal portion 241, identified generally by the reference numeral 241B, and another embodiment of a stent, identified generally by the reference numeral 229E.

The stent 229E comprises a first (proximal) flange 240E and a second (distal) flange 237E with a plurality of supporting legs or posts 236. The second flange 237E of the stent 229E is configured to be foldable. For example, the first flange 237E can be configured to be elastically foldable toward an upstream direction. As such, the first flange 237E can be folded toward an upstream direction, as illustrated in FIG. 52A when stored in the sheath 246. Thus, after the first flange 237E has been pushed through the end 242, the first flange 237E can resiliently unfold. As such, the first flange 237E can provide enhanced anchoring for the stent 229E when implanted into the trabecular meshwork 21.

A further advantage can be provided where the applicator 201 includes a cutting device that can extend through the lumens 239E of the stents 229E. For example, as shown in FIG. 52A, a cutting device 250 can include a cutting tip 247 and can be configured to extend through the stents 229E during an implantation procedure. As such, the cutting device can being an incision at the center of the site at which the stent 229E is to be inserted through the trabecular meshwork 21. In the illustrated embodiment, the cutting device is in the form of a trocar.

With continued reference to FIG. 52A, the cutting device 250 is configured to be moveable axially through the lumen 249 of the applicator end portion 241B of the sheath 146. Additionally, the cutting device 250 can be moved axially relative to the stent or stents through which it extends.

Another advantage can be provided where the cutting device 250 also includes at least one holding member for holding a stent. For example, the cutting device 250 includes at least one holding device 245, described above with reference to FIG. 51B, can be configured to hold a stent at least during an implantation procedure, and to release the stent at the appropriate time.

Preferably, the holding members 245B are arranged to align the sides of the cutting tip 247 with the distally facing sides of the flange 237E when the flange 237E is folded. For example, as shown in FIG. 52A, when the flange 237E is folded, the distally facing side of the flange 237E is aligned with the sides of the cutting tip 247, as indicated by the dashed-lines identified by the letter "A." This alignment can be facilitated by arranging the holding members 245B such that the cutting device 250 extends distally from the flange 237E sufficiently to cause the sides of the cutting tip 247 to become aligned with the flange 237E. As such, the sides of the cutting tip 247 and the distally facing side of the flange 237E generate a more smooth surface for penetrating the trabecular meshwork 21 during an implantation procedure.

Figure 52B:
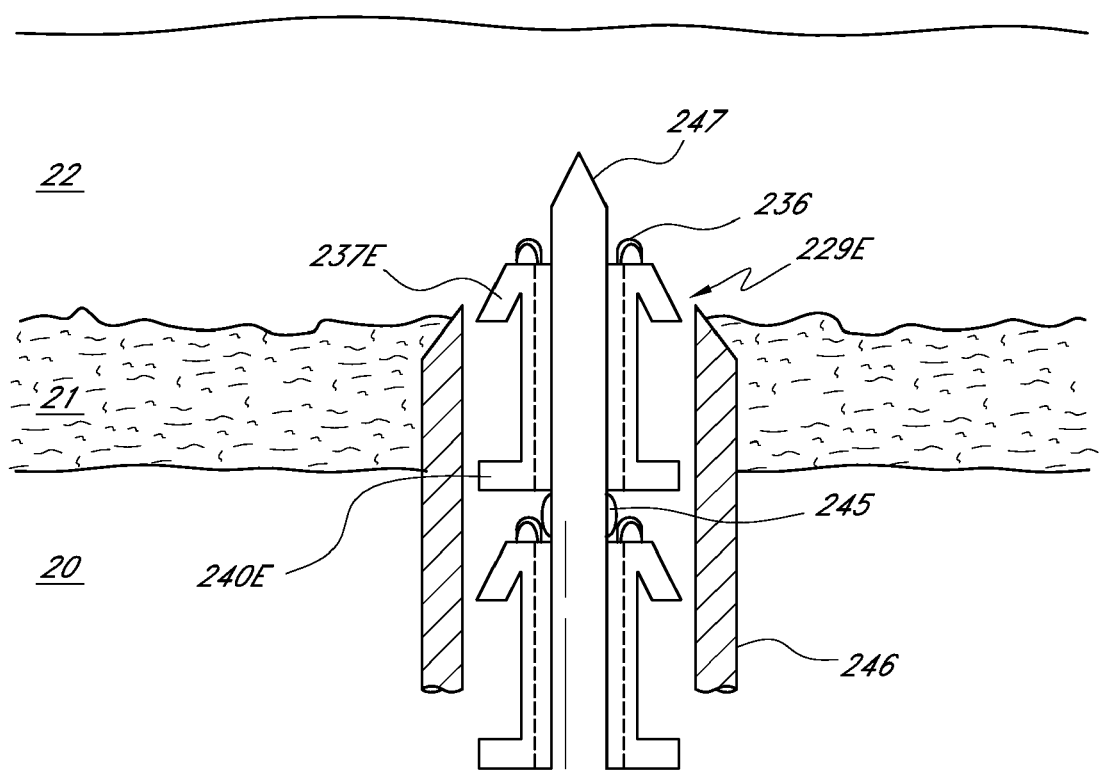
FIG. 52B is a partial sectional and side elevational view of a distal section of the stent delivery applicator illustrated in FIG. 51A having been inserted through a trabecular meshwork with the stent disposed within the distal section.

During operation, the applicator end portion 241B can be pushed into trabecular meshwork 21, with the flange 237E disposed in Schlemm's canal 22, as shown in FIG. 52B. The sheath 246 can then be retracted out of Schlemm's canal 22, leaving the cutting device 250 and stent 229E in place (FIG. 52C).

Figure 52C:
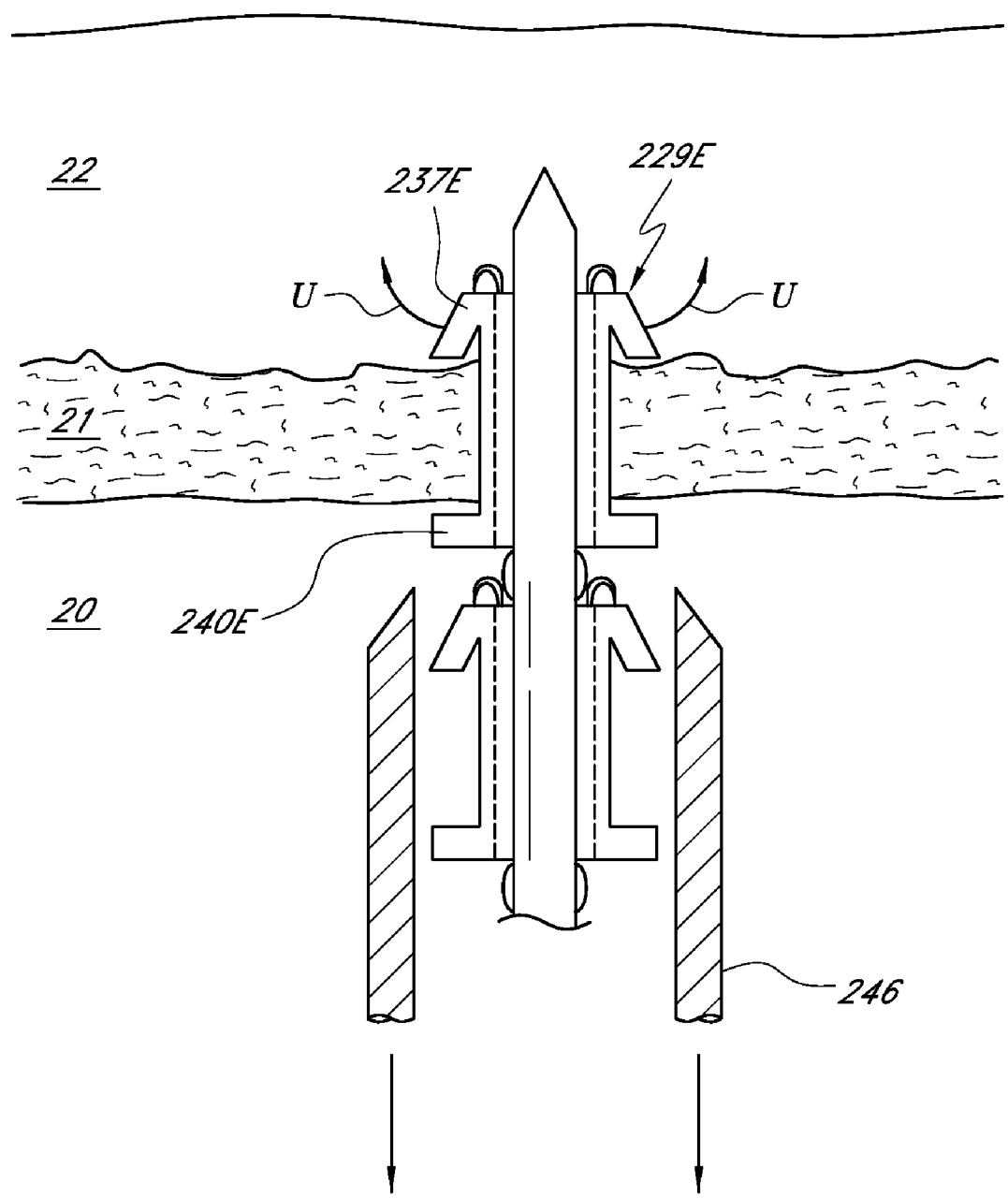
FIG. 52C is a partial sectional and side elevational view of a distal section of the stent delivery applicator illustrated in FIG. 51A having been inserted through a trabecular meshwork and after the sheath of the distal portion has been withdrawn.
Figure 52D:
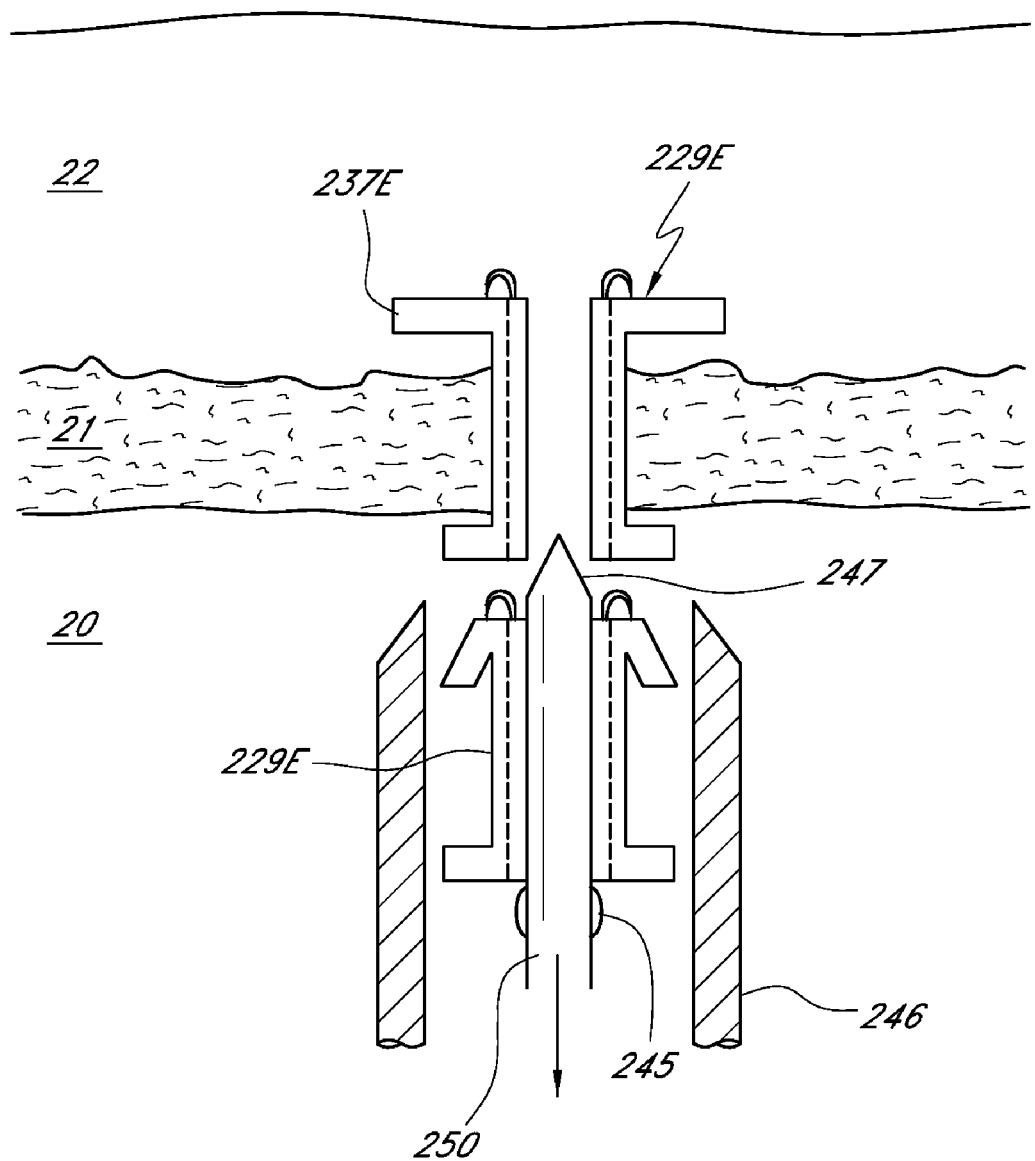
FIG. 52D is a partial sectional and side elevational view of a distal section of the stent delivery applicator illustrated in FIG. 51A having been inserted through a trabecular meshwork, and after the sheath and a cutting member have been withdrawn.

With the sheath 246 retracted, the first flange 237E can unfold, as indicated by the arrows U in FIG. 52C, thereby providing enhanced anchoring of the stent 229E within Schlemm's canal 22 (FIG. 52D). Additionally, the second flange 240E is within the anterior chamber 20.

As shown in FIG. 52D, the cutting device 250 can then be retracted relative to the applicator end portion 241B and the stent 229E, leaving the stent 229E in place. Optionally, the cutting device 250 and the sheath 246 can be retracted together.

As noted above, the holding members 245 are configured to limit the movement of the stents 229E relative to the cutting device 250. When the cutting device is retracted, the next stent 229E preferably is moved passed (in the downstream direction) the holding member 245 that was previously between the stents 229E. As such, the next stent 229E can be moved into position for implantation. Thus, the holding members 245 preferably are configured to allow the stent 229E to move toward the cutting tip 247 when the cutting device 250 is retracted. For example, the holding members 245 can be controlled so as to retract when the cutting device 250 is retracted.

Figure 53:
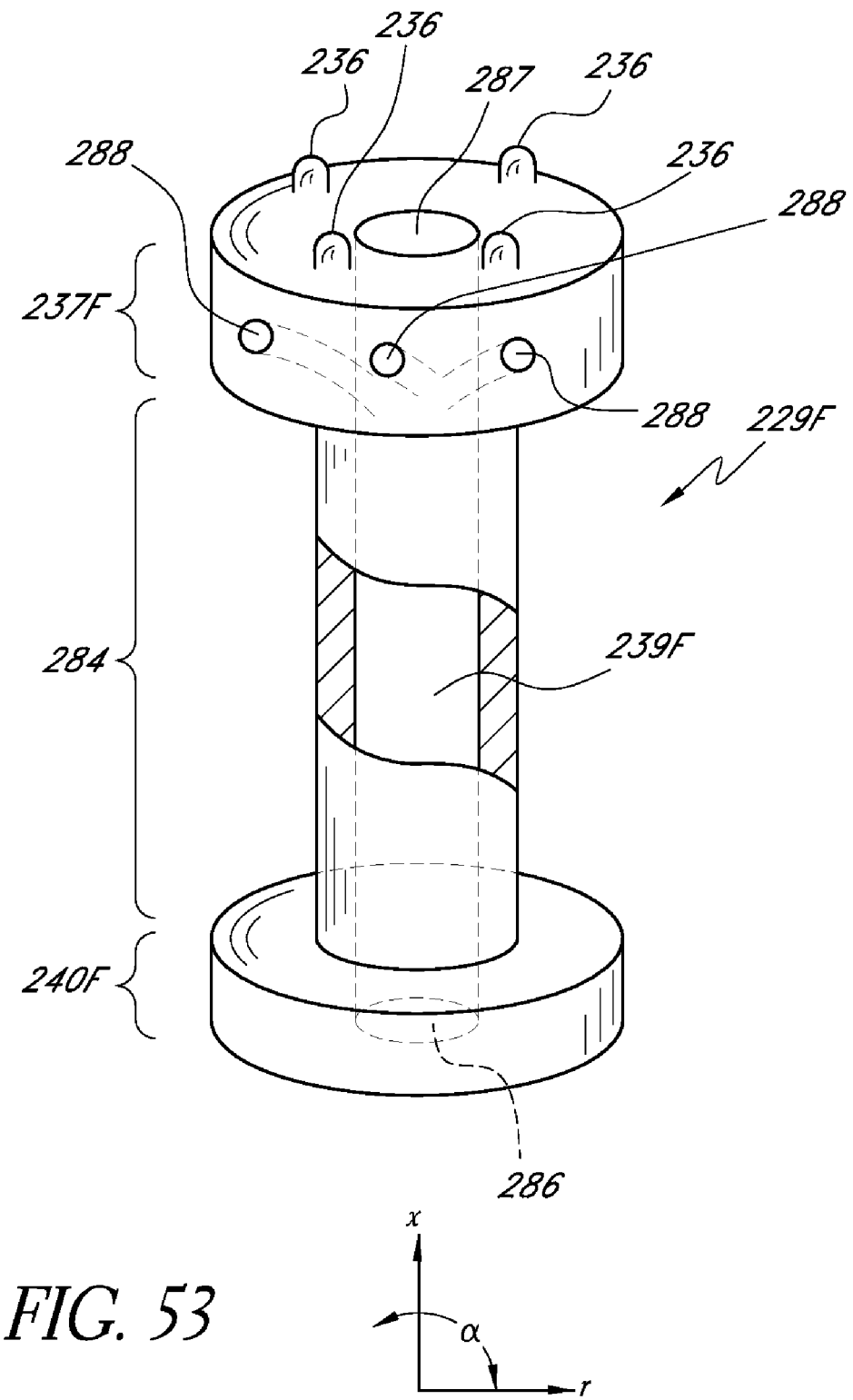
FIG. 53 is an oblique side elevational and partial sectional view of a further modification of the stent illustrated in FIG. 32.

With reference to FIG. 53, another embodiment of an axisymmetric trabecular stenting device is illustrated therein and identified generally by the reference numeral 229F. For ease of description, but without limitation, the stent 229F is described below with reference to cylindrical coordinates of x, r and angle α as shown in FIG. 53.

The stent 229F comprises an inlet (proximal) section having a first flange 240F, an outlet (distal) section having a second flange 237F and a middle section 284 connecting the inlet section and the outlet section. A lumen 239F of the device 229F is configured to transport aqueous, liquid, or therapeutic agents between the inlet section and the outlet section. As referred to herein, "therapeutic agent" is intended to include pharmaceutical agents, drugs, genes, cells, proteins, and/or growth factors.

The inlet section of the stent 229F has at least one inlet opening 286 and the outlet section comprises at least one outlet opening 287. A further advantage is provided where the outlet section 237F includes at least one opening 287, 288 suitably located for discharging substantially axisymmetrically the aqueous, liquid or therapeutic agents, wherein the opening 287, 288 is in fluid communication with the lumen 285 of the device 281. In the illustrated embodiment, the openings 288 extend radially from the lumen 285 and open at the outwardly facing surface around the periphery of the outlet flange 237F.

In one embodiment of an implantation procedure, Pilocarpine is administered preoperatively to constrict the pupil to provide maximal protection of the lens in phakic individuals and to further open the anterior chamber angle to provide a better view of the surgical site. Topical and retrobulbar anesthetic are recommended. A small self-sealing temporal corneal incision can be made and Healon® viscoelastic (VE) can be injected to maintain the anterior chamber.

A microscope can be tilted slightly toward the surgeon and the patient's head can be rotated away from the surgeon to provide a suitable view of the nasal trabecular meshwork using a direct-view gonioscope that is placed on the eye. The applicator 201 with a preloaded stent, such as, for example, but without limitation, an one or any combination of the stents a plurality of any combination of the stents 229, 30, 30a, 30b, 30c, 30d, 30e, 30f, 30g, 30h, 30i, 30j, 30k, 30m, 30n, 30p, 30q, 30r, 30s, 30t, 30u, 30v, 229A, 229B, 229C, 229D, 229E, 229F, or any of the other stents described below, is advanced through the corneal wound and across the anterior chamber. The stent is pushed against the trabecular meshwork and moved inferiorly to pierce the trabecular meshwork and guide the stent into Schlemm's canal. After successful implantation and release of the stent, the applicator is withdrawn and the VE is flushed from the eye.

The G2 stent (for example, stent 229F of FIG. 53) can be smaller and of a significantly different design than the G1 stents, thus allowing it to be passed through a smaller corneal incision and be implanted with a simple axial motion. Reduced size and simplified surgical motions may enable implantation of the G2 stent without the use of viscoelastic and therefore eliminate a significant expendable material cost and the time necessary to administer and remove it.

Additionally, viscoelastic use in patients undergoing eye surgery can cause post-operative transient IOP spikes that can further damage the remaining glaucoma-compromised retina. Reduced surgical manipulations reduce the burden on the surgeon and reduce the stimulation and irritation of intraocular tissues. Furthermore, reduction in the corneal incision size raises the possibility that the incision could be made by the G2 applicator, and could potentially reduce the surgical implant procedure to an injectable implant procedure. Injectable stent therapy represents a potentially superior alternative to both end-stage surgical therapy and to patients burdened by the cumulative side effects, complications, and compliance issues associated with drug therapy.

Figure 54A:
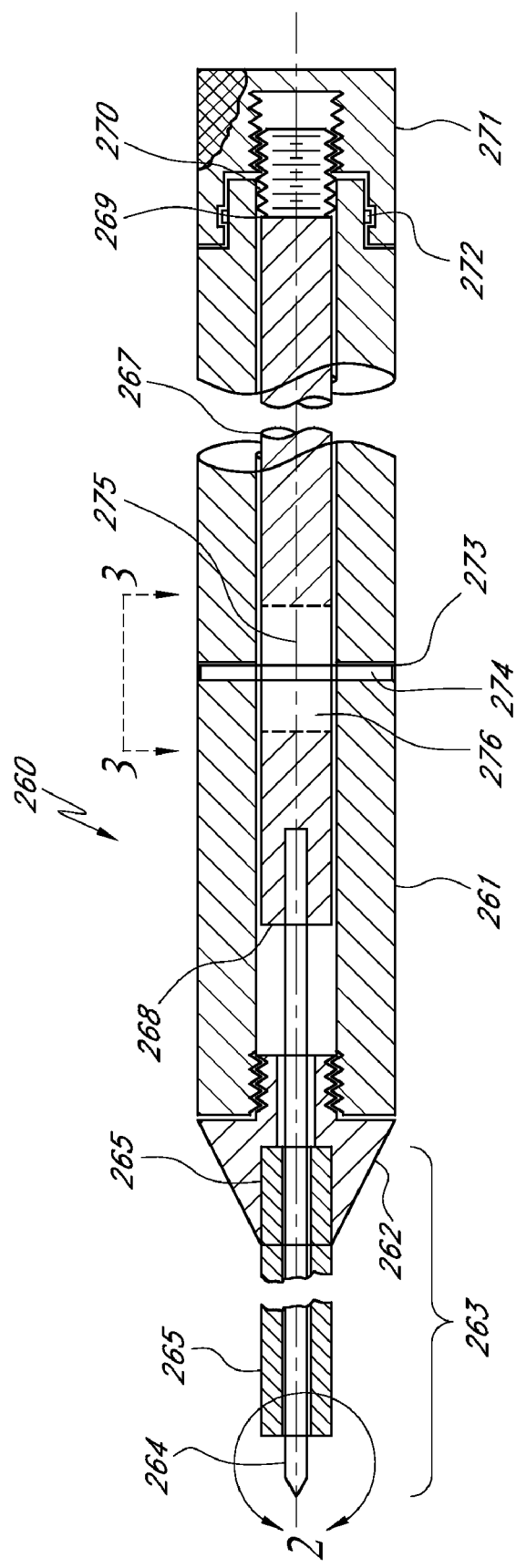
FIG. 54A is a sectional view of yet another modification of the stent delivery applicator illustrated in FIG. 51A.
Figure 54B:
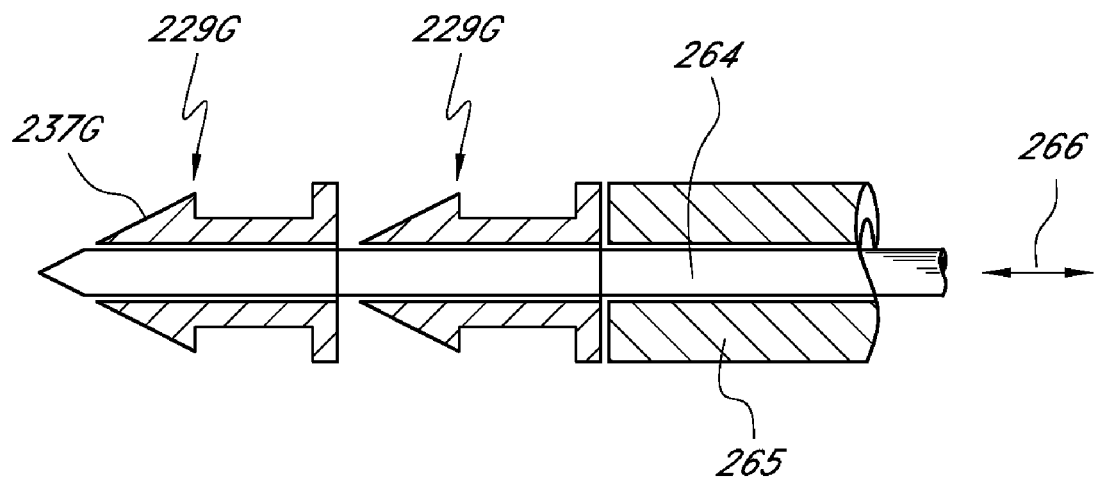
FIG. 54B is an enlarged sectional view of a distal end of the applicator illustrated in FIG. 54A and including two implants disposed over a trocar of the device, this portion being identified by the circle 2-2 in FIG. 54A.
Figure 54C:
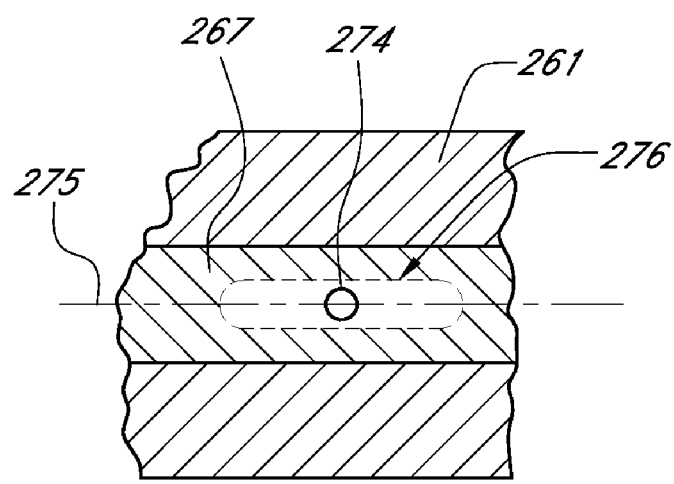
FIG. 54C is a sectional view of the applicator device taken along section line 3-3 of FIG. 54A.

The G2 stent and applicator system are sized, dimensioned and configured for placement through trabecular meshwork in an ab interno or ab externo procedures. FIGS. 54A-C illustrate additional examples of preferred G2 stent and applicator embodiments.

FIG. 54A shows yet another embodiment of a stent injector assembly for multiple stent deployment, identified generally by the reference numeral 260. The stent injector 260 comprises a housing 261 with a distal cap 262 and a distal stent-holding element 263 that is distal from the distal cap 261. Optionally, at least a portion of the distal stent-holding element 263 can be configured to be steerable with a steering mechanism that can be constructed in accordance with the description of the steerable section 251 described above with reference to FIGS. 51A-D.

The stent-holding element 263 can comprise an elongate member 264 with at least one stent slideably disposed thereon. The elongate member 264 can be configured to extend through the lumen of any of the stents 229A, 229B, 229C, 229D, 229E, 229F, or any of the other stents described below.

In the illustrated embodiment, the elongate member 264 extends through the lumen of stents 229G (FIG. 54B). In one embodiment, the distal stent 229G can be the same as the second or proximal stent 229G. In another embodiment, the distal stent and the proximal stent are different in size or configuration for placement at different locations. For example, the proximal and distal stents of FIG. 54B can be any combination of the stents 229A, 229B, 229C, 229D, 229E, 229F, and 229G. Additionally, the applicator 260 can be configured to be loaded with only one, three, or more stents.

In the illustrated embodiment, the distal flange 237G of the stent 229G can be wedge-shaped. For example, the distal end of the flange 237G can have a smaller diameter than that of the proximal end of the flange 237G. As such, the stent 229G can pass more easily through the trabecular meshwork 21. Additionally, the distally facing surface of the flange 237G can be inclined so as to be aligned with a distal surface of the elongate member 264. As noted above with respect to the cutting member 250, the elongate member 264 can be in the form of a trocar.

The stent-holding element further comprises a sleeve 265 configured to support the elongate member 264. The sleeve 265 (for example, made of hypo tubing) can be pressed or bonded onto the distal cap 262 to form a sleeve-cap subassembly. The elongate member 264 can be configured to be axially moveable relative to the sleeve 265, as indicated by the arrow 266 (FIG. 54C).

The housing 261 can also comprise a tip actuator 267 that has a distal end 268 and a proximal end 269. The elongate member 264 can be press fit or bonded into the distal end portion of the tip actuator 267 to form a tip/tip actuator subassembly. In one exemplary but non-limiting embodiment, the elongate member 264 can be a 0.08 mm diameter sharpened rod made from a hard material, such as a metal.

The tip/tip actuator subassembly is fed through the sleeve-cap subassembly and the cap 262 is screwed onto or bonded with the housing 261. The proximal end 269 can include a threaded portion 270 adapted for threaded engagement with a rotation knob 271 located at the proximal end portion of the housing 261. Thus, the coupling mechanism comprises the tip/tip-actuator subassembly screwed into the rotation knob 271 to form an actuator-knob subassembly.

An interlock arrangement 272 is configured to retain the knob 271 on the housing 261 and allow the knob 271 to rotate relative to the housing 261. The interlock arrangement 272 can include an annular rib disposed on the housing 261 and a groove disposed on the knob 271. A clearance is provided between the groove and the rib so as to allow the knob 271 to rotate freely relative to the housing 261. The knob 271 can be pressed onto the housing 261 and thus spins freely on housing 261 without coming off because of an interlock arrangement 272.

With reference to FIGS. 54A and 54C, the housing 261 can include a slot line 273 at a location perpendicular to a longitudinal axis 275 of the housing. One side of the slot line 273 can be drilled through to the opposite side of the housing, thus allowing an anti-rotation pin 274 to extend therethrough.

FIG. 54C shows a top cross-sectional view, identified as section 3-3 of FIG. 54A, with the anti-rotation pin 274 aligned with the slot 276. During assembly, of the injector 260, the tip actuator 267 is rotated until the slot 276 is aligned with the drilled hole adapted for the anti-rotation pin 274 to extend into the drilled hole. The anti-rotation pin 274 is pressed through a first side of housing, through the tip actuator, and through a second opposite side of housing.

In operation, one or more stents are placed over the member 264 and against the blunt front end of the sleeve 265. After the injector approaches the target site, the elongate member 264 and the first stent are pressed into tissue where implantation is to take place. In an ab interno procedure, the first tissue is the trabecular meshwork facing the anterior chamber. In an ab externo procedure, the first tissue is the trabecular meshwork facing Schlemm's canal. Once the first stent is in a proper location, the knob 271 is rotated to withdraw the elongate member 264, leaving the first stent in place. Stents can be snugly held onto the tip 264 with a mechanical feature on the elongate member, such as the holding members 245 described above with reference to FIGS. 51A-D. Optionally, the sleeve 265 can include a mechanical feature for holding stents in place. Further viscoelastic material or other means can be provided for holding the stents so that stent deployment does not occur until desired.

Figure 55:
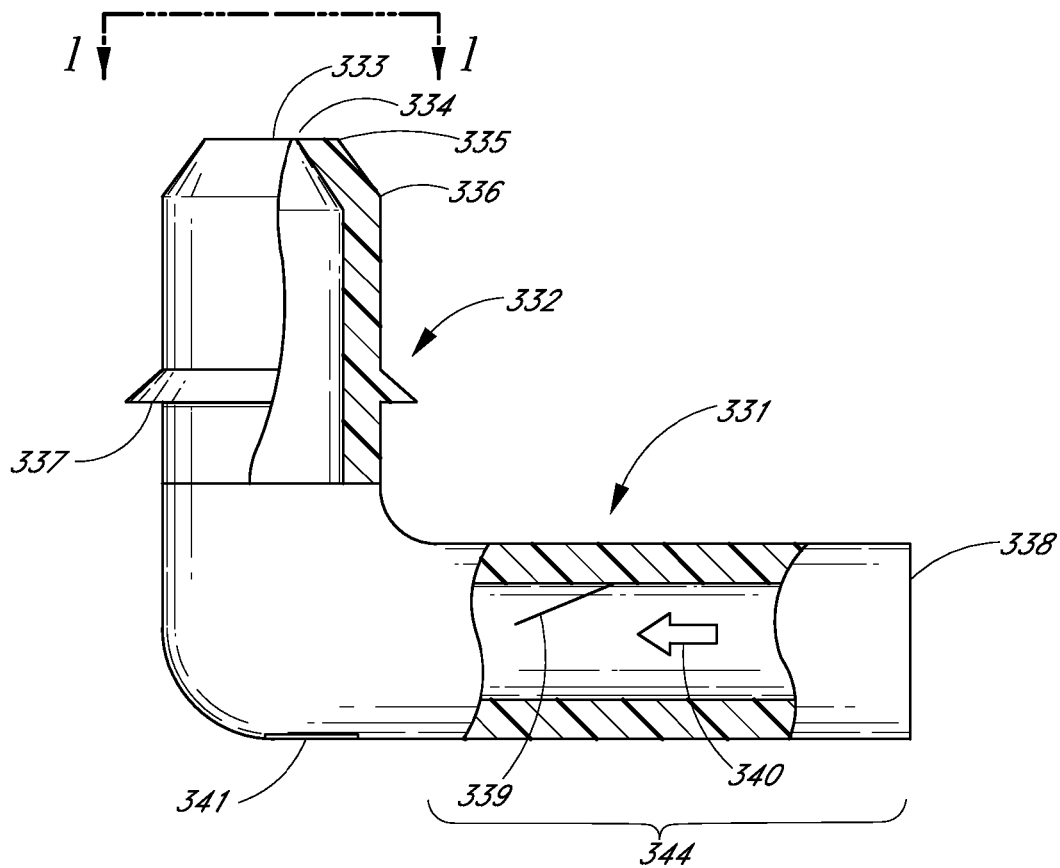
FIG. 55 shows an embodiment of a seton implant constructed according to the principles of the invention.

FIG. 55 shows an embodiment of the seton implant 331 constructed according to the principles of the invention. The seton implant may comprise a biocompatible material, such as a medical grade silicone, for example, the material sold under the trademark Silastic™, which is available from Dow Corning Corporation of Midland, Mich., or polyurethane, which is sold under the trademark Pellethane™, which is also available from Dow Corning Corporation. In an alternate embodiment, other biocompatible materials (biomaterials) may be used, such as polyvinyl alcohol, polyvinyl pyrrolidone, collagen, heparinized collagen, tetrafluoroethylene, fluorinated polymer, fluorinated elastomer, flexible fused silica, polyolefin, polyester, polysilicon, mixture of biocompatible materials, and the like. In a further alternate embodiment, a composite biocompatible material by surface coating the above-mentioned biomaterial may be used, wherein the coating material may be selected from the group consisting of polytetrafluoroethylene (PTFE), polyimide, hydrogel, heparin, therapeutic drugs, and the like.

The main purpose of the seton implant is to assist in facilitating the outflow of aqueous in an outward direction 340 into the Schlemm's canal and subsequently into the aqueous collectors and the aqueous veins so that the intraocular pressure is balanced. In one embodiment, the seton implant 331 comprises an elongated tubular element having a distal section 332 and an inlet section 344. A rigid or flexible distal section 332 is positioned inside one of the existing outflow pathways. The distal section may have either a tapered outlet end 333 or have at least one ridge 337 or other retention device protruding radially outwardly for stabilizing the seton implant inside the existing outflow pathways after implantation. For stabilization purposes, the outer surface of the distal section 332 may comprise a stubbed surface, a ribbed surface, a surface with pillars, a textured surface, or the like. The outer surface 336, including the outer region 335 and inner region 334 at the outlet end 333, of the seton implant is biocompatible and tissue compatible so that the interaction/irritation between the outer surface and the surrounding tissue is minimized. The seton implant may comprise at least one opening at a location proximal the distal section 332, away from the outlet end 333, to allow flow of aqueous in more than one direction. The at least one opening may be located on the distal section 332 at about opposite of the outlet end 333.

In another exemplary embodiment, the seton implant 331 may have a one-way flow controlling means 339 for allowing one-way aqueous flow 340. The one-way flow controlling means 339 may be selected from the group consisting of a check valve, a slit valve, a micropump, a semi-permeable membrane, or the like. To enhance the outflow efficiency, at least one optional opening 341 in the proximal portion of the distal section 332, at a location away from the outlet end 333, and in an exemplary embodiment at the opposite end of the outlet end 333, is provided.

Figure 56:
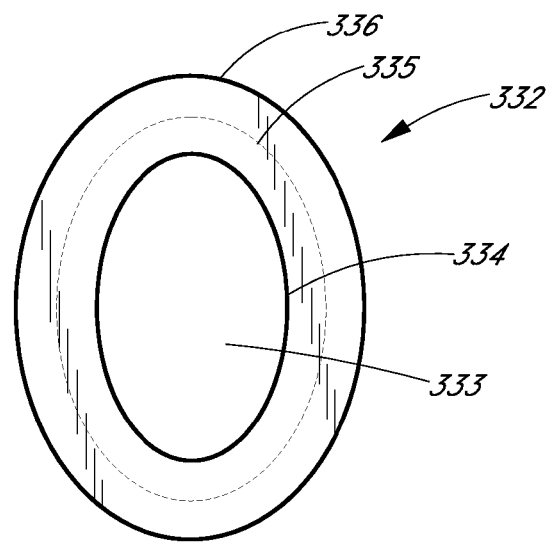
FIG. 56 is a top cross-sectional view of section 1-1 of FIG. 55.

FIG. 56 shows a top cross-sectional view of FIG. 55. The shape of the opening of the outlet end 333 and the remaining body of the distal section 332 may be oval, round or some other shape adapted to conform to the shape of the existing outflow pathways. This configuration will match the contour of Schlemm's canal to stabilize the inlet section with respect to the iris and cornea by preventing rotation.

As shown in FIG. 55, the seton implant of the present invention may have a length between about 0.5 mm to over a meter, depending on the body cavity the seton implant applies to. The outside diameter of the seton implant may range from about 30 µm to about 500 µm. The lumen diameter is preferably in the range between about 20 µm to about 150 µm. The seton implant may have a plurality of lumens to facilitate multiple flow transportation. The distal section may be curved at an angle between about 30 degrees to about 150 degrees, in an exemplary embodiment at around 70-110 degrees, with reference to the inlet section 344.

Figure 57:
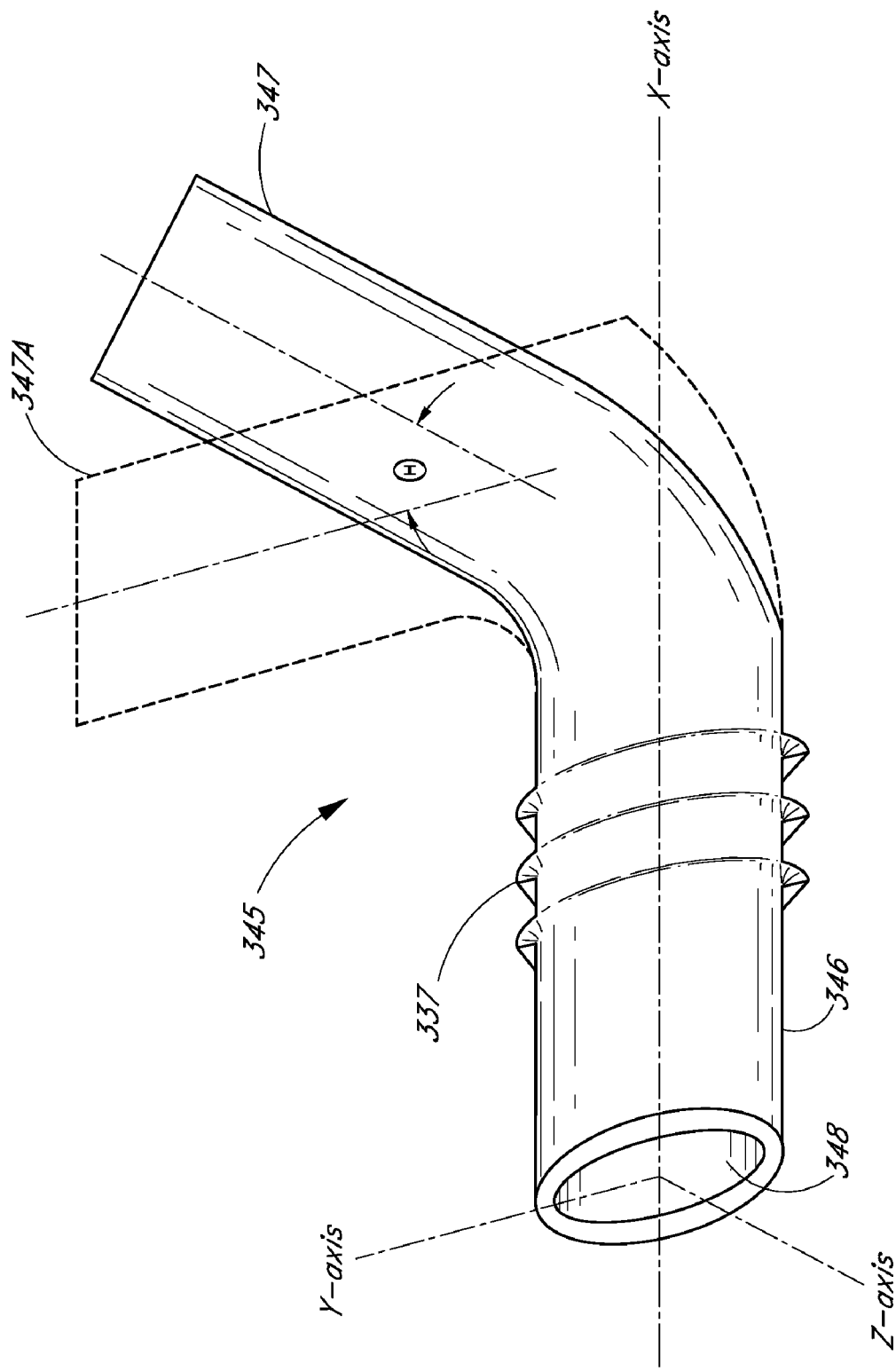
FIG. 57 is another embodiment of a seton implant constructed in accordance with the principles of the invention.

FIG. 57 shows another embodiment of the seton implant 345 constructed in accordance with the principles of the invention. In an exemplary embodiment, the seton implant 345 may comprise at least two sections: an inlet section 347 and an outlet section 346. The outlet section has an outlet opening 48 that is at the outlet end of the seton implant 345. The shape of the outlet opening 348 is preferably an oval shape to conform to the contour of the existing outflow pathways. A portion of the inlet section 347 adjacent the joint region to the outlet section 346 will be positioned essentially through the diseased trabecular meshwork while the remainder of the inlet section 347 and the outlet section 346 are outside the trabecular meshwork. As shown in FIG. 5, the long axis of the oval shape opening 348 lies in a first plane formed by an X-axis and a Y-axis. To better conform to the anatomical contour of the anterior chamber 20, the trabecular meshwork 21 and the existing outflow pathways, the inlet section 347 may preferably lie at an elevated second plane, at an angle θ, from the first plane formed by an imaginary inlet section 347A and the outlet section 346. The angle θ may be between about 30 degrees and about 150 degrees.

After the first stent is implanted, the injector is slightly withdrawn away from the trabecular meshwork. The tip of the injector is moved and pointed to a second target site without withdrawing the injector from the incision on the sclera. This re-positioning of the injector can be accomplished with a steerable section of the injector 260 noted above.

The term "targeted placement" of trabecular stents refers to the intentional placement of a stent at a particular location in Schlemm's canal for the purpose of providing a maximum benefit in the form of maximum outflow facility. With reference to FIG. 50A, aqueous enters Schlemm's canal 22 through the trabecular meshwork 21 and travels along the canal to exit through the collector channels 23. Schlemm's canal is a narrow channel with approximate dimensions of 250 µm×20 µm with a 40 mm length (Volume ~0.2 µl) and it provides measurable resistance to the flow of aqueous. Therefore, placing a stent into Schlemm's canal 22 through the trabecular meshwork 21 yields the best improvement in outflow facility when it is placed near a large collector channel 23 or a group of smaller ones that combine to have a larger hydraulic diameter. It is one aspect of the present invention to locate/detect the most appropriate collector channel(s) to implant a trabecular shunting stent adjacent the collector channel(s) 23.

The term "Multi-stent therapy" refers to the intentional placement of a stent in each of several locations in Schlemm's canal 22. Since Schlemm's canal 22 has measurable resistance to flow at physiological flow rates, a plurality of stents is strategically placed close to concentrations of collector ducts 23 or a large collector and distributed around Schlemm's canal 22 to maximize the impact of multiple stents.

An injector or device applicator to hold a plurality of serial devices has advantages of placing the device one at a time without reloading the device or without completely withdrawing the applicator out of a portion of the body. The advantages may include saving operating time, reducing redundant incision or injury, or exact positioning for device placement.

By way of example, but without limitation, an injector or device applicator for multiple device deployment may be used for implanting punctum plugs in an eye, for implanting drug-eluting devices into sclera tissue of an eye, implanting drug-eluting devices into tissue of a posterior segment, or implanting cardiovascular stents. Some aspects of at least one of the inventions disclosed herein relate to a method of multiple device deployment comprising: (a) loading a plurality of devices within a device-retaining space of a device applicator; (b) delivering the applicator to a first target implant site; (c) deploying a first device at the first target implant site; (d) detaching the applicator from the first target implant site; (e) directing the applicator to a second target implant site; (f) deploying a second device at the second target implant site; and (g) withdrawing the applicator.

The device of the exemplary embodiment preferably comprises a biocompatible material such that inflammation arising due to irritation between the outer surface of the device and the surrounding tissue is minimized. Biocompatible materials which may be used for the device 81 preferably include, but are not limited to, titanium, titanium alloys, polypropylene, nylon, PMMA (polymethyl methacrylate), medical grade silicone, e.g., Silastic™, available from Dow Corning Corporation of Midland, Mich.; and polyurethane, e.g., Pellethane™, also available from Dow Corning Corporation.

In other embodiments, the device of the embodiments may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and/or a mixture of the aforementioned biocompatible materials, and the like. In still other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists and other anti-glaucoma drugs, or antibiotics), and the like.

Figure 58:
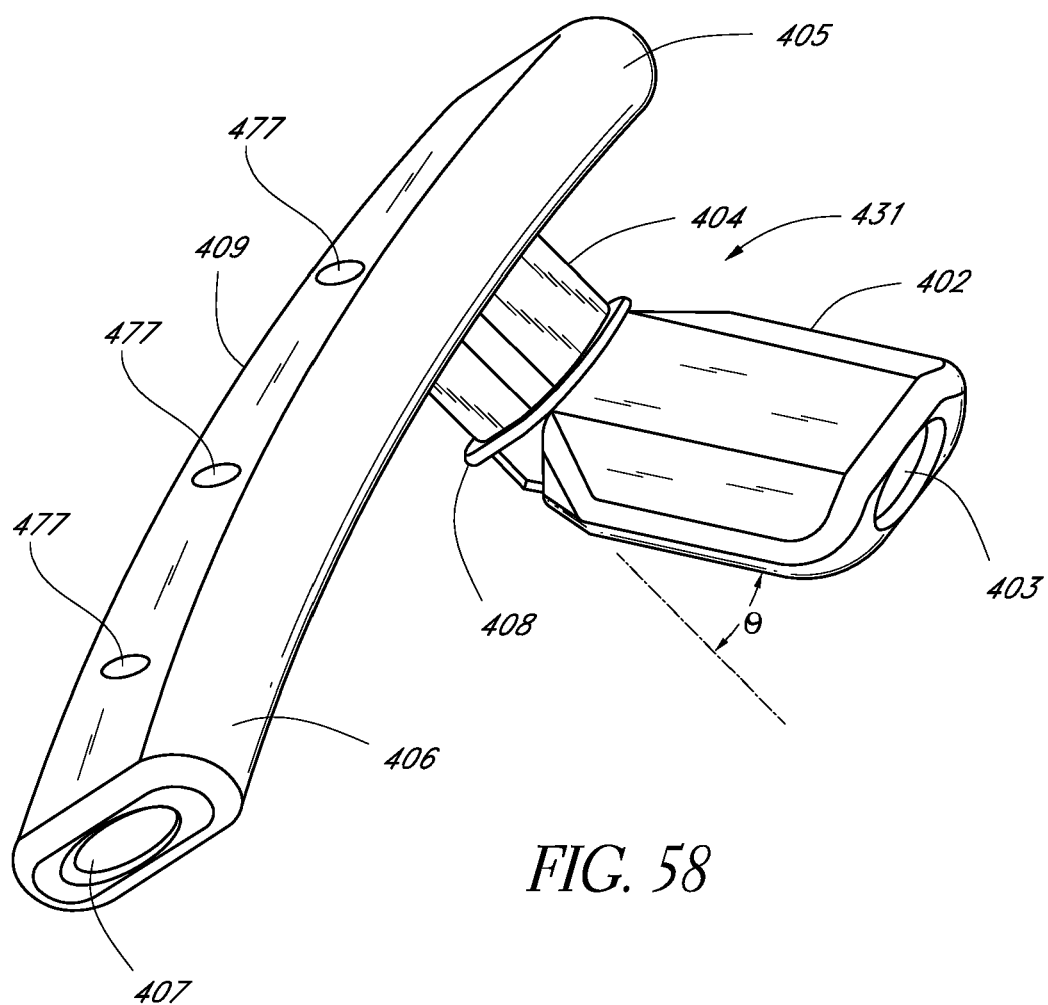
FIG. 58 is an oblique elevation view of one embodiment of a trabecular stenting device.

FIG. 58 illustrates a preferred embodiment of a trabecular shunting/stenting device 431, which facilitates the outflow of aqueous from the anterior chamber 20 into Schlemm's canal 22, and subsequently into the aqueous collectors and the aqueous veins so that intraocular pressure is reduced. In the illustrated embodiment, the trabecular stenting device 431 comprises an inlet section 402, having an inlet opening 403, a middle section 404, and an outlet section 409. The middle section 404 may be an extension of, or may be coextensive with, the inlet section 402. The outlet section 409 is preferably somewhat flexible to facilitate positioning of the outlet section 409 within an outflow pathway of the eye 10. The outlet section 409 is preferably substantially perpendicular to the middle section 404. "Substantially perpendicular," as used herein, is defined as subtending an angle between longitudinal axes of the sections 404, 409 ranging between about 30 degrees and about 150 degrees. The device 431 further comprises at least one lumen 407 within sections 404 and 409 which is in fluid communication with the inlet opening 403 of section 402, thereby facilitating transfer of aqueous through the device 431.

In one embodiment, the outlet section 409 has at least one outlet end. In another embodiment, the outlet section preferably has a first outlet end 406 and a second, opposite outlet end 405. The lumen 407 within the outlet section 409 opens to at least one of the outlet ends 405, 406. Furthermore, the outlet section 409 may have a plurality of side openings 477, each of which is in fluid communication with the lumen 407, for transmission of aqueous. The middle section 404 is connected to or coextensive with the outlet section 409 and is disposed between the first outlet end 406 and the second outlet end 405. In a preferred embodiment, the outlet section 409 is curved around a point, or a curve center, and the middle section 404 extends substantially along a plane that contains the curve center. In this embodiment, the outlet section 409 has a radius of curvature ranging between about 4 mm and about 10 mm.

As will be apparent to a person skilled in the art, the lumen 407 and the remaining body of the outlet section 409 may have a cross-sectional shape that is oval, circular, or other appropriate shape. The cross-sectional shapes of the lumen 407 and the outlet section 409 preferably conform to the shape of the outflow pathway into which the outlet section 409 is placed. The opening of the lumen 407 of the outlet ends 405, 406 may be ovoid in shape to match the contour of Schlemm's canal 22. Further, an outer contour of the outlet section 409 may be elliptical (e.g., ovoid) in shape to match the contour of Schlemm's canal 22. This serves to minimize rotational movement of the outlet section 409 within Schlemm's canal 22, and thereby stabilizes the inlet section 402 with respect to the iris and cornea.

A circumferential ridge 408 is provided at the junction of the inlet section 402 and the middle section 404 to facilitate stabilization of the device 431 once implanted within the eye 10. Preferably, the middle section 404 has a length (between the ridge 408 and the outlet section 409) that is roughly equal to a thickness of the trabecular meshwork 21, which typically ranges between about 100 μm and about 300 μm. In addition, the outlet section 409 may advantageously be formed with a protuberance or spur projecting therefrom so as to further stabilize the device 431 within the eye 10 without undue suturing.

Figure 63:
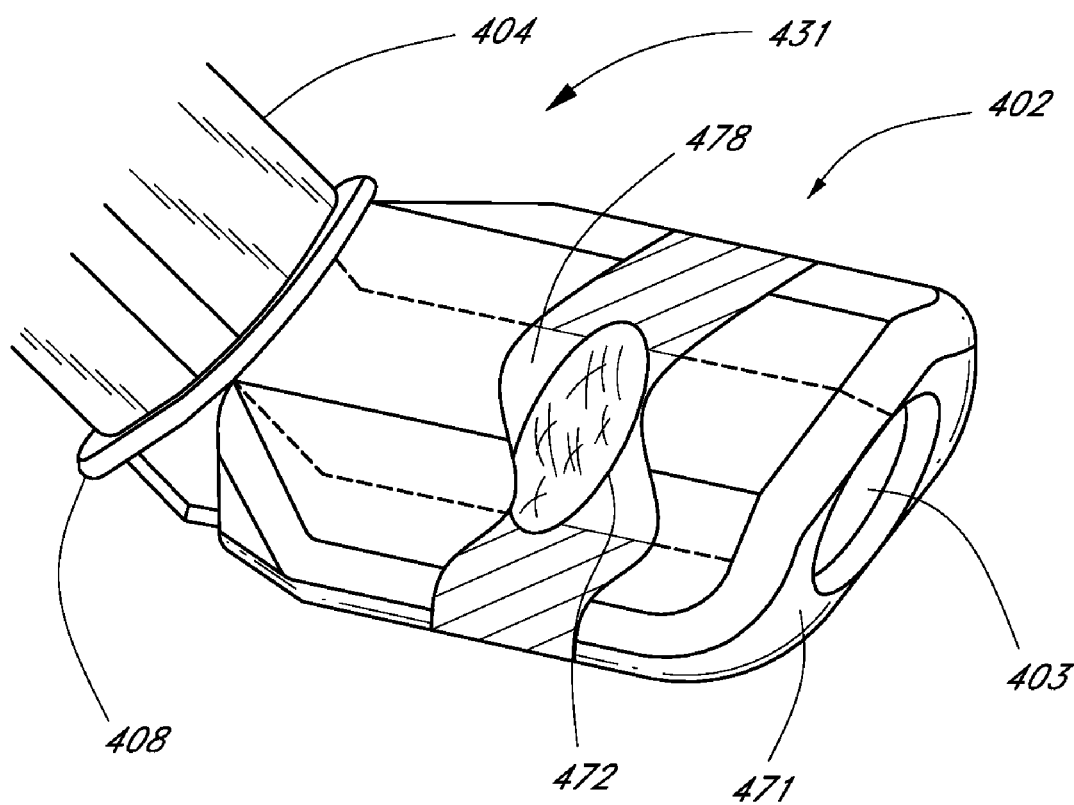
FIG. 63 is a close-up, cut-away view of an inlet section of the trabecular stenting device of FIGS. 58 and 59, illustrating a flow-restricting member retained within a lumen of the trabecular stenting device.

FIG. 63 is a close-up view of the inlet section 402 of the trabecular stenting device 431, illustrating a flow-restricting member 472, which is tightly retained within a lumen 478. The flow-restricting member 472 is shown located close to an inlet side 471 of the inlet section 402. The flow-restricting member 472 serves to selectively restrict at least one component in blood from moving retrograde, i.e., from the outlet section 409 into the anterior chamber 20 of the eye 10. Alternatively, the flow-restricting member 472 may be situated in any location within the device 431 such that blood flow is restricted from retrograde motion. The flow-restricting member 472 may, in other embodiments, be a filter made of a material selected from the following filter materials: expanded polytetrafluoroethylene, cellulose, ceramic, glass, Nylon, plastic, and fluorinated material such as polyvinylidene fluoride ("PVDF") (trade name: Kynar, by DuPont).

The trabecular stenting device 431 may be made by molding, thermo-forming, or other micro-machining techniques. The trabecular stenting device 431 preferably comprises a biocompatible material such that inflammation arising due to irritation between the outer surface of the device 431 and the surrounding tissue is minimized. Biocompatible materials which may be used for the device 431 preferably include, but are not limited to, titanium, medical grade silicone, e.g., Silastic™, available from Dow Corning Corporation of Midland, Mich.; and polyurethane, e.g., Pellethane™, also available from Dow Corning Corporation. In other embodiments, the device 431 may comprise other types of biocompatible material, such as, by way of example, polyvinyl alcohol, polyvinyl pyrolidone, collagen, heparinized collagen, polytetrafluordethylene, expanded polytetrafluoroethylene, fluorinated polymer, fluorinated elastomer, flexible fused silica, polyolefin, polyester, polysilicon, and/or a mixture of the aforementioned biocompatible materials, and the like. In still other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists and other anti-glaucoma drugs, or antibiotics), and the like.

As is well known in the art, a device coated or loaded with a slow-release substance can have prolonged effects on local tissue surrounding the device. The slow-release delivery can be designed such that an effective amount of substance is released over a desired duration. "Substance," as used herein, is defined as any therapeutic or bioactive drug or agents that can stop, mitigate, slow-down or reverse undesired disease processes.

In one embodiment, the device 431 may be made of a biodegradable (also including bioerodible) material admixed with a substance for substance slow-release into ocular tissues. In another embodiment, polymer films may function as substance containing release devices whereby the polymer films may be coupled or secured to the device 431. The polymer films may be designed to permit the controlled release of the substance at a chosen rate and for a selected duration, which may also be episodic or periodic. Such polymer films may be synthesized such that the substance is bound to the surface or resides within a pore in the film so that the substance is relatively protected from enzymatic attack. The polymer films may also be modified to alter their hydrophilicity, hydrophobicity and vulnerability to platelet adhesion and enzymatic attack. In one embodiment, the polymer film is made of biodegradable material.

Furthermore, the film may be coupled (locally or remotely) to a power source such that when substance delivery is desired, a brief pulse of current is provided to alter the potential on the film to cause the release of a particular amount of the substance for a chosen duration. Application of current causes release of a substance from the surface of the film or from an interior location in the film such as within a pore. The rate of substance delivery is altered depending on the degree of substance loading on the film, the voltage applied to the film, and by modifying the chemical synthesis of substance delivery polymer film.

The power-activated substance delivery polymer film may be designed to be activated by an electromagnetic field, such as, by way of example, NMR, MRI, or short range RF transmission (such as a Bluetooth® apparatus). In addition, ultrasound can be used to cause a release of a particular amount of substance for a chosen duration. This is particularly applicable to a substance coated device or a device made of a substrate containing the desired substance.

The device 431 may be used for a direct release of pharmaceutical preparations into ocular tissues. As discussed above, the pharmaceuticals may be compounded within the device 431 or form a coating on the device 431. Any known drug therapy for glaucoma may be utilized, including but not limited to, the following:

U.S. Pat. No. 6,274,138, issued Aug. 14, 2001, and U.S. Pat. No. 6,231,853, issued May 15, 2001, the entire contents of both of which are incorporated herein by reference, disclose the function of mitochondria and toxic substances synthesized as a metabolic byproduct within mitochondria of cells. Perry and associates (Perry H D et al. "Topical cyclosporin A in the management of postkeratoplasty glaucoma" *Cornea* 16:284-288, 1997) report that topical cyclosporin-A has been shown to reduce post-surgical increases in intraocular pressure. It is proposed that such compounds with known effects on mitochondrial stability might be effective in treating trabecular meshwork. An antagonistic drug to neutralize the toxic byproduct or a stabilizing drug to effect mitochondrial stability is believed able to restore the mitochondria function and subsequently mitigate the dysfunction of the trabecular meshwork.

U.S. Pat. No. 6,201,001, issued Mar. 13, 2001, the entire contents of which are incorporated herein by reference, discloses Imidazole antiproliferative agents useful for neovascular glaucoma.

U.S. Pat. No. 6,228,873, issued May 8, 2001, the entire contents of which are incorporated herein by reference, discloses a new class of compounds that inhibit function of sodium chloride transport in the thick ascending limb of the loop of Henle, wherein the preferred compounds useful are furosemide, piretanide, benzmetanide, bumetanide, torasernide and derivatives thereof.

U.S. Pat. No. 6,194,415, issued Feb. 27, 2001, the entire contents of which are incorporated herein by reference, discloses a method of using quinoxalines (2-imidazolin-2-ylamino) in treating neural injuries (e.g., glaucomatous nerve damage).

U.S. Pat. No. 6,060,463, issued May 9, 2000, and U.S. Pat. No. 5,869,468, issued Feb. 9, 1999, the entire contents of which are incorporated herein by reference, disclose treatment of conditions of abnormally increased intraocular pressure by administration of phosphonylmethoxyalkyl nucleotide analogs and related nucleotide analogs.

U.S. Pat. No. 5,925,342, issued Jul. 20, 1999, the entire contents of which are incorporated herein by reference, discloses a method for reducing intraocular pressure by administration of potassium channel blockers.

U.S. Pat. No. 5,814,620, issued Sep. 29, 1998, the entire contents of which are incorporated herein by reference, discloses a method of reducing neovascularization and of treating various disorders associated with neovascularization. These methods include administering to a tissue or subject a synthetic oligonucleotide.

U.S. Pat. No. 5,767,079, issued Jun. 16, 1998, the entire contents of which are incorporated herein by reference, discloses a method for treatment of ophthalmic disorders by applying an effective amount of Transforming Growth Factor-Beta (TGF-beta) to the affected region.

U.S. Pat. No. 5,663,205, issued Sep. 2, 1997, the entire contents of which are incorporated herein by reference, discloses a pharmaceutical composition for use in glaucoma treatment which contains an active ingredient 5-[1-hydroxy-2-[2-(2-methoxyphenoxyl)ethylamino]ethyl]-2-methylbenzenesulfonamide. This agent is free from side effects, and stable and has an excellent intraocular pressure reducing activity at its low concentrations, thus being useful as a pharmaceutical composition for use in glaucoma treatment.

U.S. Pat. No. 5,652,236, issued Jul. 29, 1997, the entire contents of which are incorporated herein by reference, discloses pharmaceutical compositions and a method for treating glaucoma and/or ocular hypertension in the mammalian eye by administering thereto a pharmaceutical composition which contains as the active ingredient one or more compounds having guanylate cyclase inhibition activity. Examples of guanylate cyclase inhibitors utilized in the pharmaceutical composition and method of treatment are methylene blue, butylated hydroxyanisole and N-methylhydroxylamine.

U.S. Pat. No. 5,547,993, issued Aug. 20, 1996, the entire contents of which are incorporated herein by reference, discloses that 2-(4methylaminobutoxy) diphenylmethane or a hydrate or pharmaceutically acceptable salt thereof have been found useful for treating glaucoma.

U.S. Pat. No. 5,502,052, issued Mar. 26, 1996, the entire contents of which are incorporated herein by reference, discloses use of a combination of apraclonidine and timolol to control intraocular pressure. The compositions contain a combination of an alpha-2 agonist (e.g., para-amino clonidine) and a beta blocker (e.g., betaxolol).

U.S. Pat. No. 6,184,250, issued Feb. 6, 2001, the entire contents of which are incorporated herein by reference, discloses use of cloprostenol and fluprostenol analogues to treat glaucoma and ocular hypertension. The method comprises topically administering to an affected eye a composition comprising a therapeutically effective amount of a combination of a first compound selected from the group consisting of beta-blockers, carbonic anhydrase inhibitors, adrenergic agonists, and cholinergic agonists, together with a second compound.

U.S. Pat. No. 6,159,458, issued Dec. 12, 2000, the entire contents of which are incorporated herein by reference, discloses an ophthalmic composition that provides sustained release of a water soluble medicament formed by comprising a crosslinked carboxy-containing polymer, a medicament, a sugar and water.

U.S. Pat. No. 6,110,912, issued Aug. 29, 2000, the entire contents of which are incorporated herein by reference, discloses methods for the treatment of glaucoma by administering an ophthalmic preparation comprising an effective amount of a non-corneotoxic serine-threonine kinase inhibitor, thereby enhancing aqueous outflow in the eye and treatment of the glaucoma. In some embodiments, the method of administration is topical, whereas it is intracameral in other embodiments. In still further embodiments, the method of administration is intracanalicular.

U.S. Pat. No. 6,177,427, issued Jan. 23, 2001, the entire contents of which are incorporated herein by reference, discloses compositions of non-steroidal glucocorticoid antagonists for treating glaucoma or ocular hypertension.

U.S. Pat. No. 5,952,378, issued Sep. 14, 1999, the entire contents of which are incorporated herein by reference, discloses the use of prostaglandins for enhancing the delivery of drugs through the uveoscleral route to the optic nerve head for treatment of glaucoma or other diseases of the optic nerve as well as surrounding tissue. The method for enhancing the delivery to the optic nerve head comprises contacting a therapeutically effective amount of a composition containing one or more prostaglandins and one or more drug substances with the eye at certain intervals.

Figure 59:
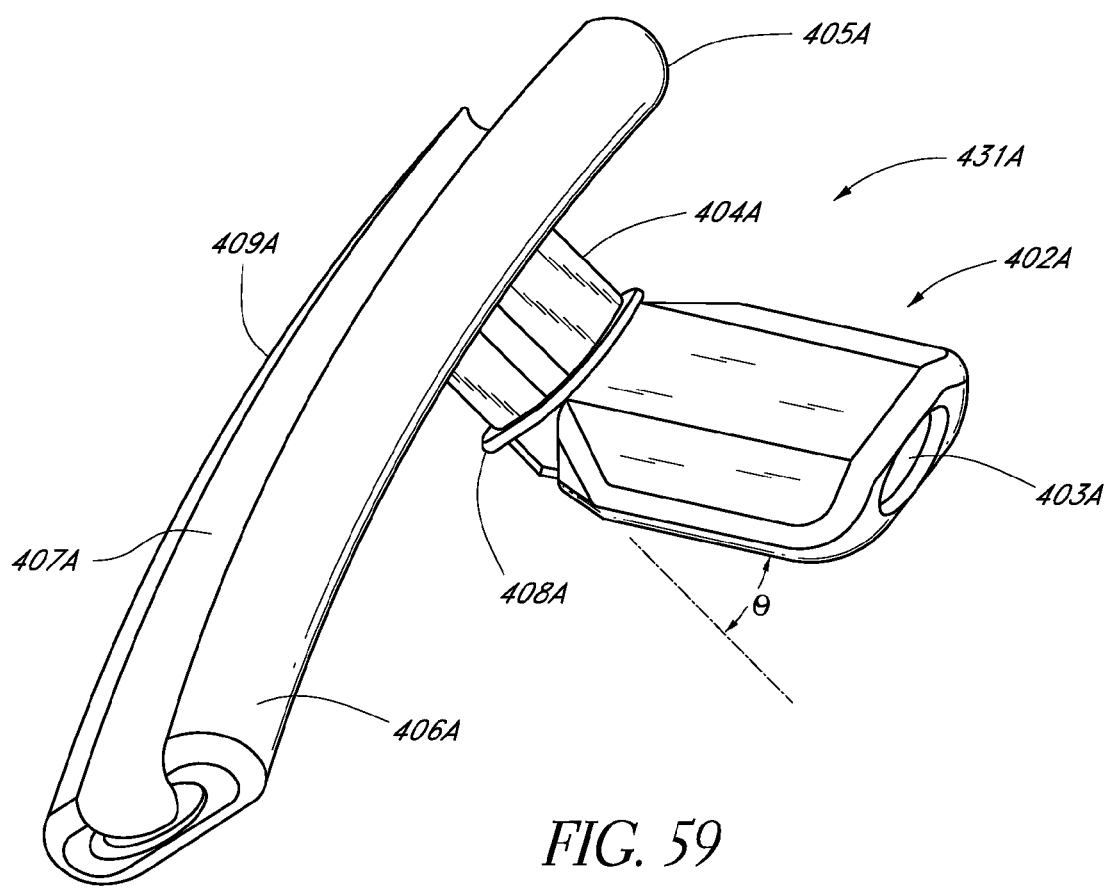
FIG. 59 is an oblique elevation view of another embodiment of a trabecular stenting device.

FIG. 59 illustrates another embodiment of a trabecular stenting device 431A that facilitates the outflow of aqueous from the anterior chamber 20 into Schlemm's canal 22, and subsequently into the aqueous collectors and the aqueous veins so that intraocular pressure is reduced. The device 431A comprises an inlet section 402A, a middle section 404A, and an outlet section 409A. The device 431A further comprises at least one lumen 403A traversing the sections 402A, 404A, 409A and providing fluid communication therebetween. The lumen 403A facilitates the transfer of aqueous from the inlet section 402A through the device 431A. The outlet section 409A is preferably curved, and may also be somewhat flexible, to facilitate positioning of the outlet section 409A within an existing outflow pathway of the eye 10. The outlet section 409A may further comprise an elongate trough 7A for transmitting, or venting, aqueous. The elongate trough 7A is connected to and in fluid communication with the lumen 403A within the trabecular stenting device 431A.

A circumferential ridge 8A is provided at the junction of the inlet section 402A and the middle section 404A to facilitate stabilization of the device 431A once implanted within the eye 10. Preferably, the middle section 404A has a length (between the ridge 8A and the outlet section 409A) that is roughly equal to the thickness of the trabecular meshwork 21, which typically ranges between about 100 μm and about 300 μm. In addition, the outlet section 409A may advantageously be formed with a protuberance or barb projecting therefrom so as to further stabilize the device 431A within the eye 10 without undue suturing.

As will be appreciated by those of ordinary skill in the art, the devices 431 and 431A may advantageously be practiced with a variety of sizes and shapes without departing from the scope of the invention. Depending upon the distance between the anterior chamber 20 and the drainage vessel (e.g., a vein) contemplated, the devices 431, 431A may have a length ranging from about 0.05 centimeters to over 10 centimeters. Preferably, the devices 431 and 431A have an outside diameter ranging between about 30 μm and about 500 μm, with the lumens 407, 403A having diameters ranging between about 20 μm and about 250 μm, respectively. In addition, the devices 431, 431A may have a plurality of lumens to facilitate transmission of multiple flows of aqueous. The inlet sections 402, 402A have longitudinal axes that form an angle (θ) ranging between about 20 degrees and about 150 degrees relative to the longitudinal axes of the middle sections 404, 404A, respectively. More preferably, the angles between the longitudinal axes of the inlet sections 402, 402A and the middle sections 404, 404A range between about 30 degrees and about 60 degrees, respectively.

One preferred method for increasing aqueous outflow in the eye 10 of a patient, to reduce intraocular pressure therein, comprises bypassing the trabecular meshwork 21. In operation, the middle section 404 of the device 431 is advantageously placed across the trabecular meshwork 21 through a slit or opening. This opening can be created by use of a laser, a knife, or other surgical cutting instrument. The opening may advantageously be substantially horizontal, i.e., extending longitudinally in the same direction as the circumference of the limbus 15. Other opening directions may also be used, as well. The opening may advantageously be oriented at any angle, relative to the circumference of the limbus 15, that is appropriate for inserting the device 431 through the trabecular meshwork 21 and into Schlemm's canal 22 or other outflow pathway, as will be apparent to those skilled in the art. The middle section 404 may be semi-flexible and/or adjustable in position relative to the inlet section 402 and/or the outlet section 409, further adapting the device 431 for simple and safe glaucoma implantation. Furthermore, the outlet section 409 may be positioned into fluid collection channels of the natural outflow pathways. Such natural outflow pathways include Schlemm's canal 22, aqueous collector channels, aqueous veins, and episcleral veins. The outlet section 409 may be positioned into fluid collection channels up to at least the level of the aqueous veins, with the device inserted in a retrograde or antegrade fashion.

Figure 60:
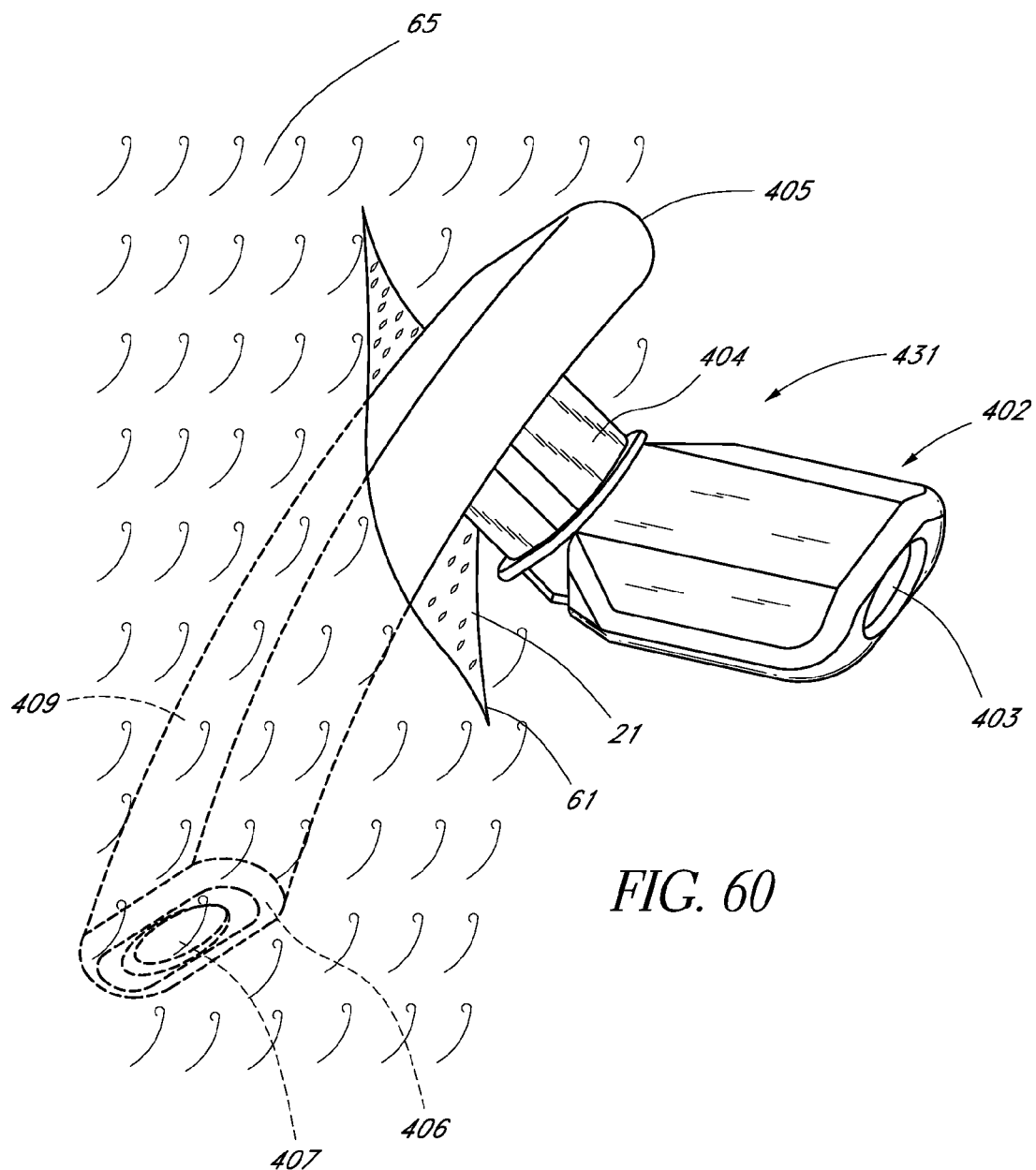
FIG. 60 is an oblique elevation view of placement of one end of a trabecular stenting device through a trabecular meshwork.

FIG. 60 generally illustrates a step in the implantation of the trabecular stenting device 431 through the trabecular meshwork 21. The outlet section 409 of the device 431 is inserted into an opening 61 in the trabecular meshwork 21. A practitioner may create the opening 61 "ab interno" from the interior surface 65 of the trabecular meshwork 21. The practitioner then advances the first outlet end 406 of the outlet section 409 through the opening 61 into a first side of Schlemm's canal 22 or other suitable outflow pathway within the eye 10. Next, the practitioner advances the second outlet end 405 through the opening 61 and into a second side of Schlemm's canal 22. The advancing of the second outlet end 405 may be facilitated by slightly pushing the second outlet end 405 through the opening 61.

Figure 62:
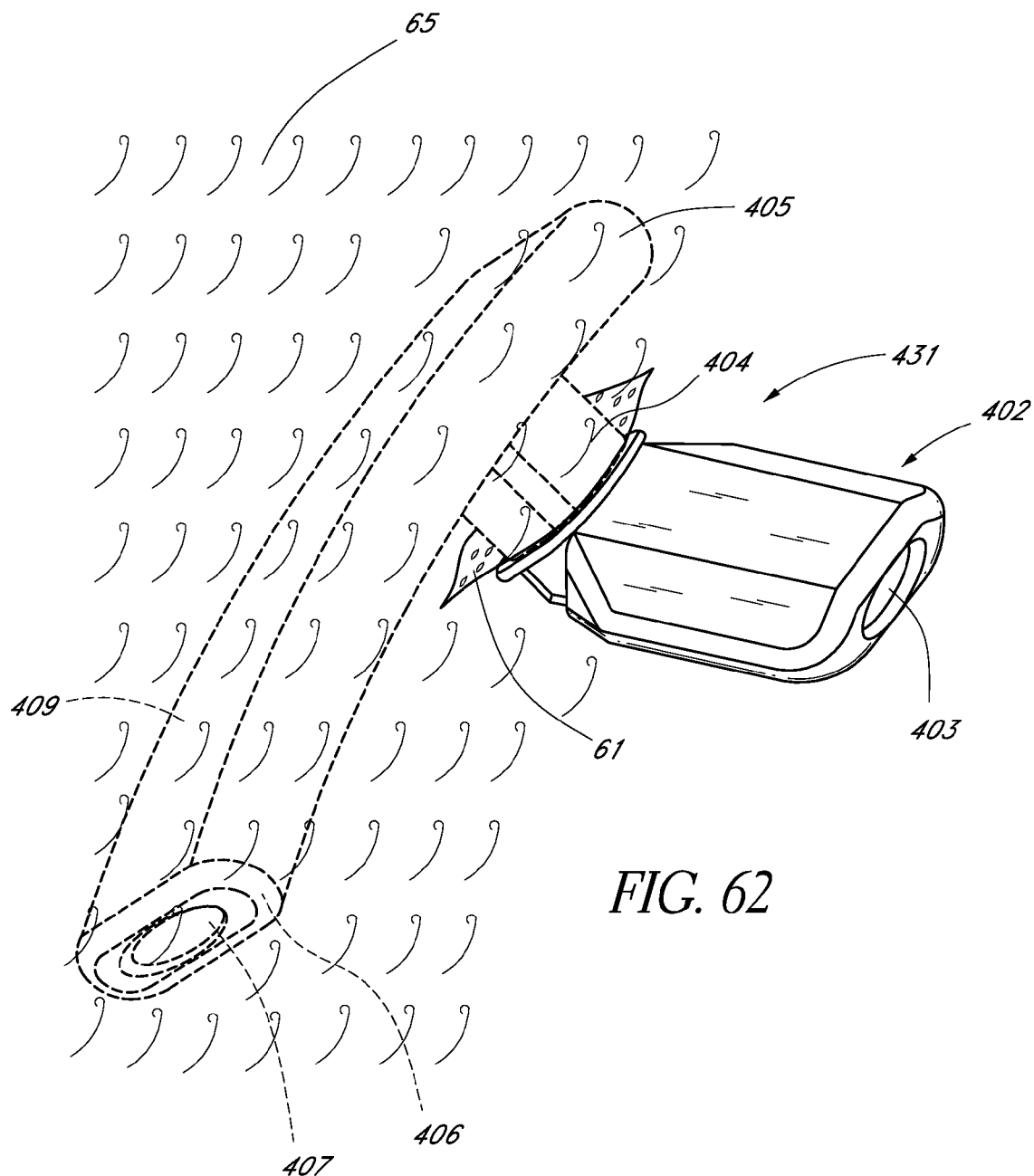
FIG. 62 is an oblique elevation view of a preferred implantation of a trabecular stenting device through a trabecular meshwork.

FIG. 62 generally illustrates a further stage in deployment of the device 31, wherein the entire outlet section 409 of the device 431 is implanted within Schlemm's canal 22, beneath the trabecular meshwork 21. At this stage, the lumen 403 of the implanted device 431 provides an enhanced fluid communication through the trabecular meshwork 21.

Figure 61:
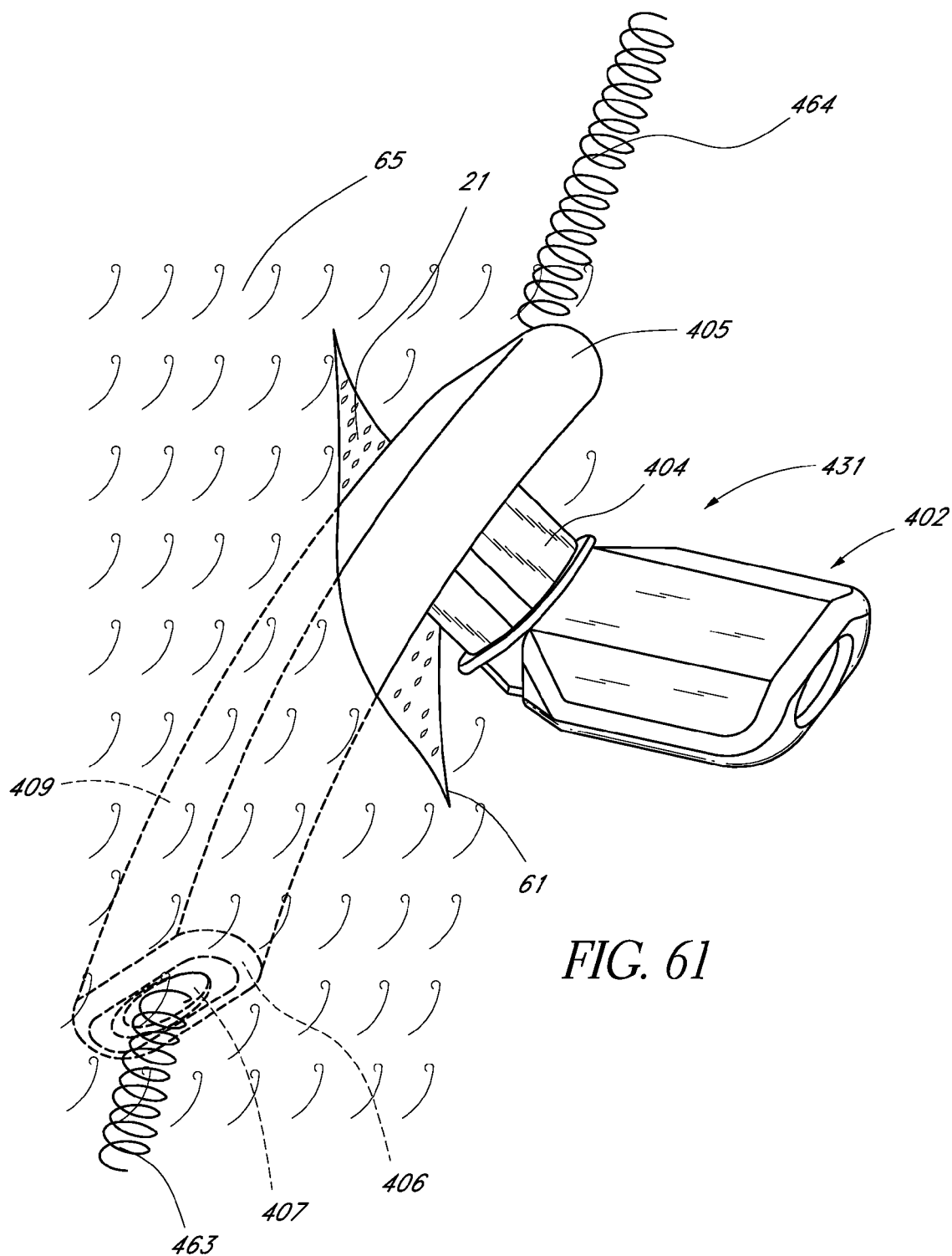
FIG. 61 is an oblique elevation view of placement of one end of a trabecular stenting device through a trabecular meshwork, wherein the trabecular stenting device is passed over a guidewire.

FIG. 61 shows an additional and/or alternate step in the implantation of the trabecular stenting device 431 through the trabecular meshwork 21. The practitioner inserts a distal end 463 of a guidewire 464 through the opening 61 into the first side of Schlemm's canal 22. The practitioner then advances the first outlet end 406 of the outlet section 409 into Schlemm's canal 22 by "riding," or advancing, the trabecular stenting device 431 on the guidewire 464. As will be apparent to those skilled in the art, the guidewire 464 will have a shape and size conforming to the shape and size of the lumen 7; and as such, may have an elliptical (e.g., oval) shape, a D-shape, a round shape, or an irregular (asymmetric) shape which is adapted for nonrotatory engagement for the device 31.

Another method for increasing aqueous outflow within the eye 10 of a patient, and thus reduce intraocular pressure therein, comprises: (a) creating an opening in the trabecular meshwork 21, wherein the trabecular meshwork 21 includes a deep side and superficial side; (b) inserting the trabecular stenting device 431 into the opening; and (c) transmitting aqueous through the device 31, to bypass the trabecular meshwork 21, from the deep side to the superficial side of the trabecular meshwork 21. This "transmitting" of aqueous is preferably passive, i.e., aqueous flows out of the anterior chamber 20 due to a pressure gradient between the anterior chamber 20 and the aqueous venous system 23.

Another method for increasing aqueous outflow within the eye 10 of a patient, and thus reduce intraocular pressure therein, comprises a) providing at least one bioactive substance incorporated into a trabecular stenting device at about the middle section of the device; b) implanting the trabecular stenting device within a trabecular meshwork of an eye such that the middle section is configured substantially within the trabecular meshwork, the stenting device having a first end positioned in an anterior chamber of the eye while a second end is positioned inside a Schlemm's canal, wherein the first and the second ends of the trabecular stenting device establish a fluid communication between the anterior chamber and the Schlemm's canal; and c) allowing the middle section of the trabecular stenting device to release a quantity of the bioactive substance into the trabecular meshwork. In another embodiment, the at least one bioactive substance or agent is incorporated into the device at about the outlet section for releasing the bioactive agent into Schlemm's canal and/or downstream of Schlemm's canal.

It should be understood that the devices 431 and 31A are in now way limited to implantation within only Schlemm's canal 20, as depicted in FIGS. 60 and 61. Rather, the devices 31 and 431A may advantageously be implanted within and/or used in conjunction with a variety of other natural outflow pathways, or biological tubular structures, as mentioned above. As will be apparent to those of ordinary skill in the art, the devices 431 and 431A may advantageously be used in conjunction with substantially any biological tubular structure without detracting from the scope of the invention.

Figure 64:
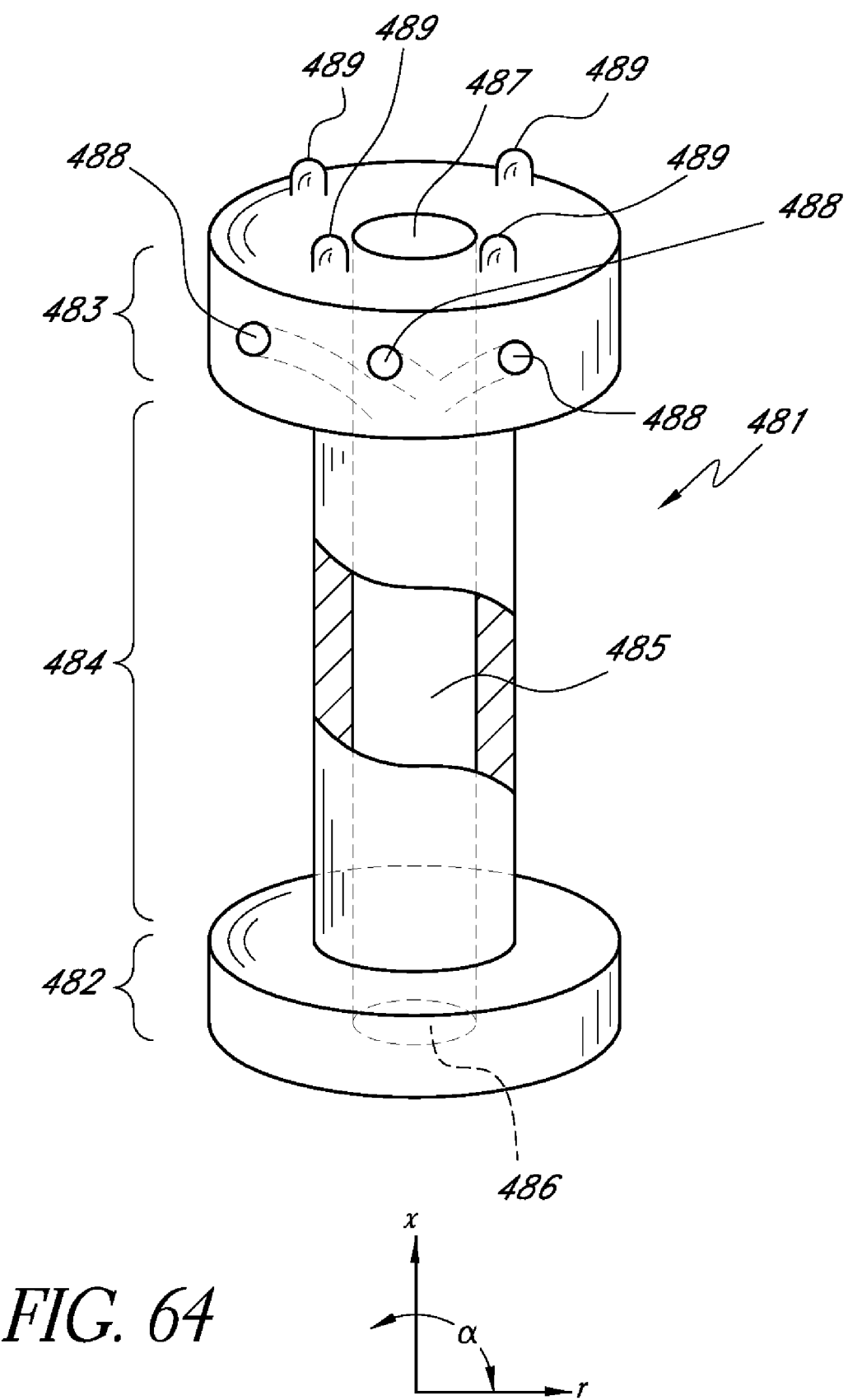
FIG. 64 is one embodiment of an axisymmetric trabecular stenting device for incorporating bioactive agents.

FIG. 64 shows one embodiment of an axisymmetric trabecular stenting device 481 according to the principles of the invention. An axisymmetric device 481 has a coordination of x, r and angle α as shown in FIG. 64, rather than depending on a conventional coordination of x, y, and z. The device 481 comprises an inlet (proximal) section 482, an outlet (distal) section 483 and a middle section 484 connecting the inlet section 482 and the outlet section 483. A lumen 485 of the device 481 is for transporting aqueous, liquid, or therapeutic agents between the inlet section and the outlet section, wherein the therapeutic agent is herein intended to include pharmaceutical agents, drugs, genes, cells, and/or growth factors. The inlet section 482 has at least one inlet opening 486 while the outlet section 483 comprises at least one outlet opening 487. In some aspect, the outlet section 483 may comprise a plurality of openings 487, 488 suitably located for outletting axisymmetrically the aqueous, liquid or therapeutic agents, wherein each of the openings 488 is in fluid communication with the lumen 485 of the device 481.

In one embodiment, at least one bioactive agent is loaded onto the exterior surface or into the pores of the exterior surface of the middle section 404, 484 of the stenting device 431, 481 enabling releasing into the trabecular meshwork upon device implantation. In general, the bioactive agents may comprise pharmaceutical agents, drugs, genes, cells, and/or growth factors. In some aspect, at least some bioactive agents may be loaded onto the inner surface or into the pores of the inner surface of the middle section of the stenting devices. In still a further aspect, the middle section 404, 484 may be constructed of porous material enabling the loaded therapeutic agents controllably releasing to the desired surrounding tissue, wherein the therapeutic agents are diffusible through the pores. Preferably, the middle section 484 has a length (between the inlet section 482 and the outlet section 483) that is roughly equal to a thickness of the trabecular meshwork 21, which typically ranges between about 100 μm and about 300 μm.

Some aspects of the invention provide a stent with at least one bioactive agent being loaded onto the exterior surface or into the pores of the exterior surface of the outlet section 409, 483 of the stenting device 431, 481 enabling releasing into Schlemm's canal or collector channels upon device implantation.

To further stenting Schlemm's canal after implanting the device 481, a plurality of elevated (that is, protruding axially) supports or pillars 489 is located at the distal-most end of the outlet section 483 sized and configured for allowing media (for example, aqueous, liquid, balanced salt solution, viscoelastic fluid, therapeutic agents, or the like) to be transported freely. Some aspects of the invention relate to the device 481 having a plurality of elevated (that is, protruding axially) supports or pillars 489 that are made of biodegradable material mixed with at least one bioactive agent. Once implanted, the bioactive agent is slowly released from the biodegradable supports 489 to treat the Schlemm's canal tissue.

In a further aspect, a plurality of the stenting device 481 is loaded in a cartridge to be inserted into a loading chamber of a device delivery applicator 451 or directly loaded inside the loading chamber of a device delivery applicator 451 enabling for multiple stents implantation. In this method, the distal end of the applicator 451 is movably positioned from one location at the trabecular meshwork after implanting a first stent to another location of the trabecular meshwork for implanting a second stent and so forth without withdrawing the applicator out of the anterior chamber of the eye.

Some aspects of the invention provide the device 431, 481 adapted for a direct release of at least one bioactive agent for treating ocular tissues. As discussed above, the bioactive or therapeutic agents may be compounded within the device 431, 481 or form a coating on the device 431, 481. Any known drug or non-drug therapeutic agents for glaucoma may be utilized, including but not limited to, the following:

U.S. Pat. No. 6,436,703, issued Aug. 20, 2002, the entire contents of which are incorporated herein by reference, discloses a method and compositions comprising novel isolated polypeptides, novel isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies. The compositions in '703 additionally include vectors, including expression vectors, containing the polynucleotides of the invention, cells genetically engineered to contain such polynucleotides and cells genetically engineered to express such polynucleotides, any of which might be effective in treating trabecular meshwork and/or ocular tissue in general;

U.S. Pat. No. 6,423,682, issued Jul. 23, 2002 and U.S. Pat. No. 6,485,920, issued Nov. 26, 2002, the entire contents of both of which are incorporated herein by reference, disclose the compositions of novel human growth factor antagonist proteins and active variants thereof, isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies function of mitochondria and toxic substances synthesized as a metabolic byproduct within mitochondria of cells. It is proposed that such compositions with known effects on mitochondrial stability might be effective in treating trabecular meshwork. An antagonistic drug to neutralize the toxic byproduct or a stabilizing drug to effect mitochondrial stability is believed able to restore the mitochondria function and subsequently mitigate the dysfunction of the trabecular meshwork;

U.S. Pat. No. 6,379,882, issued Apr. 30, 2002, the entire contents of which are incorporated herein by reference, discloses a method for reducing cellular damage related to myocardial infarction, glaucoma or another neurodegenerative disease by administering to a subject, a therapeutically effective amount of a test compound as determined by the relative efficacy of the test compound in reducing cell death due to the ischemic condition in an in vitro assay of growth factor or oxygen/glucose and growth factor-deprived retinal ganglion cells. In the present invention, the in vitro cell death of growth factor or oxygen/glucose and growth factor-deprived retinal ganglion cells generally occurs by an apoptotic or necrotic mechanism, wherein the test compound comprises a calcium channel blocker, an N-methyl-D-aspartate, and a bis-benzimidazole;

U.S. Pat. No. 6,489,305, issued Dec. 3, 2002, the entire contents of which are incorporated herein by reference, discloses a method for inhibiting proliferation of ocular fibroblasts or for ameliorating glaucoma surgery failure in a mammal, the method comprising administering to an eye of the mammal during or after glaucoma surgery a p21 cyclin dependent kinase inhibitor, wherein the cyclin dependent kinase inhibitor is administered as a polypeptide or as a nucleotide sequence that encodes the cyclin dependent kinase inhibitor administered in an adenoviral viral vector or administered on a sponge depot;

U.S. Pat. No. 6,455,283, issued Sep. 24, 2002, the entire contents of which are incorporated herein by reference, discloses a method of vascular endothelial growth factor-E (VEGF-E). VEGF-E is a novel polypeptide related to vascular endothelial growth factor (VEGF) and bone morphogenetic protein 1. VEGF-E has homology to VEGF including conservation of the amino acids required for activity of VEGF. VEGF-E can be useful in wound repair, as well as in the generation and regeneration of tissue. It is proposed that such VEGF, VEGF-E and their respective antagonists with known effects on tissue regeneration or anti-regeneration might be effective in treating trabecular meshwork or ocular tissue in general;

U.S. Pat. No. 6,476,211, issued Nov. 5, 2002, the entire contents of which are incorporated herein by reference, discloses human CD39-like protein polynucleotides isolated from cDNA libraries of human fetal liver-spleen and macrophage as well as polypeptides encoded by these polynucleotides and mutants or variants thereof. CD39 (cluster of differentiation 39) is a cell-surface molecule recognized by a "cluster" of monoclonal antibodies that can be used to identify the lineage or stage of differentiation of lymphocytes and thus to distinguish one class of lymphocytes from another. It is proposed that such CD39 polynucleotides with known effects on antibody specifics might be effective in treating trabecular meshwork or ocular tissue in general;

U.S. Pat. No. 5,780,052, issued Jul. 14, 1998, the entire contents of which are incorporated herein by reference, discloses a method of salvaging a target cell from cell death, comprising contacting a target cell having a disrupted cell membrane with a specific affinity reagent-liposome conjugate in an amount effective and for a time sufficient to allow the conjugate to prevent cell death due to membrane disruption. The patent discloses methods of delivering a selected agent into a damaged target cell for diagnosis and therapy, wherein the conjugate comprises a biological agent selected from the group consisting of fibroblastic growth factor-$\beta$, angiogenic factors, high energy substrates for the myocardium, antioxidants, cytokines and contrast agents, which might be effective in treating trabecular meshwork or ocular tissue in general;

U.S. Pat. No. 6,475,724, issued Nov. 5, 2002, the entire contents of which are incorporated herein by reference, discloses a method of treating glaucoma which comprises administering to a glaucomatous patient an effective amount of an agent that inhibits the synthesis if a TIGR (trabecular meshwork inducible glucocorticoid response) protein or gene, which might be effective in treating trabecular meshwork or ocular tissue in general;

U.S. Pat. No. 6,475,784, issued Nov. 5, 2002, the entire contents of which are incorporated herein by reference, discloses a method for polypeptides having anti-angiogenic activity and nucleic acids that encode these polypeptides. The anti-angiogenic polypeptides include at least kringles 1-3 of plasminogen. The patent '784 also provides methods of using the polypeptides and nucleic acids for inhibiting angiogenesis and other conditions characterized by undesirable endothelial cell proliferation. Angiostatin, which is an angiogenesis inhibitor, is a naturally occurring internal cleavage product of plasminogen, wherein human plasminogen has five characteristic protein domains called "kringle structures." It is proposed that such angiostatin with known effects on inhibiting angiogenesis might be effective in treating trabecular meshwork and/or ocular tissue in general;

U.S. Pat. No. 6,436,703, issued Aug. 20, 2002, the entire contents of which are incorporated herein by reference, discloses a method and compositions comprising novel isolated polypeptides, novel isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies. The compositions in '703 additionally include vectors, including expression vectors, containing the polynucleotides of the invention, cells genetically engineered to contain such polynucleotides and cells genetically engineered to express such polynucleotides, any of which might be effective in treating trabecular meshwork and/or ocular tissue in general;

U.S. Pat. No. 6,451,764, issued Sep. 17, 2002, the entire contents of which are incorporated herein by reference, discloses a method of treating vascular tissue and promoting angiogenesis in a mammal comprising administering to the mammal an effective amount of the composition comprising VRP (vascular endothelial growth factor-related protein). The disclosure '764 further provides a method for treating trauma affecting the vascular endothelium comprising administering to a mammal suffering from the trauma an effective amount of the composition containing the VRP, or a method for treating a dysfunctional state characterized by lack of activation or lack of inhibition of a receptor for VRP in a mammal. It is proposed that such angiogenesis promoter and its antagonists with known effects on promoting or inhibiting angiogenesis might be effective in treating trabecular meshwork and/or ocular tissue in general; and U.S. Pat. No. 5,986,168, issued Nov. 16, 1999, the entire contents of which are incorporated herein by reference, discloses a prosthesis artificially made in vitro and comprising a time dependent immobilized and insoluble bioabsorbable substance shaped into a prosthetic shape for implantation into a mammal, and having physical means for immobilizing and insolubilizing of the bioabsorbable substance for a predetermined period of time after implantation, wherein the prosthesis may comprise fibroblast growth factors, which fibroblast growth factors or their antagonists might be effective in treating trabecular meshwork and/or ocular tissue in general.

Scar-Retarding (Antifibrotic) Substances and Background

It was reported that Monoclonal antibodies are a promising modality for prevention of scarring after trabeculectomy, according to a current research (OCULAR SURGERY NEWS Sep. 19, 2002 entitled *TGF-beta may help prevent postop scarring*). Several studies are investigating the interaction between growth factors and their role in the induction of postoperative scarring of the filtering bleb. Wimmer and colleagues note in the September issue of *Der Ophthalmologe* that among the growth factors being studied in several trials, TGF-beta 2 plays a key regulatory function. Its concentration in the aqueous humor of patients with primary open-angle glaucoma is significantly elevated, and both in vivo and in vitro studies have shown the growth factor to demonstrate "promising inhibition of scarring after subconjunctival application." In addition, current research indicates the growth factor is a safe and well-tolerated approach to managing postop scarring. It is one aspect of the present invention to provide a growth factor (TGF-beta 2 and the like) to trabecular meshwork at an effective amount to mitigate, eliminate, or retard scar formation at or around the trabecular meshwork. It is a further aspect of the present invention to provide a method of direct delivery of at least one growth factor (TGF-beta, including TGF-beta 2, analog, derivatives and the like) to trabecular meshwork at an effective amount to mitigate, eliminate, or retard scar formation at or around the trabecular meshwork to ocular tissue through an ocularly inserted apparatus or an implant, including a "fistula." In one aspect, the bioactive agent of the invention comprises a scar retarding substance.

U.S. Pat. No. 5,324,508, issued Jun. 28, 1994, the entire contents of which are incorporated herein by reference, discloses a macrophage monokine product having a molecular weight of no more than about 10,000 Dalton, wherein the macrophage monokine appears to be generally effective in inhibiting scar tissue. It is one object of the present invention to incorporate the macrophage monokine product onto a trabecular stent for scar management.

Prof. Peng Khaw (of the Institute of Ophthalmology and Moorfields Eye Hospital) discloses that injecting a neutralizing antibody to the protein transforming growth factor $beta_2$ (TGF-$b_2$) after glaucoma surgery reduced the scarring that is the primary cause for poor postoperative IOP control in a pilot clinical study conducted at Moorfields Eye Hospital and the Western Eye Hospital. Scarring after surgery is the main cause of treatment failures, but the attempt to diminish scarring with anti-cancer drugs can lead to its own set of problems.

Anti-cancer drugs used with glaucoma surgery, which to date have included 5-fluorouracil (5FU) and mitomycin-C, can lead to the creation of acellular, thin, cystic drainage blebs that may leak, resulting in hypotony and potentially blinding infections. Anti-cancer drugs work by killing cells, so they have a lot of potential side effects. Therefore, they are not the ideal treatment, particularly if you want to optimize the pressure lowering in every patient having surgery.

Scarring processes are a big problem in the eye and surrounding structures. Scarring plays a part in either the primary disease or treatment failure of most blinding conditions in the world today. An exception to this repair response is found in the fetal stage, when scarring is minimal. Instead, regeneration primarily occurs. This is associated with low levels of TGF-b in the womb.

It is therefore one aspect of the present invention to provide a method of maintaining a fistula in trabecular meshwork with a scar-retarding substance for re-establishing physiologic outflow in the eye. In one embodiment, the fistula is biodegradable.

U.S. Pat. No. 5,922,369, entire contents of which are incorporated herein by reference, discloses a method of treating eye conditions with human leukocyte elastase (HLE) inhibitory agents. More specifically, it is one object of the present invention to provide a method of reducing tissue or corneal scarring comprising delivery of human leukocyte elastase inhibitory agents an effective amount for scar reducing of a free or polymer-bound HLE inhibitory agent to ocular tissue through an ocularly inserted apparatus or an implant, including a fistula.

Figure 65:
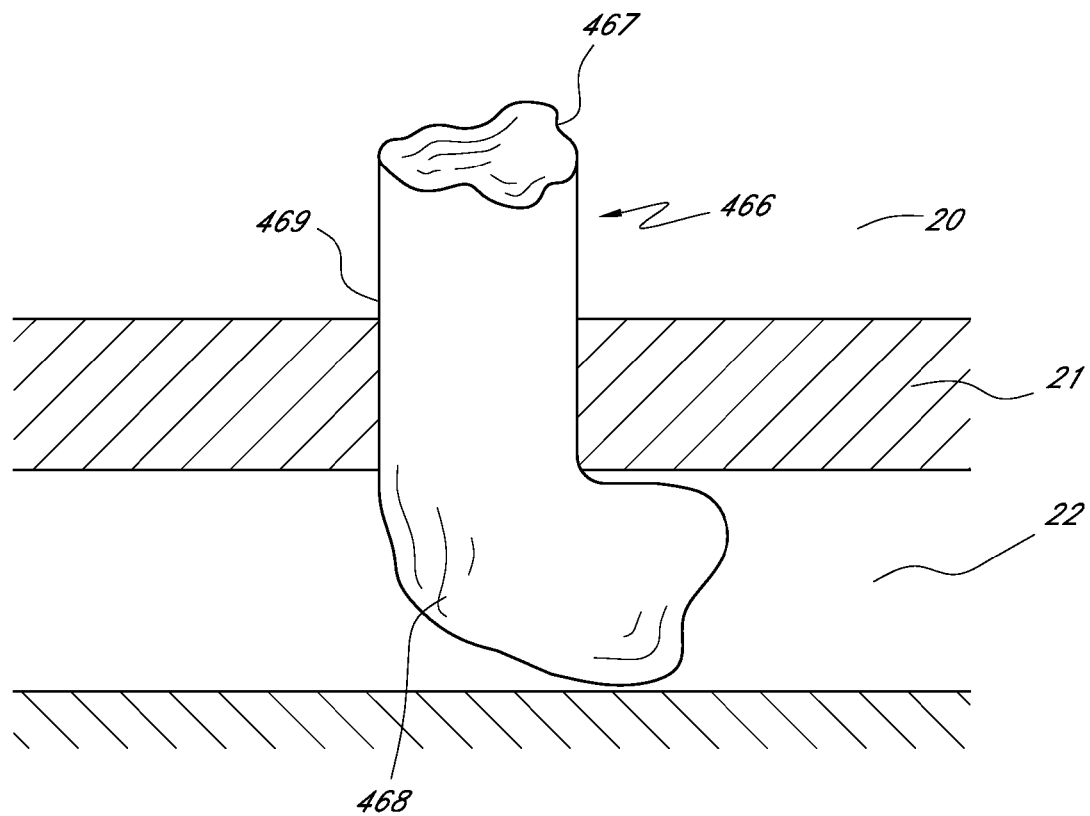
FIG. 65 is one embodiment of a fistula without a lumen for transporting aqueous and carrying bioactive agents of the present invention.

FIG. 65 shows one embodiment for a fistula without a lumen for transporting aqueous. The fistula may be made of a soft flexible material with special surface characteristics to facilitate aqueous transporting along its surface. The material may be selected from a group consisting of silicone, polyurethane, acrylics, and the like. The special surface characteristics for facilitating aqueous transportation may include hydrophilicity, hydrophobicity, surface charge, heparinized surface, surface pH, and drug-coated surface. The surface characteristics may also include mechanical or physical properties such as surface elasticity, surface configuration, shape memory and the like. FIG. 65 shows a fistula 466 comprising a proximal terminal means 467 sized and shaped to be received within the anterior chamber 20 and a distal terminal means 468 sized and shaped to be received within Schlemm's canal 22. A majority of the surface 469 with special characteristics contacts the trabecular meshwork 21 where the facilitated aqueous transportation takes places. The cross-sectional configuration may be any shape, including circular, oval, star, random, and arbitrary or the like.

Some aspects of the invention provides a trabecular bypass stent that is implantable within an eye, the device comprising: an inlet section having an inlet end exposed to an anterior chamber; an outlet section having an outlet end exposed to Schlemm's canal, wherein the device is configured to permit fluid entering the inlet end and then exiting the outlet end; and at least one bioactive agent is loaded onto the stent, wherein the bioactive agent is selected from a group consisting of TGF-beta, a gene, a growth factor, a scar-retarding (or scar-mitigating, scar-limiting, scar-inhibiting) substance. In one aspect of the invention, the therapy combines at least one bioactive agent loaded onto a trabecular bypass stent and a topically administered IOP-lowering eye drop medicine selected from a group consisting (1) Miotics (e.g., pilocarpine, carbachol, and acetylcholinesterase inhibitors), (2) Sympathomimetics (e.g., epinephrine and dipivalylepinephxine), (3) Beta-blockers (e.g., betaxolol, levobunolol and timolol), (4) Carbonic anhydrase inhibitors (e.g., acetazolamide, methazolamide and ethoxzolamide), and (5) Prostaglandins (e.g., metabolite derivatives of arachindonic acid).

Although preferred embodiments of the invention have been described in detail, including devices loaded with TGF-beta and/or bioactive agents, certain variations and modifications will be apparent to those skilled in the art, including embodiments that do not provide all of the features and benefits described herein. Accordingly, the scope of the present invention is not to be limited by the illustrations or the foregoing descriptions thereof, but rather solely by reference to the appended claims and their equivalents.

What is claimed is:

1. A method of treating an ocular disorder, comprising:
   introducing an implant comprising a therapeutic drug into an anterior chamber of an eye such that at least a distal end of the implant is temporarily in the anterior chamber; and
   advancing the distal end of said implant into eye tissue adjacent the anterior chamber such that the implant drains aqueous humor from the anterior chamber into a physiologic outflow pathway and the therapeutic drug reaches eye tissue.

2. The method of claim 1, wherein the implant is coated with said therapeutic drug.

3. The method of claim 1, wherein advancing the implant into eye tissue involves positioning at least a portion of the implant so as to contact a choroid of the eye.

4. The method of claim 1, wherein advancing the implant into eye tissue involves positioning a distal end of the implant so as to drain aqueous humor toward a choroid of the eye.

5. A method of treating an ocular disorder, comprising:
   introducing an implant comprising a therapeutic drug into an anterior chamber of an eye such that at least a distal end of the implant is temporarily in the anterior chamber; and
   advancing the distal end of said implant into eye tissue such that the implant is in contact with at least a choroid of the eye.

6. The method of claim 5 additionally comprising draining aqueous humor from the anterior chamber into a physiologic outflow pathway through the implant.

7. The method of claim 5 additionally comprising controlling aqueous humor flow through a lumen of the implant.

8. The method of claim 5, wherein the implant includes a hollow filled with the therapeutic drug.

9. The method of claim 5, wherein the implant includes a first portion and a second portion that is appended from the first portion, the first portion including a lumen and the second portion carrying the therapeutic drug.

10. The method of claim 5, wherein the therapeutic drug comprises a compound of drugs, at least one of which is therapeutic.

11. A method of treating an ocular disorder, comprising:
    forming an incision in an eye;
    inserting an implant through the incision into an anterior chamber of the eye such that at least a distal end of the implant is temporarily in the anterior chamber, the implant comprising a therapeutic drug; and
    inserting the distal end of the implant into eye tissue such that the implant drains aqueous humor from the anterior chamber toward a choroid of the eye.

12. The method of claim 11 additionally comprising draining aqueous humor from the anterior chamber into a physiologic outflow pathway through the implant.

13. The method of claim 11, wherein the implant includes a first portion and a second portion that is appended from the first portion, the first portion including a lumen and the second portion carrying the therapeutic drug.

14. A method of treating an ocular disorder, comprising:
    introducing an implant into an anterior chamber of an eye such that at least a distal end of the implant is temporarily in the anterior chamber;
    placing the implant in contact with a choroid of the eye by advancing the distal end of the implant into eye tissue, said implant having at least one flow channel;
    flowing a fluid, which comprises aqueous humor, along the flow channel of the implant; and
    eluting a therapeutic agent from the implant.

15. The method of claim 14 additionally comprising advancing the implant through an anterior chamber of the eye toward an implantation site.

16. A method of treating an ocular disorder, comprising:
    providing an implant having at least one lumen extending between an inlet and an outlet, and at least one anchor projecting outwardly from the lumen;
    introducing the implant into an anterior chamber of an eye such that at least a distal end of the implant is temporarily in the anterior chamber;
    using the anchor to retain the implant in eye tissue;
    positioning the outlet in tissue so as to fluidicly communicate directly with a physiologic outflow pathway; and
    eluting a therapeutic agent from the implant.

17. The method of claim 16 additionally comprising advancing the implant through an anterior chamber of the eye toward an implantation site.

18. The method of claim 16 wherein the method further comprises advancing the implant through scleral tissue of the eye when positioning the outlet.

19. A method of treating an ocular disorder, comprising:
    providing an implant having at least one anchor;
    introducing the implant into an anterior chamber of an eye such that at least a distal end of the implant is temporarily in the anterior chamber;
    inserting at least a portion of the implant into eye tissue at an implantation site without penetrating through a cornea or a sclera of the eye;
    using the anchor to retain the implant at said implantation site; and
    eluting a therapeutic agent from the implant.

20. The method of claim 19, wherein introducing the implant into the anterior chamber involves forming an incision in corneal tissue.

21. The method of claim 19, wherein introducing the implant into the anterior chamber involves forming an incision proximate a limbus of the eye.

22. The method of claim 19, wherein introducing the implant into the anterior chamber involves forming a self-sealing incision.

* * * * *

UNITED STATES PATENT AND TRADEMARK OFFICE
CERTIFICATE OF CORRECTION

PATENT NO.         : 7,708,711 B2
APPLICATION NO.    : 10/706300
DATED              : May 4, 2010
INVENTOR(S)        : Hosheng Tu et al.

It is certified that error appears in the above-identified patent and that said Letters Patent is hereby corrected as shown below:

Title Page in Item (56), page 5, column 1, line 43, under Other Publications, please change "Lasesr" to --Laser--.

Title Page in Item (56), page 5, column 1, line 50, under Other Publications, change "Ophthalmololgy," to --Ophthalmology,--.

Title Page in Item (56), page 5, column 1, line 63, under Other Publications, change "Anteriuor" to --Anterior--.

Title Page in Item (56), page 5, column 2, line 19, under Other Publications, change "Graucomatous" to --Glaucomatous--.

Title Page in Item (56), page 5, column 2, line 41, under Other Publications, change "Ophthalmolgy:" to --Ophthalmology:--.

Title Page in Item (56), page 5, column 2, line 49, under Other Publications, change "Ophtoalmology," to --Ophthalmology,--.

Title Page in Item (56), page 5, column 2, line 55, under Other Publications, change "Travecular" to --Trabecular--.

Title Page in Item (56), page 5, column 2, line 56, under Other Publications, change "Ophtoalmology," to --Ophthalmology,--.

Title Page in Item (56), page 5, column 2, line 62, under Other Publications, change "Traveculotomy" to --Trabeculectomy--.

Title Page in Item (56), page 6, column 1, line 7, under Other Publications, change "Presentataions" to --Presentations--.

At column 1, line 9, change "abandoned" to --abandoned,--.

At column 2, line 20, change "juxtacanilicular" to --juxtacanalicular--.

Signed and Sealed this
Eleventh Day of January, 2011

David J. Kappos
*Director of the United States Patent and Trademark Office*

At column 3, line 44, change "microcurrette" to --microcurette--.

At column 4, line 14, change "juxtacanilicular" to --juxtacanalicular--.

At column 4, line 65, change "juxtacanilicular" to --juxtacanalicular--.

At column 8, line 41, change "juxtacanilicular" to --juxtacanalicular--.

At column 11, line 1, change "(Greafe's" to --(Graefe's--.

At column 14, lines 62-63, change "phsophonylmethoxyalkyl" to --phosphonylmethoxyalkyl--.

At column 22, line 58, change "pyrolidone," to --pyrrolidone,--.

At column 29, line 33, change "2.1" to --21--.

At column 33, line 7, change "a" to --an--.

At column 44, lines 43-44, change "pyrolidone," to --pyrrolidone,--.

At column 46, line 59, change "pyrolidone," to --pyrrolidone,--.

At column 48, line 30, change "pyrolidone," to --pyrrolidone,--.

At column 48, lines 30-31, change "polytetrafluordethylene," to --polytetrafluoroethylene,--.

At column 58, line 58, change "arachindonic" to --arachidonic--.